(12) United States Patent
He et al.

(10) Patent No.: US 9,630,902 B2
(45) Date of Patent: Apr. 25, 2017

(54) METHOD OF PREPARING FUSED RING INDENO COMPOUNDS

(71) Applicant: Transitions Optical, Inc., Pinellas Park, FL (US)

(72) Inventors: Meng He, Palm Harbor, FL (US); Massimiliano Tomasulo, Monroeville, PA (US); Allison Greene, Pittsburgh, PA (US); Anil Kumar, Murrysville, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 0 days.

(21) Appl. No.: 14/936,715

(22) Filed: Nov. 10, 2015

(65) Prior Publication Data

US 2016/0060205 A1    Mar. 3, 2016

Related U.S. Application Data

(62) Division of application No. 14/084,739, filed on Nov. 20, 2013, now Pat. No. 9,206,151.

(51) Int. Cl.

| C07D 307/89 | (2006.01) |
|---|---|
| C07D 209/70 | (2006.01) |
| C07C 65/26 | (2006.01) |
| C07C 69/017 | (2006.01) |
| C07C 67/00 | (2006.01) |
| C07D 311/78 | (2006.01) |
| C07C 65/17 | (2006.01) |
| C07C 51/09 | (2006.01) |
| C07D 209/58 | (2006.01) |
| C07D 307/77 | (2006.01) |
| C07C 63/44 | (2006.01) |
| C07C 51/38 | (2006.01) |
| C07C 63/72 | (2006.01) |

(52) U.S. Cl.
CPC ............. *C07C 65/26* (2013.01); *C07C 51/09* (2013.01); *C07C 51/38* (2013.01); *C07C 63/44* (2013.01); *C07C 63/72* (2013.01); *C07C 65/17* (2013.01); *C07C 67/00* (2013.01); *C07C 69/017* (2013.01); *C07D 209/58* (2013.01); *C07D 209/70* (2013.01); *C07D 307/77* (2013.01); *C07D 307/89* (2013.01); *C07D 311/78* (2013.01); *C07C 2102/08* (2013.01); *C07C 2103/40* (2013.01)

(58) Field of Classification Search
CPC ............................ C07D 307/89; C07D 209/70
See application file for complete search history.

(56) References Cited

U.S. PATENT DOCUMENTS

| 8,779,168 B2 | 7/2014 | He et al. |
| 2007/0155964 A1 | 7/2007 | Walters et al. |
| 2012/0156508 A1 | 6/2012 | He et al. |
| 2012/0156521 A1 | 6/2012 | He et al. |
| 2012/0157677 A1 | 6/2012 | He et al. |
| 2012/0157696 A1 | 6/2012 | Chopra et al. |

FOREIGN PATENT DOCUMENTS

| WO | 2012082506 A1 | 6/2012 |
| WO | 2012082513 A1 | 6/2012 |
| WO | 2012082837 A1 | 6/2012 |
| WO | 2012082999 A1 | 6/2012 |

OTHER PUBLICATIONS

Moussa et al., "Heteropolycyclic Molecules. Part IX. Synthesis of Some New Benzo[b]thiophene, Oxofluoreno[4,3-b] thiophene, Cyclic Hydrazides and Acridine Compounds", Journal of Heterocyclic Chemistry, 1981, pp. 1519-1522, vol. 18.

*Primary Examiner* — Shawquia Jackson
(74) *Attorney, Agent, or Firm* — The Webb Law Firm

(57) ABSTRACT

The present invention relates to methods of preparing fused ring indeno compounds that involves reacting together a dienophile and a lactone compound, in the presence of a catalyst, and a carboxylic acid anhydride. With some embodiments, the fused ring indeno compound is represented by the following Formula (I-A), the dienophile is represented by the following Formula (II-A), and the lactone compound is represented by the following Formula (III-A):

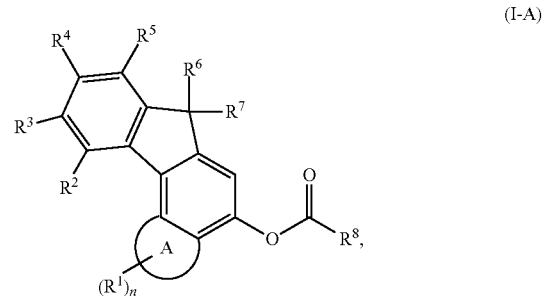

(I-A)

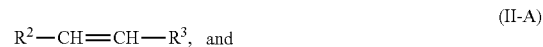

(II-A)

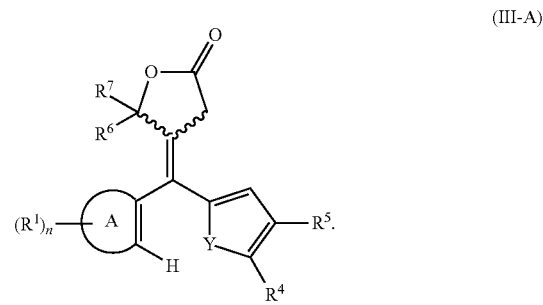

(III-A)

14 Claims, 8 Drawing Sheets

Scheme-(1)

Scheme-(2)

Scheme-(3)

Scheme-(5)

Scheme-(6)

Scheme-(7)

Scheme-(8)

METHOD OF PREPARING FUSED RING INDENO COMPOUNDS

CROSS REFERENCE TO RELATED APPLICATION

The present application is a divisional of and claims priority under 35 U.S.C. §121 to U.S. patent application Ser. No. 14/084,739, filed on Nov. 20, 2013, the disclosure of which is incorporated herein by reference in its entire.

FIELD

The present invention relates to methods of preparing fused ring indeno compounds that involves the reaction of a dienophile and a lactone compound that includes a diene, and certain acid intermediates that are formed during such preparation.

BACKGROUND

Fused ring indeno compounds, such as fused ring indeno naphthols and fused ring indeno naphtha-esters, have many uses, such as intermediates in the synthesis of photochromic compounds and materials, such as indeno-fused ring pyrans, including indeno-fused naphthopyrans. Photochromic materials, such as indeno-fused naphthopyrans, in response to certain wavelengths of electromagnetic radiation (or "actinic radiation"), typically undergo a transformation from one form or state to another form, with each form having a characteristic or distinguishable absorption spectrum associated therewith. Typically, upon exposure to actinic radiation, many photochromic materials are transformed from a closed-form, which corresponds to an unactivated (or bleached, or substantially colorless) state of the photochromic material, to an open-form, which corresponds to an activated (or colored) state of the photochromic material. In the absence of exposure to actinic radiation, such photochromic materials are reversibly transformed from the activated (or colored) state, back to the unactivated (or bleached) state. Compositions and articles, such as eyewear lenses, that contain photochromic materials or have photochromic materials applied thereto (such as in form of a photochromic coating composition) typically display colorless (or clear) and colored states that correspond to the colorless and colored states of the photochromic materials contained therein and/or applied thereto.

Fused ring indeno compounds, such as indeno-fused naphthol materials are typically prepared by a synthetic scheme involving the reaction of a benzophenone with a dialkyl succinate, which is typically referred to as a Stobbe reaction route. Such known methods can be limited with regard to the types of groups, such as precursor groups and lengthening groups, and the ring-positions of such groups on the resulting fused ring indeno compounds. The introduction of groups at various ring positions can involve additional synthetic steps, and in some instances reduced product yields due in some cases to additional isolation steps.

Some photochromic materials, such as photochromic indeno-fused naphthopyrans can be expensive, and in light of economic considerations, reducing the costs associated with synthesizing such materials is typically desirable.

It would be desirable to develop new methods of preparing fused ring indeno compounds, such as fused ring indeno naphtho-esters and fused ring indeno naphthols.

In addition, it would be desirable that such newly developed methods provide compounds having certain groups, such as precursor groups, and ring-positions that are not possible or readily obtainable with present synthetic methods.

SUMMARY

In accordance with the present invention, there is provided a method of forming a fused ring indeno compound, which can be used with some embodiments as an intermediate for preparation of a photochromic compound, wherein the fused ring indeno compound is represented by the following Formula (I-A),

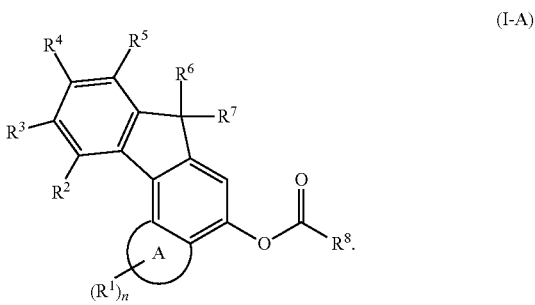

(I-A)

With reference to Formula (I-A), Ring-A is selected from aryl and fused ring aryl, and n is selected from 1 to 8.

With further reference to Formula (I-A), $R^1$ for each n is independently selected from hydrogen; hydrocarbyl and substituted hydrocarbyl each optionally and independently interrupted with at least one of —O—, —S—, —C(O)—, —C(O)O—, —S(O)—, —SO$_2$—, —N=N—, —N($R_{11}$')— where $R_{11}$' is selected from hydrogen, hydrocarbyl or substituted hydrocarbyl, —Si(O$R_8$')$_w$($R_8$')$_t$—, where w and t are each independently selected from 0 to 2, provided that the sum of w and t is 2, and each $R_8$' is independently selected from hydrogen, hydrocarbyl and substituted hydrocarbyl, and combinations of two or more thereof; halogen; cyano; —O—$R_{10}$' or —S—$R_{10}$' or —C(O)—$R_{10}$' or —C(O)—O$R_{10}$', wherein each $R_{10}$' is independently selected from hydrogen, hydrocarbyl or substituted hydrocarbyl; perhalohydrocarbyl; and —C(O)—N($R_{11}$')($R_{12}$') or —N($R_{11}$')$R_{12}$', wherein $R_{11}$' and $R_{12}$' are each independently selected from hydrogen, hydrocarbyl or substituted hydrocarbyl, or $R_{11}$' and $R_{12}$' together form a ring structure optionally including at least one heteroatom, With additional reference to Formula (I-A), $R^2$ and $R^3$ are each independently selected from hydrogen, cyano, nitro, —C(O)O—$R_9$, —C(O)—N($R_{10}$)($R_{11}$), —C(O)—N(C(O) O$R_{10}$)($R_{11}$), —C(O)$R_{12}$, —OC(O)$R_{12}$, —SO$_2R_{13}$, —OSO$_2R_{13}$, —B(O$R_{14}$)(O$R_{15}$), hydrocarbyl, perhalohydrocarbyl, and halogen, wherein $R_9$, $R_{10}$, $R_{11}$, $R_{12}$, $R_{13}$, $R_{14}$, and $R_{15}$ are each independently selected from hydrogen, hydrocarbyl, substituted hydrocarbyl, and perhalohydrocarbyl, or $R_{10}$ and $R_{11}$ together form a ring, or $R_{14}$ and $R_{15}$ together form a ring. Alternatively, $R^2$ and $R^3$ together form a ring optionally interrupted with a divalent linking group selected from —C(O)—, —S—, hydrocarbyl, —O—, —N($R_{13}$)—, and combinations of two or more thereof, where $R_{13}$ is selected from hydrogen, hydrocarbyl and substituted hydrocarbyl each optionally and independently interrupted with at least one of —O—, —S—, —C(O)—, —C(O)O—, —S(O)—, —SO$_2$—, —N=N—, —N($R_{11}$')— where $R_{11}$' is selected from hydrogen, hydrocarbyl or substituted hydrocarbyl, —Si(O$R_8$')$_w$($R_8$')$_t$—, where w and t are each independently selected from 0 to 2, provided that the sum of w and t is 2, and each $R_8'$ is independently selected from hydrogen, hydrocarbyl and substituted hydrocarbyl, and combinations of two or more thereof.

With reference to Formula (I-A), $R^4$ and $R^5$ are each independently selected from hydrogen, hydrocarbyl, substituted hydrocarbyl, halogen, —C(O)—N($R_{14}$)($R_{15}$), —N($R_{14}$)($R_{15}$), —S$R_{16}$, and —O$R_{16}$, where $R_{14}$ and $R_{15}$ are each independently selected from hydrogen, hydrocarbyl, and substituted hydrocarbyl, or $R_{14}$ and $R_{15}$ together form a ring, and each $R_{16}$ is independently selected from hydrocarbyl and substituted hydrocarbyl.

With further additional reference to Formula (I-A), $R^6$ and $R^7$ are each independently selected from hydrogen, hydrocarbyl, and substituted hydrocarbyl, each optionally and independently interrupted with —O—, —S—, —N($R_{11}'$)—, where $R_{11}'$ is selected from hydrogen, hydrocarbyl or substituted hydrocarbyl.

The group $R^8$ of Formula (I-A) is selected from hydrocarbyl, substituted hydrocarbyl, and perhalohydrocarbyl.

The method of the present invention comprises, reacting together a dienophile represented by the following Formula (II-A) and a lactone compound represented by the following Formula (III-A), in the presence of a catalyst, and a carboxylic acid anhydride represented by the following Formula (IV), $$R^2-CH=CH-R^3 \quad \text{(II-A)}$$

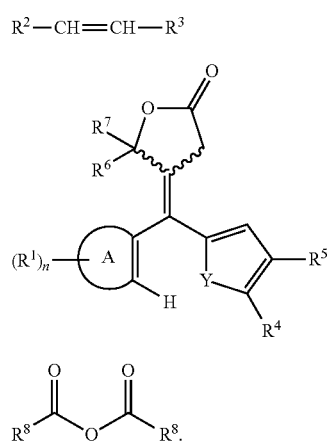

(III-A)

(IV)

With the dienophile represented by Formula (II-A), $R^2$ and $R^3$ are each as described herein with regard to the fused ring indeno compound represented by Formula (I-A).

With the lactone compound represented by Formula (III-A), Ring-A, n, $R^1$, $R^4$, $R^5$, $R^6$, and $R^7$ are each as described herein with regard to the fused ring indeno compound represented by Formula (I-A), and Y is selected from O, S, and N($R_{18}$), where $R_{18}$ is selected from hydrogen, hydrocarbyl, and substituted hydrocarbyl.

With the carboxylic acid anhydride represented by Formula (IV) each $R^8$ is independently as described herein with regard to the fused ring indeno compound represented by Formula (I-A).

In accordance with the present invention, there is further provided a method of forming a fused ring indeno compound, which can be used with some embodiments an intermediate for preparation of a photochromic compound, wherein the fused ring indeno compound is represented by the following Formula (I-E),

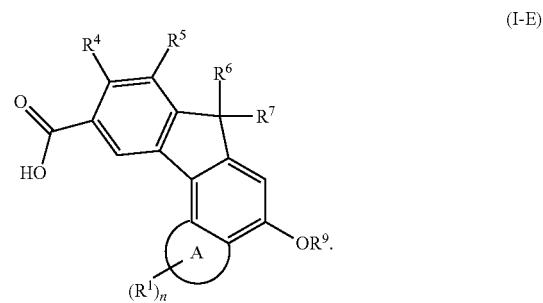

With reference to Formula (I-E), Ring-A, n, $R^1$, $R^4$, $R^5$, $R^6$, and $R^7$ are each independently as described herein with reference to Formula (I-A). The group $R^9$ of Formula (I-E) is selected from —C(O)—$R_{19}$ and —S(O)(O)$R_{19}$, wherein $R_{19}$ is selected from hydrocarbyl, and halohydrocarbyl.

The method of forming the fused ring indeno compound represented by Formula (I-E) comprises, (a) in a first step, reacting together maleic anhydride and a lactone compound represented by the following Formula (III-A), in the presence of a catalyst, and a solvent, in which the solvent is substantially free of reaction with water, thereby forming an acid intermediate represented by Formula (VIII-A),

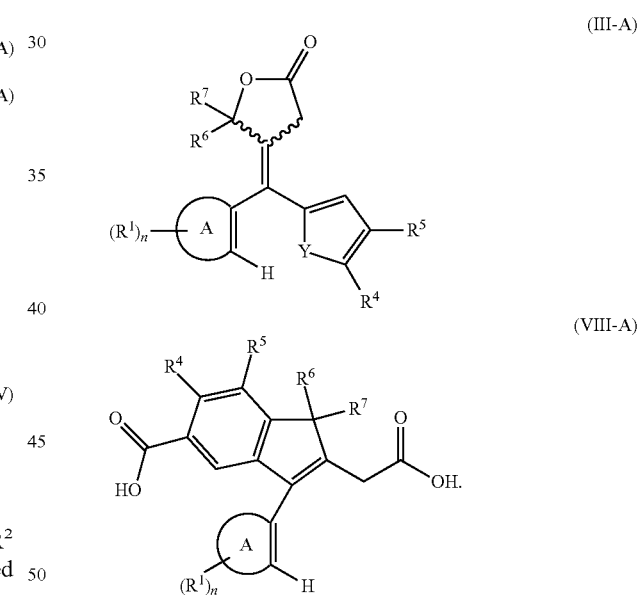

Ring-A, n, $R^1$, $R^4$, $R^5$, $R^6$, and $R^7$ of Formulas (III-A) and (VIII-A), and Y of Formula (III-A) are each independently as described herein with reference to Formula (I-A) and Formula (III-A).

The method of forming the fused ring indeno compound represented by Formula (I-E) further comprises, (b) in a second step, converting the acid intermediate represented by Formula (VIII-A) to the fused ring indeno compound represented by Formula (I-E) in the presence of a material selected from carboxylic acid halide, carboxylic acid anhydride, sulfonyl halide, sulfonyl anhydride, and combinations thereof.

In accordance with the present Invention, there is further provided a compound, which can be used with some embodiments an intermediate for preparation of a photochromic compound, wherein the compound is represented by the following Formula (VIII-A),

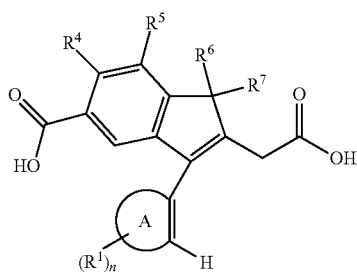

With reference to Formula (VIII-A), Ring-A, n, $R^1$, $R^4$, $R^5$, $R^6$, and $R^7$ are each independently as described herein with regard to Formula (I-A). The compound represented by Formula (VIII-A) is, with some embodiments, referred to as an acid intermediate.

The features that characterize the present invention are pointed out with particularity in the claims, which are annexed to and form a part of this disclosure. These and other features of the invention, its operating advantages and the specific objects obtained by its use will be more fully understood from the following detailed description in which non-limiting embodiments of the invention are illustrated and described.

BRIEF DESCRIPTION OF THE DRAWINGS

In FIGS. 1-8 like characters refer to the same compounds, reactants, and/or groups as the case may be, unless otherwise stated.

DETAILED DESCRIPTION

Figure 1:
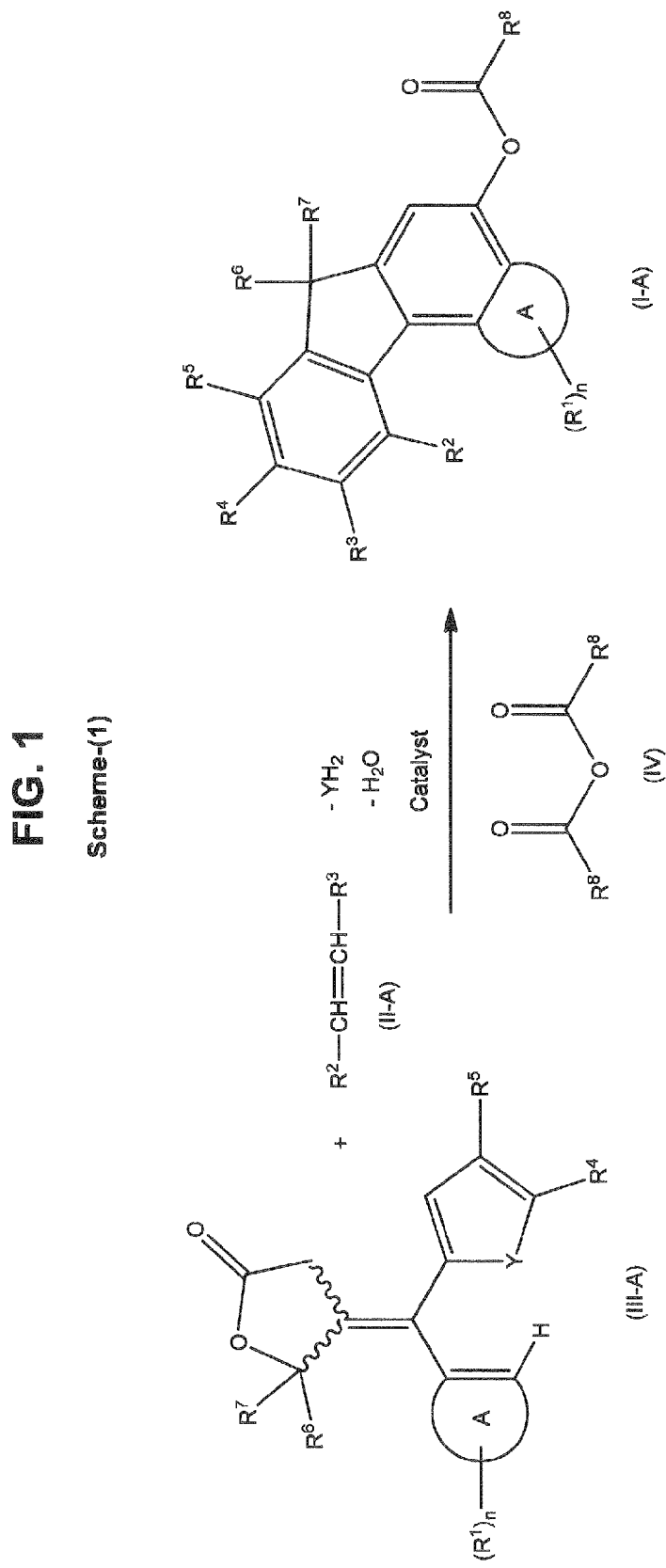
FIG. 1 is an illustrative representative general scheme, Scheme-(1), of the method of the present invention.

As used herein, the articles "a," "an," and "the" include plural referents unless otherwise expressly and unequivocally limited to one referent.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein, unless otherwise indicated, left-to-right representations of inking groups, such as divalent linking groups, are inclusive of other appropriate orientations, such as, but not limited to, right-to-left orientations. For purposes of non-limiting illustration, the left-to-right representation of the divalent linking group

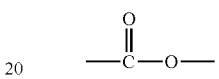

or equivalently —C(O)O—, is inclusive of the right-to-left representation thereof,

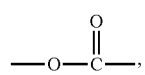

or equivalently —O(O)C— or —OC(O)—.

Other than in the operating examples, or where otherwise indicated, all numbers expressing quantities of ingredients, reaction conditions, and so forth used in the specification and claims are to be understood as modified in all instances by the term "about."

The various materials, compounds, and intermediates prepared by the methods of the present invention, and materials, compounds, and intermediates of the present invention, as described herein, including, but not limited to compounds represented by Formula (I-A), Formula (I-B), Formula (I-C), Formula (I-D), Formula (I-E), Formula (VIII-A), Formula (I-F), Formula (I-G), and Formula (VIII-B), in each case optionally further include one or more coproducts, resulting from the synthesis of such materials, compounds, and intermediates.

As used herein, the term "photochromic" and similar terms, such as "photochromic compound" means having an absorption spectrum for at least visible radiation that varies in response to absorption of at least actinic radiation. Further, as used herein the term "photochromic material" means any substance that is adapted to display photochromic properties (such as, adapted to have an absorption spectrum for at least visible radiation that varies in response to absorption of at least actinic radiation) and which includes at least one photochromic compound.

As used herein, the term "actinic radiation" means electromagnetic radiation that is capable of causing a response in a material, such as, but not limited to, transforming a photochromic material from one form or state to another as will be discussed in further detail herein.

As used herein, the term "photochromic material" includes thermally reversible photochromic materials and compounds and non-thermally reversible photochromic materials and compounds. The term "thermally reversible photochromic compounds/materials" as used herein means compounds/materials capable of converting from a first state, for example a "clear state," to a second state, for example a "colored state," in response to actinic radiation, and reverting back to the first state in response to thermal energy. The term "non-thermally reversible photochromic compounds/materials" as used herein means compounds/ materials capable of converting from a first state, for example a "clear state," to a second state, for example a "colored state," in response to actinic radiation, and reverting back to the first state in response to actinic radiation of substantially the same wavelength(s) as the absorption(s) of the colored state (e.g., discontinuing exposure to such actinic radiation).

As used herein to modify the term "state," the terms "first" and "second" are not intended to refer to any particular order or chronology, but instead refer to two different conditions or properties. For purposes of non-limiting illustration, the first state and the second state of a photochromic compound can differ with respect to at least one optical property, such as but not limited to the absorption of visible and/or UV radiation. Thus, according to various non-limiting embodiments disclosed herein, the photochromic compounds of the present invention can have a different absorption spectrum in each of the first and second state. For example, while not limiting herein, a photochromic compound prepared from the fused ring indeno compounds prepared by the method of the present invention can be clear in the first state and colored in the second state. Alternatively, a photochromic compound prepared from the fused ring indeno compounds prepared by the method of the present invention can have a first color in the first state and a second color in the second state.

As used herein the term 'optical' means pertaining to or associated with light and/or vision. For example, according to various non-limiting embodiments disclosed herein, the optical article or element or device can be chosen from ophthalmic articles, elements and devices, display articles, elements and devices, windows, mirrors, and active and passive liquid crystal cell articles, elements and devices.

As used herein the term 'ophthalmic' means pertaining to or associated with the eye and vision. Non-limiting examples of ophthalmic articles or elements include corrective and non-corrective lenses, Including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intra-ocular lenses, magnifying lenses, and protective lenses or visors.

As used herein the term "display" means the visible or machine-readable representation of information in words, numbers, symbols, designs or drawings. Non-limiting examples of display elements include screens, monitors, and security elements, such as security marks.

As used herein the term "window" means an aperture adapted to permit the transmission of radiation therethrough. Non-limiting examples of windows include automotive and aircraft transparencies, windshields, filters, shutters, and optical switches.

As used herein the term "mirror" means a surface that specularly reflects a large fraction of incident light.

As used herein the term "liquid crystal cell" refers to a structure containing a liquid crystal material that is capable of being ordered. A non-limiting example of a liquid crystal cell element is a liquid crystal display.

As used herein, spatial or directional terms, such as "left", "right", "inner", "outer", "above", "below", and the like, relate to the invention as it is depicted in the drawing figures. It is to be understood, however, that the invention can assume various alternative orientations and, accordingly, such terms are not to be considered as limiting.

As used herein, the terms "formed over," "deposited over," "provided over," "applied over," residing over," or "positioned over," mean formed, deposited, provided, applied, residing, or positioned on but not necessarily in direct (or abutting) contact with the underlying element, or surface of the underlying element. For example, a layer "positioned over" a substrate does not preclude the presence of one or more other layers, coatings, or films of the same or different composition located between the positioned or formed layer and the substrate.

As used herein, the term "Ring Position" means a particular position in the ring structure, such as the fused ring structure, of a chemical compound, such as the fused ring indeno compounds and intermediates prepared by method of the present invention, and which are depicted herein in accordance with some embodiments by numbers within the ring structures of representative chemical formulas.

All documents, such as but not limited to issued patents and patent applications, referred to herein, and unless otherwise indicated, are to be considered to be "incorporated by reference" in their entirety.

As used herein, recitations of "linear or branched" groups, such as linear or branched alkyl, are herein understood to include: a methylene group or a methyl group; groups that are linear, such as linear $C_2$-$C_{20}$ alkyl groups; and groups that are appropriately branched, such as branched $C_3$-$C_{20}$ alkyl groups.

As used herein, recitations of "optionally substituted" group, means a group, including but not limited to, alkyl group, cycloalkyl group, heterocycloalkyl group, aryl group, and/or heteroaryl group, in which at least one hydrogen thereof has been optionally replaced or substituted with a group that is other than hydrogen, such as, but not limited to, halo groups (e.g., F, Cl, I, and Br), hydroxyl groups, ether groups, thiol groups, thio ether groups, carboxylic acid groups, carboxylic acid ester groups, phosphoric acid groups, phosphoric acid ester groups, sulfonic acid groups, sulfonic acid ester groups, nitro groups, cyano groups, hydrocarbyl groups (including, but not limited to: alkyl; alkenyl; alkynyl; cycloalkyl, including poly-fused-ring cycloalkyl and polycycloalkyl; heterocycloalkyl; aryl, including hydroxyl substituted aryl, such as phenol, and including poly-fused-ring aryl; heteroaryl, including poly-fused-ring heteroaryl; and aralkyl groups), and amine groups, such as —N($R_{11}$')($R_{12}$') where $R_{11}$' and $R_{12}$' are each independently selected, with some embodiments, from hydrogen, linear or branched $C_1$-$C_{20}$ alkyl, $C_3$-$C_{12}$ cycloakyl, $C_3$-$C_{12}$ heterocycloalkyl, aryl, and heteroaryl.

As used herein, recitations of "halo substituted" and related terms (such as, but not limited to, haloalkyl groups, haloalkenyl groups, haloalkynyl groups, haloaryl groups and halo-heteroaryl groups) means a group in which at least one, and up to and including all of the available hydrogen groups thereof is substituted with a halo group. The term "halo-substituted" is inclusive of "perhalo-substituted." As used herein, the term perhalo-substituted group and related terms (such as, but not limited to perhaloalkyl groups, perhaloalkenyl groups, perhaloalkynyl groups, perhaloaryl groups and perhalo-heteroaryl groups) means a group in which all of the available hydrogen groups thereof are substituted with a halo group. For example, perhalomethyl is —$CX_3$; perhalophenyl is —$C_6X_5$, where X represents one or more halo groups, such as, but not limited to F.

The fused ring indeno compounds prepared by the method of the present invention, various intermediates and co-reactants used in the method of the present invention, and those compounds according to the present invention include groups and sub-groups that can in each case be independently selected from hydrocarbyl and/or substituted hydrocarbyl. As used herein the term "hydrocarbyl" and similar terms, such as "hydrocarbyl substituent," means: linear or branched $C_1$-$C_{25}$ alkyl (e.g., linear or branched $C_1$-$C_{10}$ alkyl); linear or branched $C_2$-$C_{25}$ alkenyl (e.g., linear or branched $C_2$-$C_{10}$ alkenyl); linear or branched $C_2$-$C_{25}$ alkynyl (e.g., linear or branched $C_2$-$C_{10}$ alkynyl); $C_3$-$C_{12}$ cycloalkyl (e.g., $C_3$-$C_{10}$ cycloalkyl); $C_3$-$C_{12}$ heterocycloalkyl (having at least one hetero atom in the cyclic ring); $C_5$-$C_{18}$ aryl (including polycyclic aryl groups) (e.g., $C_3$-$C_{10}$ aryl); $C_5$-$C_{18}$ heteroaryl (having at least one hetero atom in the aromatic ring); and $C_6$-$C_{24}$ aralkyl (e.g., $C_6$-$C_{10}$ aralkyl).

Representative alkyl groups include but are not limited to methyl, ethyl, propyl, isopropyl, butyl, isobutyl, sec-butyl, tert-butyl, pentyl, neopentyl, hexyl, heptyl, octyl, nonyl and decyl. Representative alkenyl groups include but are not limited to vinyl, allyl and propenyl. Representative alkynyl groups include but are not limited to ethynyl, 1-propynyl, 2-propynyl, 1-butynyl, and 2-butynyl. Representative cycloalkyl groups include but are not limited to cyclopropyl, cyclobutyl, cyclopentyl, cyclohexyl, and cyclooctyl substituents. Representative heterocycloalkyl groups include but are not limited to imidazolyl, tetrahydrofuranyl, tetrahydropyranyl and piperidinyl. Representative aryl groups include but are not limited to phenyl, naphthyl, anthracynyl and triptycenyl. Representative heteroaryl groups include but are not limited to furanyl, pyranyl, pyridinyl, isoquinoline, and pyrimidinyl. Representative aralkyl groups include but are not limited to benzyl, and phenethyl.

The term "substituted hydrocarbyl" as used herein means a hydrocarbyl group in which at least one hydrogen thereof has been substituted with a group that is other than hydrogen, such as, but not limited to, halo groups, hydroxyl groups, ether groups, thiol groups, thio ether groups, carboxylic acid groups, carboxylic acid ester groups, phosphoric acid groups, phosphoric acid ester groups, sulfonic acid groups, sulfonic acid ester groups, nitro groups, cyano groups, hydrocarbyl groups (e.g., alkyl, alkenyl, alkynyl, cycloalkyl, heterocycloalkyl, aryl, heteroaryl, and aralkyl groups), and amine groups, such as —N($R_{11}$')($R_{12}$') where $R_{11}$' and $R_{12}$' are each independently selected from hydrogen, hydrocarbyl and substituted hydrocarbyl.

The term "substituted hydrocarbyl" is inclusive of halohydrocarbyl (or halo substituted hydrocarbyl) substituents. The term "halohydrocarbyrl" as used herein, and similar terms, such as halo substituted hydrocarbyl, means that at least one hydrogen atom of the hydrocarbyl (e.g., of the alkyl, alkenyl, alkynyl, cycloalkyl, heterocycloalkyl, aryl, heteroaryl, and aralkyl groups) is replaced with a halogen atom selected from chlorine, bromine, fluorine and iodine. The degree of halogenation can range from at least one hydrogen atom but less than all hydrogen atoms being replaced by a halogen atom (e.g., a fluoromethyl group), to full halogenation (perhalogenation) in which all replaceable hydrogen atoms on the hydrocarbyl group have each been replaced by a halogen atom (e.g., trifluoromethyl or perfluoromethyl). Correspondingly, the term "perhalohydrocarbyl group" as used herein means a hydrocarbyl group in which all replaceable hydrogens have been replaced with a halogen. Examples of perhalohydrocarbyl groups include, but are not limited to, perhalogenated phenyl groups and perhalogenated alkyl groups.

The hydrocarbyl and substituted hydrocarbyl groups from which the various groups described herein can each be independently selected, in some instances and with some embodiments, can in each case be independently and optionally interrupted with at least one of —O—, —S—, —C(O)—, —C(O)O—, —S(O)—, —SO$_2$—, —N═N—, —N($R_{11}$')— where $R_{11}$' is selected from hydrogen, hydrocarbyl or substituted hydrocarbyl, —Si(O$R_8$')$_w$($R_8$')$_t$—, where w and t are each independently selected from 0 to 2, provided that the sum of w and t is 2, and each $R_8$' is independently selected from hydrogen, hydrocarbyl and substituted hydrocarbyl, and combinations of two or more thereof. As used herein, by interrupted with at least one of —O—, —S—, —C(O)—, —C(O)O—, —OC(O)O—, —S(O)—, —SO$_2$—, —N═N—, —N($R_{11}$')—, and —Si(O$R_8$')$_w$($R_8$')$_t$—, means that at least one carbon of, but less than all of the carbons of, the hydrocarbyl group or substituted hydrocarbyl group, is in each case independently replaced with one of the recited divalent non-carbon linking groups. The hydrocarbyl and substituted hydrocarbyl groups can be interrupted with two or more of the above recited linking groups, which can be adjacent to each other or separated by one or more carbons. For purposes of non-limiting illustration, a combination of adjacent —C(O)— and —N($R_{11}$')— can provide a divalent amide linking or interrupting group, —C(O)—N($R_{11}$')—. For purposes of further non-limiting illustration, a combination of adjacent —N($R_{11}$')—, —C(O)— and —O— can provide a divalent carbamate (or urethane) linking or interrupting group, —N($R_{11}$')—C(O)—O—, where $R_{11}$' is hydrogen.

The term "alkyl" as used herein, in accordance with some embodiments, means linear or branched alkyl, such as but not limited to, linear or branched $C_1$-$C_{25}$ alkyl, or linear or branched $C_1$-$C_{10}$ alkyl, or linear or branched $C_2$-$C_{10}$ alkyl. Examples of alkyl groups from which the various alkyl groups of the present invention can be selected from, include, but are not limited to, those recited previously herein. Alkyl groups of the various compounds of the present invention can, with some embodiments, include one or more unsaturated linkages selected from —CH═CH— groups and/or one or more —C≡C— groups, provided the alkyl group is free of two or more conjugated unsaturated linkages. With some embodiments, the alkyl groups are free of unsaturated linkages, such as —CH═CH— groups and —C≡C— groups.

The term "cycloalkyl" as used herein, in accordance with some embodiments, means groups that are appropriately cyclic, such as but not limited to, $C_3$-$C_{12}$ cycloalkyl (including, but not limited to, cyclic $C_3$-$C_7$ alkyl) groups. Examples of cycloalkyl groups include, but are not limited to, those recited previously herein. The term "cycloalkyl" as used herein in accordance with some embodiments also includes: bridged ring polycycloalkyl groups (or bridged ring polycyclic alkyl groups), such as but not limited to, bicyclo[2.2.1]heptyl (or norbornyl) and bicyclo[2.2.2]octyl; and fused ring polycycloalkyl groups (or fused ring polycyclic alkyl groups), such as, but not limited to, octahydro-1H-indenyl, and decahydronaphthalenyl.

The term "heterocycloalkyl" as used herein, in accordance with some embodiments, means groups that are appropriately cyclic, such as but not limited to, $C_3$-$C_{12}$ heterocycloalkyl groups or $C_5$-$C_7$ heterocycloalkyl groups, and which have at least one hetero atom in the cyclic ring, such as, but not limited to, O, S, N, P, and combinations thereof. Examples of heterocycloalkyl groups include, but are not limited to, those recited previously herein. The term "heterocycloalkyl" as used herein, in accordance with some embodiments, also includes: bridged ring polycyclic heterocycloalkyl groups, such as but not limited to, 7-oxabicyclo[2.2.1]heptanyl; and fused ring polycyclic heterocycloalkyl groups, such as but not limited to, octahydrocyclopenta[b]pyranyl, and octahydro-1H-isochromenyl.

The term "heteroaryl," as used herein, in accordance with some embodiments, includes but is not limited to $C_3$-$C_{18}$ heteroaryl, such as but not limited to $C_3$-$C_{10}$ heteroaryl (including fused ring polycyclic heteroaryl groups) and means an aryl group having at least one hetero atom in the aromatic ring, or in at least one aromatic ring in the case of a fused ring polycyclic heteroaryl group. Examples of heteroaryl groups include, but are not limited to, those recited previously herein.

As used herein, the term "fused ring polycyclic-aryl-alkyl group" and similar terms such as, fused ring polycyclic-alkyl-aryl group, fused ring polycyclo-aryl-alkyl group, and fused ring polycyclo-alkyl-aryl group means a fused ring polycyclic group that includes at least one aryl ring and at least one cycloalkyl ring that are fused together to form a fused ring structure. For purposes of non-limiting illustration, examples of fused ring polycyclic-aryl-alkyl groups include, but are not limited to indenyl, 9H-fluorenyl, cyclopentanaphthenyl, and indacenyl.

The term "aralkyl," as used herein, and in accordance with some embodiments, includes but is not limited to $C_6$-$C_{24}$ aralkyl, such as but not limited to $C_6$-$C_{10}$ aralkyl, and means an aryl group substituted with an alkyl group. Examples of aralkyl groups include, but are not limited to, those recited previously herein.

The method of the present invention, the fused ring indeno compounds prepared by and various intermediates and co-reactants formed and/or used with the method of the present invention, and compounds according to the present invention, such as, but not limited to those represented by Formulas (I-A), (I-B), (I-C), (I-D), (I-E), (VIII-A), (I-F), (I-G), and (VIII-B), and the various groups thereof are described in further detail herein as follows.

The formulas representing the lactone compound of the method of the present invention, such as Formula (III-A), include wavy bonds (〰), which, as used herein, means each formula represents two structural isomers relative to the double bond extending from the lactone moiety at the junction point of the two wavy bonds. For purposes of non-limiting illustration, with the lactone compound represented by Formula (III-A), the wavy bonds (〰) mean the positions of the Ring-(A) and the five member ring (including Y, $R^4$, and $R^5$) can be switched relative to the double bond. For purposes of further non-limiting illustration, the lactone compound represented by Formula (III-A) includes lactone compounds represented by the following Formula (III-A') and Formula (III-A"):

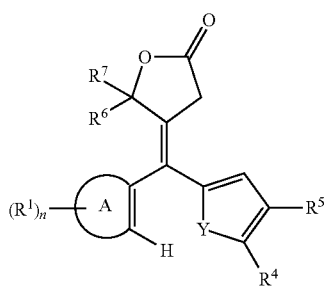

(III-A')

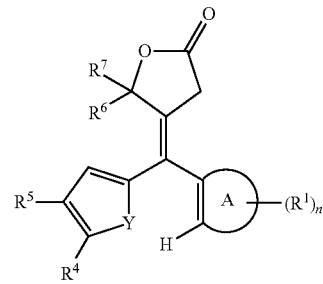

(III-A")

For purposes of non-limiting illustration, the method of forming the fused ring indeno compound represented by Formula (I-A), in accordance with some embodiments of the present invention, is summarized in Scheme-(1) of FIG. 1.

With reference to Scheme-(1) of FIG. 1, Formulas (I-A), (II-A), (III-A), and (IV) are each as described previously and further herein. With further reference to Scheme-(1), Y of the lactone compound represented by Formula (III-A) is selected from O, S, and N($R_{18}$), where $R_{15}$ is as described previously and further herein. While not intending to be bound by any theory, it is believed that the dienophile represented by Formula (II-A) and the cyclic diene moiety (that includes Y, $R^4$ and $R^5$) of the lactone represented by Formula (III-A) react together by a Diels-Alder reaction.

With further reference to Scheme-(1) of FIG. 1, the group Y of the lactone compound, such as represented by Formula (III-A), is not present in or otherwise incorporated into the structure of the fused ring indeno compound represented by Formula (I-A). During the course of the method of the present invention, Y of the lactone compounds, such as represented by Formula (III-A), forms: $H_2O$ (when Y is O); $SH_2$ (when Y is S); or $NH_2(R_{18})$ (when Y is N($R_{18}$)). While not intending to be bound by any theory, the conversion of Y of the lactone, such as represented by Formula (III-A), to $H_2O$, $SH_2$, or $NH_2(R_{18})$ is believed to occur during the aromatization step of the reaction.

Figure 2:
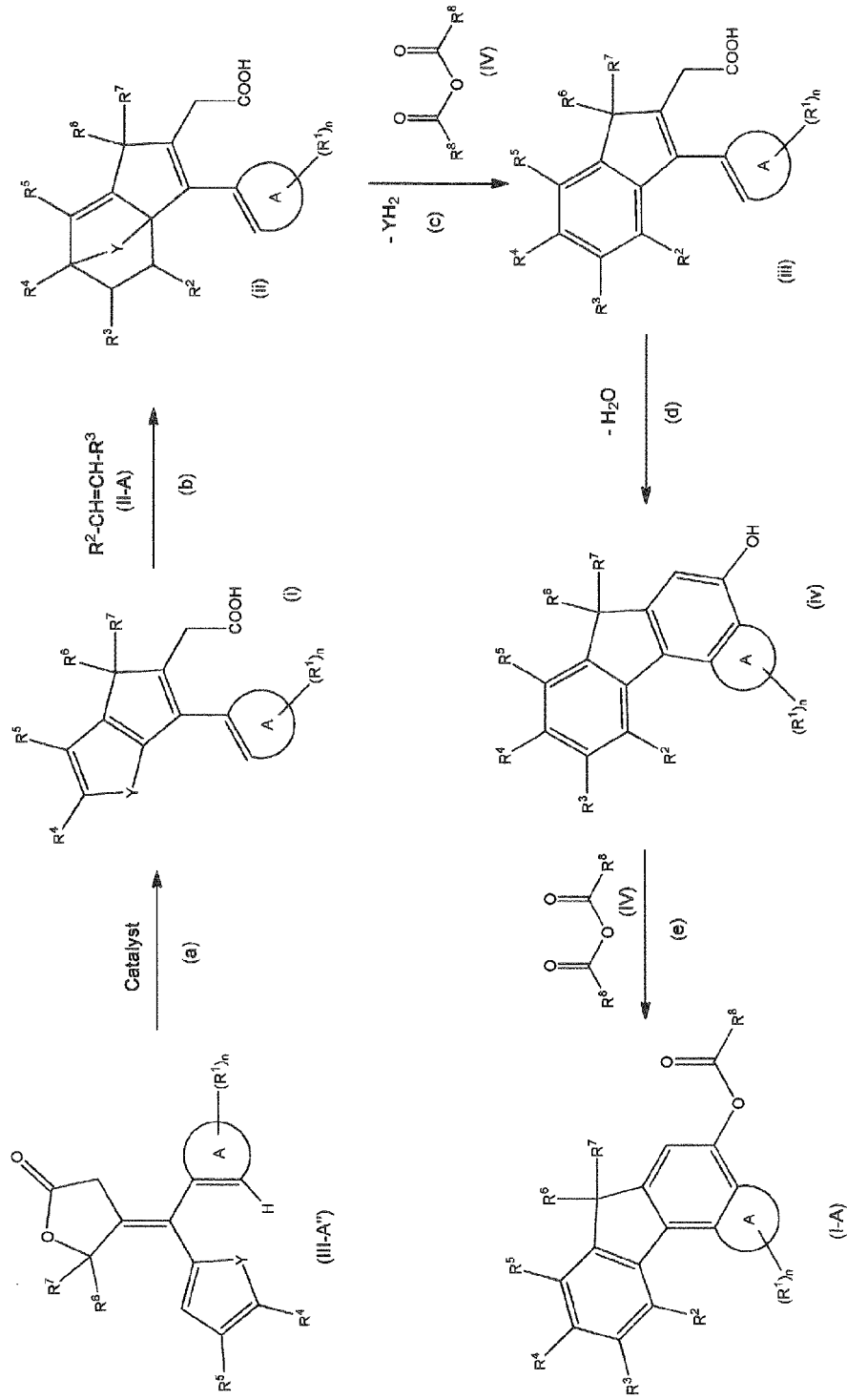
FIG. 2 is an illustrative representative scheme, Scheme-(2), of the method of the present invention.
Figure 3:
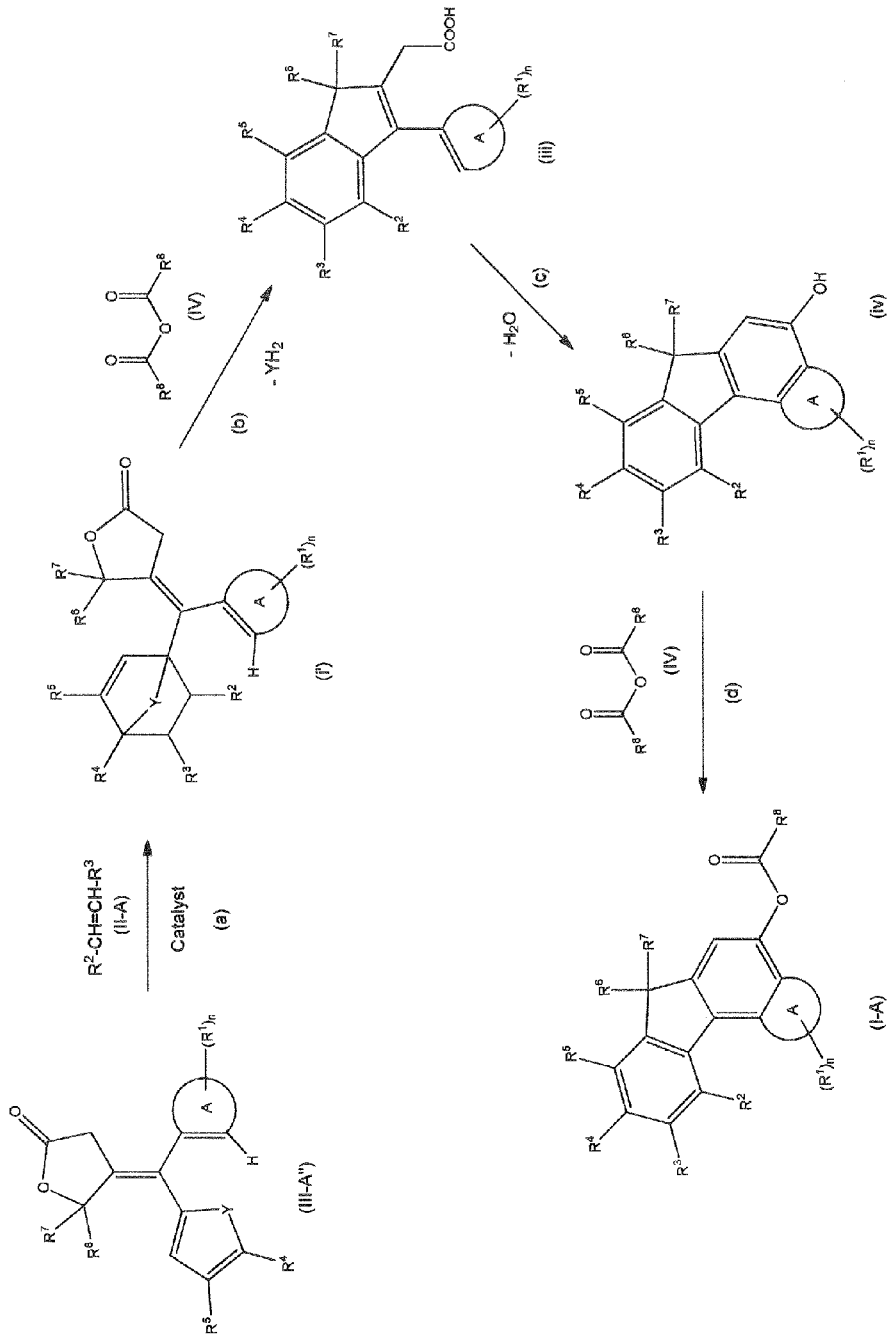
FIG. 3 is an illustrative representative scheme, Scheme-(3), of the method of the present invention.

While not intending to be bound by any theory and for purposes of non-limiting illustration, and based on the evidence presently at hand, the method of the present invention, in accordance with some embodiments, is believed to proceed more particularly by one or both of the pathways as represented by the Scheme-(2) of FIG. 2 and/or Scheme-(3) of FIG. 3 of the drawings.

With reference to the pathway represented by Scheme-(2) of FIG. 2, in step (a), the lactone isomer represented by Formula (III-A") is converted to Intermediate-(i) in the presence of a catalyst, as will be described in further detail herein. In Scheme-(2), the catalyst, the dienophile represented by Formula (II-A), and the carboxylic acid anhydride represented by Formula (IV) are together present with the lactone isomer represented by Formula (III-A') at the beginning of the reaction, but are depicted as having a more prominent or direct role at different steps throughout the reaction scheme. In step (b), Intermediate-(i) and the dienophile represented by Formula (II-A) react together by what is believed to be a Diels-Alder reaction so as to form Intermediate-(ii). In step (c), which is an aromatization step, Intermediate-(ii) and the carboxylic acid anhydride represented by Formula (IV) together form Intermediate-(iii). During step (c), there is the concurrent formation of $YH_2$. In step (d) intermediate (iii) by intramolecular rearrangement is converted to intermediate (iv) with the loss of one molecule of $H_2O$. In step (e) Intermediate-(iv) and the carboxylic acid anhydride represented by Formula (IV) together form the fused ring indeno compound represented by Formula (I-A).

With reference to the pathway represented by Scheme-(3) of FIG. 3, in step (a) via a Diels-Alder reaction, the lactone isomer represented by Formula (III-A") is converted to Intermediate-(i') in the presence of the dienophile represented by Formula (II-A) and catalyst, as will be described in further detail herein. In Scheme-(3), the catalyst, the dienophile represented by Formula (II-A), and the carboxylic acid anhydride represented by Formula (IV) are together present with the lactone isomer represented by Formula (III-A') at the beginning of the reaction, but are depicted as having a more prominent or direct role at different steps throughout the reaction scheme. In step (b), which is an aromatization step, Intermediate-(i') together with the carboxylic acid anhydride represented by Formula (IV) is converted to Intermediate-(iii). During the course of step (b) of Scheme-(3) there is the concurrent formation of $YH_2$. In step (c), intermediate (iii) by intramolecular rearrangement is converted to intermediate (iv) with the loss of one molecule of $H_2O$. In step (d), Intermediate-(iv) and the carboxylic acid anhydride represented by Formula (IV) together form the fused ring indeno compound represented by Formula (I-A).

With further reference to Scheme-(3) of FIG. 3, and without intending to be bound by any theory, it is believed that the structural isomer of the lactone compound represented by Formula (III-A') also participates, though indirectly, in the illustrated reaction scheme by being converted to the structural isomer represented by Formula (III-A"). For purposes of illustration, and not Intending to be bound by any theory, the lactone structural isomers represented by Formulas (III-A') and (III-A") are believed to rearrange from one to the other as represented by Scheme-4 of FIG. 4, in the presence of acid catalyst (which is not depicted in Scheme-4 of FIG. 4).

Figure 4:
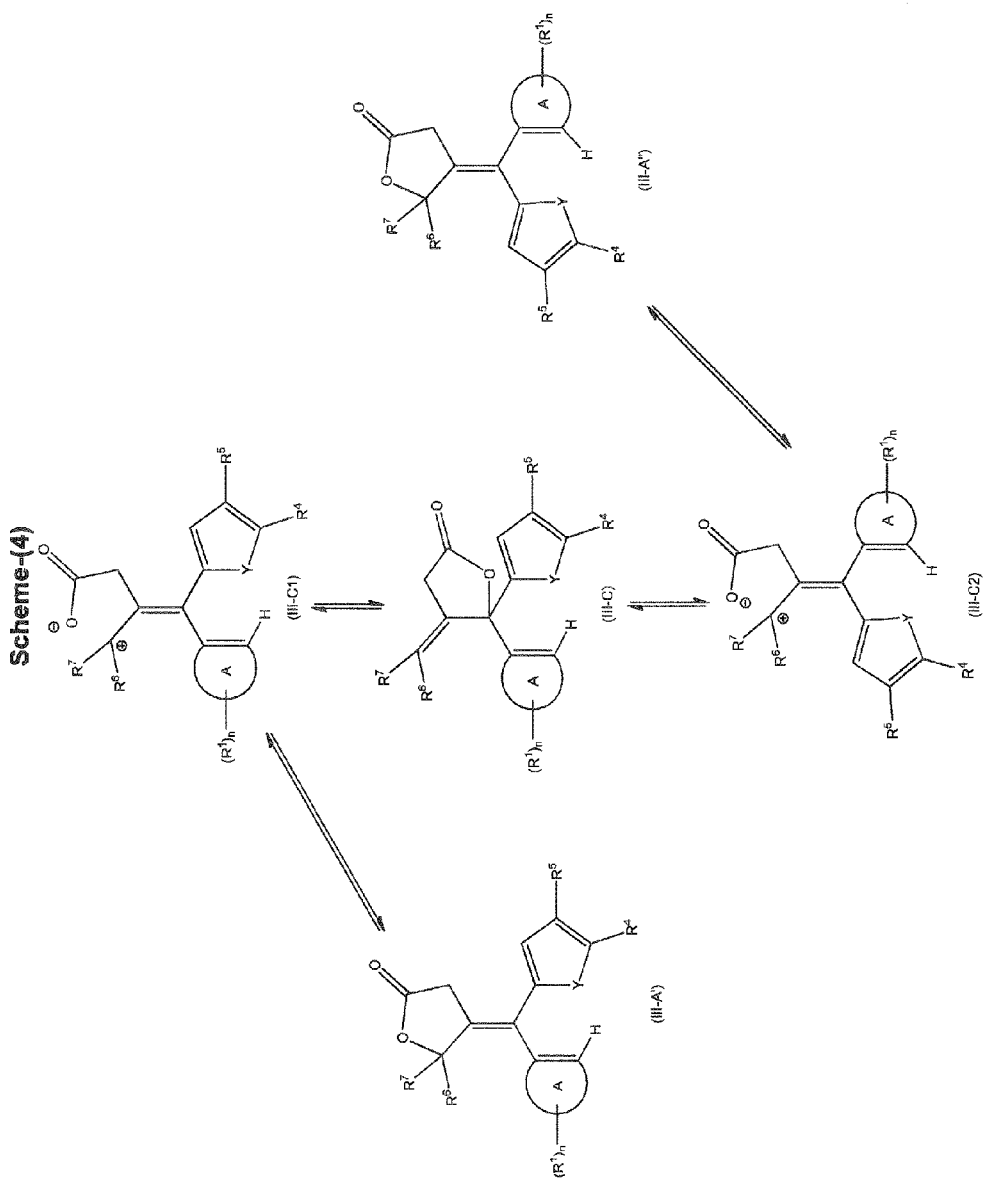
FIG. 4 is an illustrative representative scheme, Scheme-(4), of various equilibriums by which structural isomers of the lactone compounds represented by Formulas (III-A') and (III-A") are converted from one to the other.

With reference to Scheme-4 of FIG. 4, the lactone compound represented by Formula (III-A') is in equilibrium with the open-ringed ionic isomer represented by Formula (III-C1), which is in equilibrium with the spiro-lactone isomer represented by Formula (III-C), which is in equilibrium with the ring-opened ionic isomer represented by Formula (III-C2), which is in equilibrium with the lactone compound represented by Formula (III-A"). As such, by way of the structural isomers represented by Formulas (III-C1), (III-C), and (III-$C_2$), the lactone structural isomers represented by Formulas (III-A') and (III-A") are converted from one to the other. As the lactone structural isomer represented by Formula (III-A") is reacted/consumed in the reaction represented by Scheme-3 of FIG. 3, the lactone structural isomer represented by Formula (III-A') is converted to the structural isomer represented by Formula (III-A") as the effective equilibrium there-between is correspondingly shifted to replace the structural isomer represented by Formula (III-A") as it is consumed in the reaction.

In accordance with some embodiments of the method of the present invention, the catalyst is selected from at least one Lewis acid represented by the following Formula (V) and Formula (VI),

(V)

and

(VI)

Independently for each of Formula (V) and Formula (VI), M represents a metal, y is the valence of the metal, $R_{20}$ for each y is independently selected from hydrocarbyl and halohydrocarbyl, and X for each y is independently selected from halogen. More particularly, and with reference to the Lewis acid represented by Formula (VI), $X^-$ for each y is independently a halogen anion. More particularly, and independently for each of Formula (V) and Formula (VI), $M^{p+}$ represents a metal cation, and y is the valence of the metal cation.

With some further embodiments of the present invention: the metal M of Formula (V) and Formula (VI) is in each case independently selected from Bi, B, Al, Hf, Sc, Cu, Yb, Ti, Sn, Fe, Zn, Ag, Y, In, Nb and Mg; $R_{20}$ of Formula (V) is selected from $C_1$-$C_{10}$ linear or branched alkyl, and $C_1$-$C_{10}$ linear or branched perfluoroalkyl; and X of Formula (VI) is selected from F, Cl, I, and Br.

In accordance with some additional embodiments of the present invention, the catalyst is selected from one or more Lewis acids represented by Formula (V), in which M is Bi, y is 3, and $R_{20}$ is selected from $C_1$-$C_{10}$ linear or branched perfluoroalkyl, such as trifluoromethane.

The catalyst, with some embodiments, is present in an amount of at least 0.001 percent by modes, based on moles of the lactone compound represented by Formula (III-A), such as from 0.001 to 99 percent by moles, or from 0.01 to 30 percent by moles, in each case based on moles of the lactone compound represented by Formula (III-A).

The method of the present invention, in accordance with some embodiments, can be conducted in the presence of a solvent. With some embodiments, the carboxylic acid anhydride represented by Formula (IV) acts as both a solvent and a reactant, such as when an excess of the carboxylic acid anhydride represented by Formula (IV) is present (such as an amount that is in excess of a stoichiometric amount).

With some further embodiments, the method of the present Invention is conducted in the presence of a solvent or a mixture of solvents, and the solvent (other than the carboxylic acid anhydride represented by Formula (IV)) is selected from benzene, toluene, xylene, methylene chloride, 1,2-dichloroethane, $C_1$-$C_{10}$ linear or branched perhaloalkyl, acetonitrile, nitromethane, and combinations thereof.

In accordance with some embodiments, the method of the present invention is conducted in the presence of a solvent or a mixture of solvents that is selected from: (i) the carboxylic acid anhydride represented by Formula (IV); and/or (ii) benzene, toluene, xylene, methylene chloride, 1,2-dichloroethane, $C_1$-$C_{10}$ linear or branched perhaloalkyl, acetonitrile, nitromethane, and combinations thereof.

The method of the present invention can be conducted, with some embodiments, as a batch method, a continuous method, or a combination thereof. With some embodiments, the method of the present invention is conducted at various temperatures, such as at a temperature of at least −80° C., such as from −80° C. to 200° C., or from 20° C. to 140° C. With some embodiments, the method of the present invention is conducted with microwave energy. In accordance with some embodiments, the method of the present invention is conducted over a period of time that is at least sufficient so as to result in formation of a desired amount of fused ring indeno compound, such as from one minutes to 240 hours. The fused ring indeno compounds prepared by the method of the present invention are, with some embodiments, isolated and optionally purified in accordance with art-recognized work-up methods and procedures, including, but not limited to, solvent removal under reduced pressure, solvent extraction, washing, chromatography, recrystallization and combinations thereof.

With the method of the present invention, and in accordance with some embodiments, $R^2$ and $R^3$ of the fused ring indeno compound represented by Formula (I-A) and the dienophile represented by Formula (II-A) in each case together form a cyclic ring, in which case the indeno fused ring compound is represented by the following Formula (I-B),

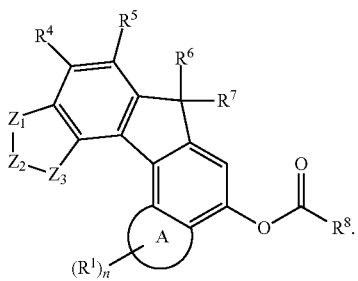
(I-B)

Correspondingly, the dienophile is represented by the following Formula (II-B),

(II-B)

With reference to the indeno fused ring compound represented by Formula (I-B) and the dienophile represented by Formula (II-B), $Z_1$ and $Z_3$ are each independently selected from O, C(O), and $C(R_a)(R_b)$, where $R_a$ and $R_b$ are each independently selected from hydrogen, hydroxyl, and $C_1$-$C_{20}$ linear or branched alkyl, provided that at least one of $Z_1$ and $Z_3$ is C(O). With further reference to the indeno fused ring compound represented by Formula (I-B) and the dienophile represented by Formula (II-B), $Z_2$ is selected from O, S, divalent hydrocarbyl, and N—$R_{13}$, where $R_{13}$ is selected from hydrogen, hydrocarbyl and substituted hydrocarbyl each optionally and independently interrupted with at least one of —O—, —S—, —C(O)—, —C(O)O—, —S(O)—, —$SO_2$—, —N=N—, —N($R_{11}'$)— where $R_{11}'$ is selected from hydrogen, hydrocarbyl or substituted hydrocarbyl, —Si(O$R_8'$)$_w$($R_8'$)$_t$—, where w and t are each independently selected from 0 to 2, provided that the sum of w and t is 2, and each $R_8'$ is independently selected from hydrogen, hydrocarbyl and substituted hydrocarbyl, and combinations of two or more thereof.

Alternatively, and with further reference to the indeno fused ring compound represented by Formula (I-B) and the dienophile represented by Formula (II-B), and with some embodiments, $Z_2$ defines an optionally substituted fused ring. As used herein, the term "$Z_2$ defines an optionally substituted fused ring," means that $Z_2$ defines an optionally substituted fused ring that is bonded to both $Z_1$ and $Z_3$. In accordance with some further embodiments, the term "$Z_2$ defines an optionally substituted fused ring," does not include spiro compounds. For purposes of non-limiting illustration, and in accordance with some embodiments, when $Z_2$ defines an optionally substituted fused ring, the indeno fused ring compound represented by Formula (I-B) and the dienophile represented by Formula (I-B) are in each case respectively represented by the following Formula (I-B') and Formula (II-B'):

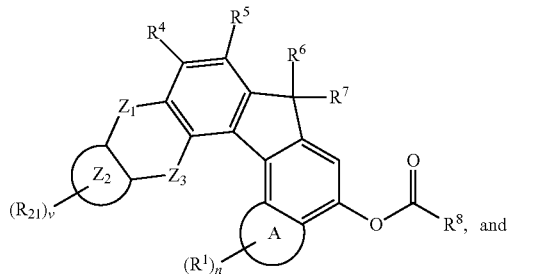
(I-B')

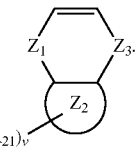
(II-B')

With reference to Formula (I-B') and Formula (II-B'): Ring-$Z_2$ is selected from cyclocalkyl, heterocycloalkyl, aryl, and heteroaryl; v is selected from 1 to 8; and $R_{21}$ for each v is independently selected from hydrogen, cyano, nitro, halogen (such as, F, Cl, Br, and I), hydrocarbyl, substituted hydrocarbyl, and perhalohydrocarbyl. With some embodiments, Ring-$Z_2$ is selected from $C_6$-cycloalkyl (having 6 carbon atoms in the cycloalkyl ring) and $C_6$-aryl (having 6 carbon atoms in the aryl ring).

With some embodiments of the present invention, $Z_1$ and $Z_2$ of the various compounds of the method of the present invention, such as the fused ring indeno compound represented by Formulas (I-B), and the dienophile represented by Formula (II-B), are each C(O).

With reference to the fused ring indeno compound represented by Formula (I-B) and the dienophile represented by Formula (II-B), and in accordance with some embodiments, $Z_2$ is N—$R_{13}$, and $R_{13}$ is, or is converted to, a group L represented by the following Formula (VII), and optionally at least one $R^1$ independently for each n, is selected from (or is converted to) the group L represented by the following Formula (VII),

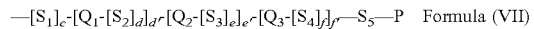
—[$S_1$]$_c$-[$Q_1$-[$S_2$]$_d$]$_{d'}$-[$Q_2$-[$S_3$]$_e$]$_{e'}$-[$Q_3$-[$S_4$]$_f$]$_{f'}$—$S_5$—P   Formula (VII)

One or more groups L represented by Formula (VII) can be introduced into the fused ring indeno compound during synthesis thereof and/or after synthesis thereof. With some embodiments, when $Z_2$ of the dienophile represented by Formula (II-B) is N—$R_{13}$, $R_{13}$ is the group L represented by Formula (VII). In accordance with some further embodiments, when $Z_2$ of the dienophile represented by Formula (II-B) is N—$R_{13}$, $R_{13}$ is or is converted to a precursor of the group L represented by Formula (VII), in which case $R_{13}$ is converted to the group L after formation of the fused ring indeno compound, with some embodiments.

With reference to Formula (VII), and in accordance with some embodiments, (a) $Q_1$, $Q_2$, and $Q_3$ for each occurrence, are independently selected from a divalent group selected from optionally substituted aryl, optionally substituted heteroaryl, optionally substituted cycloalkyl, and optionally substituted heterocycloalkyl. The aryl substituents, heteroaryl substituents, cycloalkyl substituents, and heterocycloalkyl substituents are, with some embodiments, each independently selected from P (as described in further detail below), liquid crystal mesogens, halogen, poly($C_1$-$C_{18}$ alkoxy), $C_1$-$C_{18}$ alkoxycarbonyl, $C_1$-$C_{18}$ alkylcarbonyl, $C_1$-$C_{18}$ alkoxycarbonyloxy, aryloxycarbonyloxy, perfluoro($C_1$-$C_{18}$)alkoxy, perfluoro($C_1$-$C_{18}$)alkoxycarbonyl, perfluoro($C_1$-$C_{18}$)alkylcarbonyl, perfluoro($C_1$-$C_{18}$)alkylamino, di-(perfluoro($C_1$-$C_{18}$)alkyl)amino, perfluoro($C_1$-$C_{18}$)alkylthio, $C_1$-$C_{18}$ alkylthio, $C_1$-$C_{18}$ acetyl, $C_3$-$C_{10}$ cycloalkyl, $C_3$-$C_{10}$ cycloalkoxy, straight-chain $C_1$-$C_{18}$ alkyl, and branched $C_1$-$C_{18}$ alkyl. The straight-chain $C_1$-$C_{18}$ alkyl and branched $C_1$-$C_{18}$ alkyl, with some embodiments, are mono-substituted with a group selected from cyano, halogen, and $C_1$-$C_{18}$ alkoxy. Alternatively, and with some embodiments, the straight-chain $C_1$-$C_{18}$ alkyl and branched $C_1$-$C_{18}$ alkyl are poly-substituted with at least two groups independently selected from halogen, -M(T)$_{(v-1)}$ and -M(OT)$_{(v-1)}$, in which M is chosen from aluminum, antimony, tantalum, titanium, zirconium and silicon, T is chosen from organofunctional radicals, organofunctional hydrocarbon radicals, aliphatic hydrocarbon radicals and aromatic hydrocarbon radicals, and v is the valence of M.

With further reference to Formula (VII), and in accordance with some further embodiments, (b) c, d, e, and f are each independently chosen from an integer of 1 to 20; and each $S_1$, $S_2$, $S_3$, $S_4$, and $S_5$ is independently chosen for each occurrence from a spacer unit selected from (i), (ii), and (iii) as described as follows. With some embodiments, each $S_1$, $S_2$, $S_3$, $S_4$, and $S_5$ is independently chosen for each occurrence from a spacer unit selected from (i) optionally substituted alkylene, optionally substituted haloalkylene, —Si(CH$_2$)$_g$—, and —(Si[(CH$_3$)$_2$]O)$_h$—, wherein g for each occurrence is independently chosen from an integer from 1 to 20; h for each occurrence is independently chosen from an integer from 1 to 16; and said substitutes for the alkylene and haloalkylene are independently selected from $C_1$-$C_{18}$ alkyl, $C_3$-$C_{10}$ cycloalkyl and aryl. With some further embodiments, each $S_1$, $S_2$, $S_3$, $S_4$, and $S_5$ is independently chosen for each occurrence from a spacer unit selected from (ii) —N(Z)—, —C(Z)=C(Z)—, —C(Z)=N—, —C(Z')$_2$—C(Z')$_2$—, and a single bond, wherein Z for each occurrence is independently selected from hydrogen, $C_1$-$C_{18}$ alkyl, $C_3$-$C_{10}$ cycloalkyl and aryl, and Z' for each occurrence is independently selected from $C_1$-$C_{18}$ alkyl, $C_3$-$C_{10}$ cycloalkyl and aryl. With some additional embodiments, each $S_1$, $S_2$, $S_3$, $S_4$, and $S_5$ is independently chosen for each occurrence from a spacer unit selected from (iii) —O—, —C(=O)—, —C≡C—, —N=N—, —S—, —S(=O)—, —S(=O)$_2$—, —(O=)S(=O)O—, —O(O=)S(=O)O— and straight-chain or branched $C_1$-$C_{24}$ alkylene residue, said $C_1$-$C_{24}$ alkylene residue being unsubstituted, mono-substituted by cyano or halogen, or poly-substituted by halogen. With further reference to each of $S_1$, $S_2$, $S_3$, $S_4$, and $S_5$, and with some embodiments, there is the proviso that when two spacer units comprising heteroatoms are linked together the spacer units are linked so that heteroatoms are not directly linked to each other. There is a further proviso, with some embodiments, that each bond between $S_1$ and the nitrogen atom of N—$R_{13}$ of the fused ring indeno compound represented by Formula (I-B) and of the dienophile represented by Formula (II-B) is in each case free of two heteroatoms linked together, and the bond between $S_5$ and P is free of two heteroatoms linked to each other.

With further reference to Formula (VII), and in accordance with some further embodiments, (c) P for each occurrence is independently selected from hydroxy, amino, $C_2$-$C_{18}$ alkenyl, $C_2$-$C_{18}$ alkynyl, azido, silyl, siloxy, siylhydride, (tetrahydro-2H-pyran-2-yl)oxy, thio, isocyanato, thioisocyanato, acryloyloxy, methacryloyloxy, 2-(acryloyloxy)ethylcarbamyl, 2-(methacryloyloxy)ethylcarbamyl, aziridinyl, alyloxycarbonyloxy, epoxy, carboxylic acid, carboxylic ester, acryloylamino, methacryloylamino, aminocarbonyl, $C_1$-$C_{18}$ alkyl aminocarbonyl, aminocarbonyl($C_1$-$C_{18}$) alkyl, $C_1$-$C_{18}$ alkyloxycarbonyloxy, halocarbonyl, hydrogen, aryl, hydroxy($C_1$-$C_{18}$)alkyl, $C_1$-$C_{18}$ alkyl, $C_1$-$C_{18}$ alkoxy, amino($C_1$-$C_{18}$)alkyl, $C_1$-$C_{18}$ alkylamino, di-($C_1$-$C_{18}$) alkylamino, $C_1$-$C_{18}$ alkyl($C_1$-$C_{18}$)alkoxy, $C_1$-$C_{18}$ alkoxy($C_1$-$C_{18}$)alkoxy, nitro, poly($C_1$-$C_{18}$)alkyl ether, ($C_1$-$C_{18}$)alkyl($C_1$-$C_{18}$)alkoxy($C_1$-$C_{18}$)alkyl, polyethyleneoxy, polypropyleneoxy, ethylene, acryloyl, acryloyloxy($C_1$-$C_{18}$) alkyl, methacryloyl, methacryloyloxy($C_1$-$C_{18}$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato($C_1$-$C_{18}$)alkyl, itaconic acid ester, vinyl ether, vinyl ester, a styrene derivative, main-chain and side-chain liquid crystal polymers, siloxane derivatives, ethyleneimine derivatives, maleic acid derivatives, maleimide derivatives, fumaric acid derivatives, unsubstituted cinnamic acid derivatives, cinnamic acid derivatives that are substituted with at least one of methyl, methoxy, cyano and halogen, and substituted or unsubstituted chiral or non-chiral monovalent or divalent groups chosen from steroid radicals, terpenoid radicals, alkaloid radicals and mixtures thereof, wherein the substituents are independently chosen from $C_1$-$C_{18}$ alkyl, $C_1$-$C_{18}$ alkoxy, amino, $C_3$-$C_{10}$ cycloalkyl, $C_1$-$C_{18}$ alkyl($C_1$-$C_{18}$)alkoxy, fluoro($C_1$-$C_{18}$)alkyl, cyano, cyano($C_1$-$C_{18}$)alkyl, cyano($C_1$-$C_{18}$)alkoxy or mixtures thereof, or P is a structure having from 2 to 4 reactive groups, or P is an unsubstituted or substituted ring opening metathesis polymerization precursor, or P is a substituted or unsubstituted photochromic compound.

With additional reference to Formula (VII), and in accordance with some embodiments, (d) d', e' and f' are each independently chosen from 0, 1, 2, 3, and 4, provided that the sum of d'+e'+f is at least 1.

In accordance with some embodiments, for the group L represented by Formula (VII), (a) $Q_1$, $Q_2$, and $Q_3$ for each occurrence, are independently selected from optionally substituted aryl and optionally substituted cycloalkyl.

With further reference to Formula (VII), and in accordance with some embodiments, (b) each $S_1$, $S_2$, $S_3$, $S_4$, and $S_5$ of Formula (VII) is independently chosen for each occurrence from a spacer unit selected from (ii) and (iii) as described as follows. Each $S_1$, $S_2$, $S_3$, $S_4$, and $S_5$ of Formula (VII), with some embodiments, is independently chosen for each occurrence from a spacer unit selected from (ii) —N(Z)—, —C(Z)=C(Z)—, —C(Z)=N—, —C(Z')$_2$—C(Z')$_2$—, and a single bond, wherein Z for each occurrence is independently selected from hydrogen, $C_1$-$C_8$ alkyl, $C_3$-$C_6$ cycloalkyl and aryl, and Z' for each occurrence is independently selected from $C_1$-$C_8$ alkyl, $C_3$-$C_6$ cycloalkyl and aryl. Each $S_1$, $S_2$, $S_3$, $S_4$, and $S_5$ of Formula (VII), with some further embodiments, is independently chosen for each occurrence from a spacer unit selected from (iii) —O—, —C(=O)—, —C≡C—, —N=N—, —S—, —S(=O)—, and straight-chain or branched $C_1$-$C_{12}$ alkylene residue, said $C_1$-$C_{12}$ alkylene residue being unsubstituted, mono-substituted by cyano or halogen, or poly-substituted by halogen.

In accordance with some additional embodiments, for the group L represented by Formula (VII), (c) P for each occurrence is independently selected from hydrogen, hydroxy, amino, $C_2$-$C_8$ alkenyl, $C_2$-$C_8$ alkynyl, acryloyloxy, methacryloyloxy, 2-(acryloyloxy)ethylcarbamyl, 2-(methacryloyloxy)ethylcarbamyl, epoxy, carboxylic acid, carboxylic ester, acryloylamino, methacryloylamino, aminocarbonyl, $C_1$—C alkyl aminocarbonyl, aminocarbonyl($C_1$-$C_8$) alkyl, $C_1$-$C_8$ alkyloxycarbonyloxy, halocarbonyl, aryl, hydroxy($C_1$-$C_8$)alkyl, $C_1$—C alkyl, $C_1$-$C_8$ alkoxy, amino ($C_1$-$C_8$)alkyl, $C_1$-$C_8$ alkylamino, di-($C_1$-$C_8$)alkylamino, $C_1$-$C_8$ alkyl($C_1$-$C_8$)alkoxy, $C_1$-$C_8$ alkoxy($C_1$-$C_8$)alkoxy, nitro, poly($C_1$-$C_8$)alkyl ether, ($C_1$-$C_8$)alkyl($C_1$-$C_8$)alkoxy ($C_1$-$C_8$)alkyl, polyethyleneoxy, polypropyleneoxy, ethylene, acryloyl, acryloyloxy($C_1$-$C_8$)alkyl, methacryloyl, methacryloyloxy($C_1$-$C_8$)alkyl, 2-chloroacryloyl, 2-phenylacryloyl, acryloyloxyphenyl, 2-chloroacryloylamino, 2-phenylacryloylaminocarbonyl, oxetanyl, glycidyl, cyano, isocyanato ($C_1$-$C_{18}$)alkyl, itaconic acid ester, vinyl ether, and vinyl ester.

In accordance with some further additional embodiments, for the group L represented by Formula (VII), (b) each $S_1$, $S_2$, $S_3$, $S_4$, and $S_5$ is independently chosen for each occurrence from a spacer unit selected from: (ii) —N(Z)—, —C(Z)=C(Z)—, and a single bond, wherein Z for each occurrence is independently selected from hydrogen, $C_1$-$C_8$ alkyl, $C_3$-$C_6$ cycloalkyl and aryl; and (iii) —O—, —C(=O)—, —C≡C—, and straight-chain or branched $C_1$-$C_6$ alkylene residue, said $C_1$-$C_6$ alkylene residue being unsubstituted, mono-substituted by cyano or halogen, or poly-substituted by halogen.

In accordance with some additional further embodiments, for the group L represented by Formula (VII), (c) P for each occurrence is independently selected from hydrogen, hydroxy, amino, $C_2$-$C_8$ alkenyl, $C_2$-$C_8$ alkynyl, and aryl.

In accordance with some embodiments of the present invention, each group L as represented by Formula (VII) is independently selected from the following non-limiting groups:

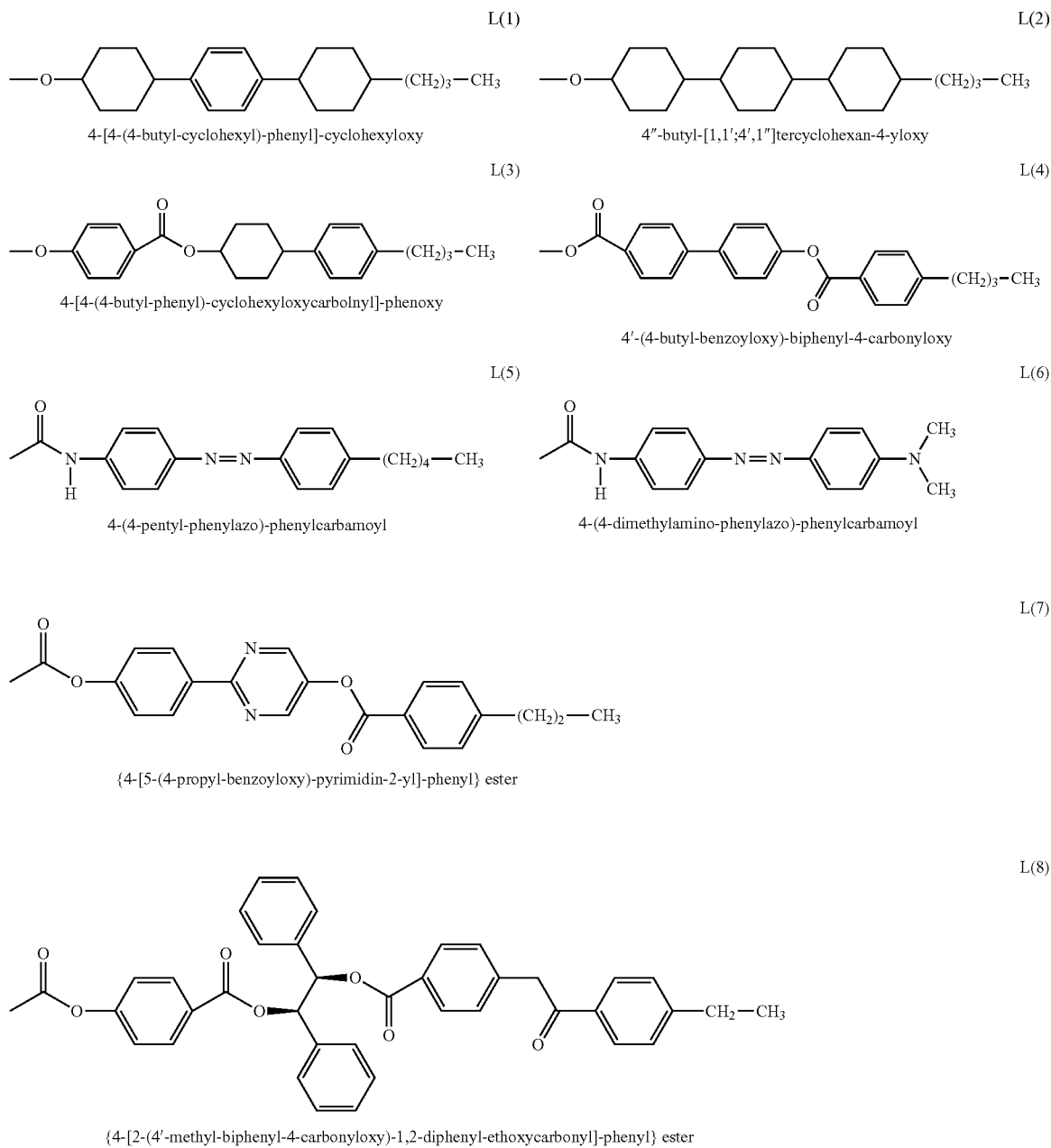

-continued

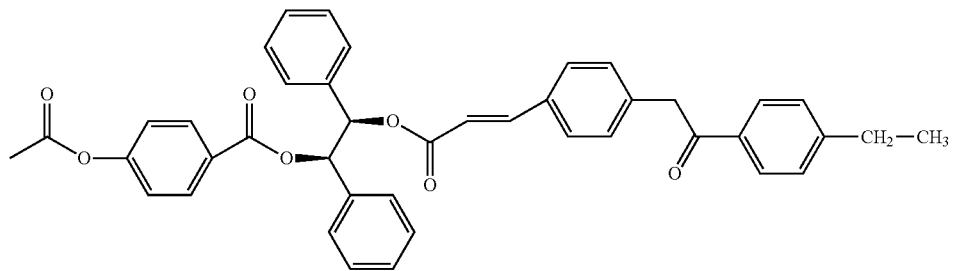

[4-(1,2-diphenyl-2-{3-[4-(4-propyl-benzoyloxy)-phenyl]-acryloyloxy}-ethoxycarbonyl)-phenyl] ester
L(9)

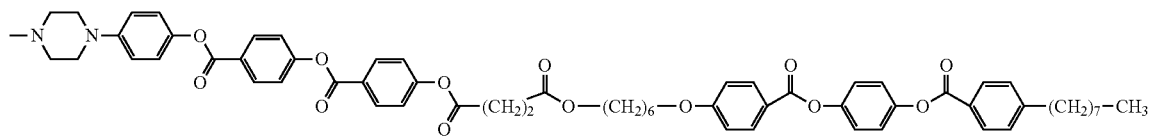

4-[4-(4-{4-[3-(6-{4-[4-(4-nonyl-benzoyloxy)-phenoxycarbonyl]-phenoxy}-hexyloxycarbonyl)-propionyloxy]-benzoyloxy}-benzoyloxy)-phenyl]-piperazin-1-yl
L(10)

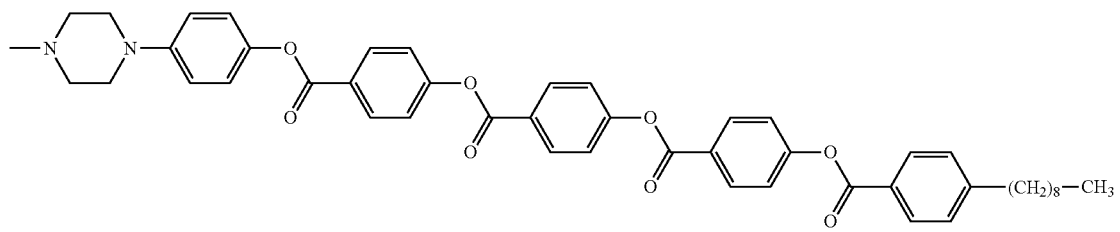

{4-[4-(4-{4-[4-(4-nonyl-benzoyloxy)-benzoyloxy]-benzoyloxy}-benzoyloxy)-phenyl]-piperazin-1-yl}
L(11)

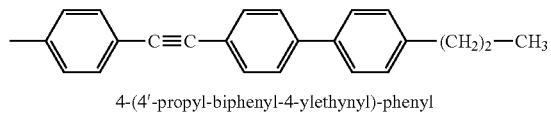

4-(4'-propyl-biphenyl-4-ylethynyl)-phenyl
(L12)

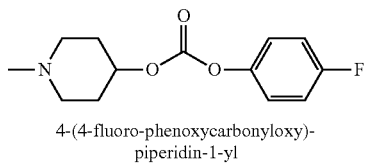

4-(4-fluoro-phenoxycarbonyloxy)-piperidin-1-yl
L(13)

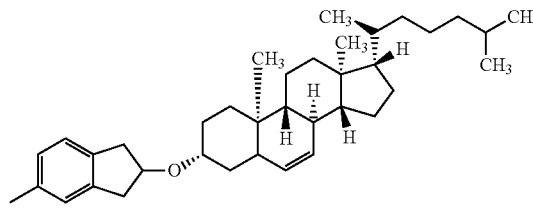

2-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxy]-indan-5-yl
(L14)

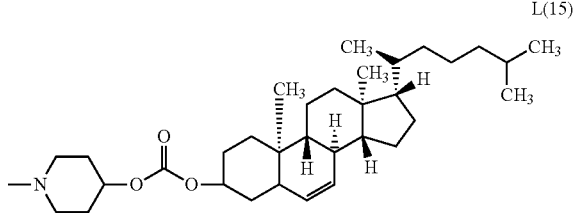

4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-piperidin-1-yl
L(15)

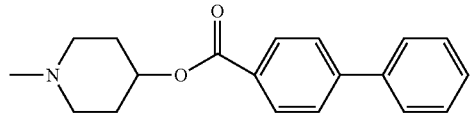

4-(biphenyl-4-carbonyloxy)-piperin-1-yl
L(16)

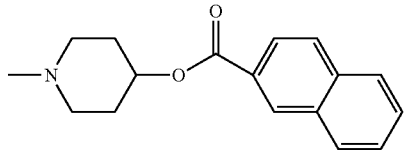

4-(naphthalene-2-carbonyloxy)-piperidin-1-yl
L(17)

-continued

L(18)

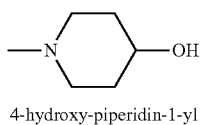

4-hydroxy-piperidin-1-yl

L(19)

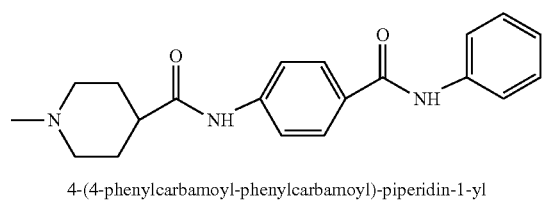

4-(4-phenylcarbamoyl-phenylcarbamoyl)-piperidin-1-yl

L(20)

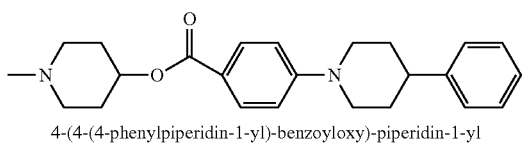

4-(4-(4-phenylpiperidin-1-yl)-benzoyloxy)-piperidin-1-yl

L(21)

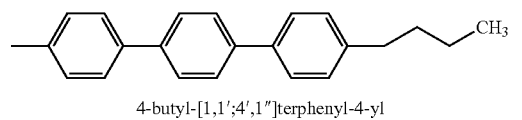

4-butyl-[1,1′;4′,1″]terphenyl-4-yl

L(22)

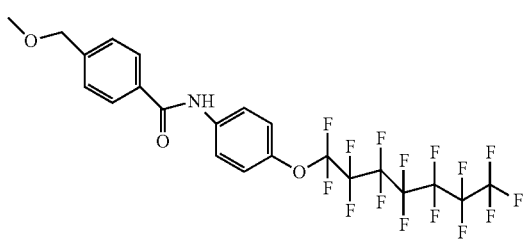

4-(4-pentadecafluoroheptyloxy-phenylcarbamoyl)-benzyloxy

L(23)

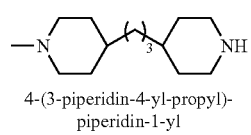

4-(3-piperidin-4-yl-propyl)-piperidin-1-yl

L(24)

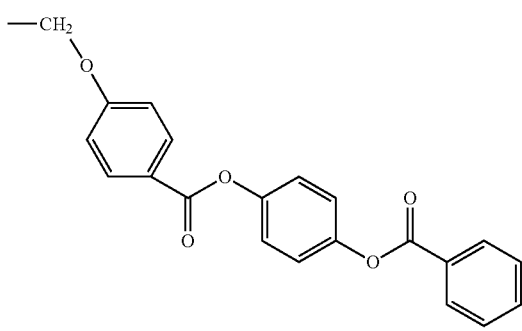

4-(4-{4-[17-(1,5-dimethyl-hexyl)-10,13-dimethyl-2,3,4,7,8,9,10,11,12,13,14,15,16,17-tetradecahydro-1H-cyclopenta[a]phenanthren-3-yloxycarbonyloxy]-benzoyloxy}-phenoxycarbonyl)-phenoxymethyl

L(25)

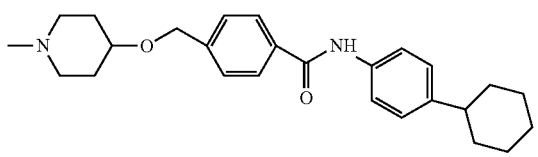

4-[4-(4-cyclohexyl-phenylcarbamoyl)-benzyloxy]-piperidin-1-yl

L(26)

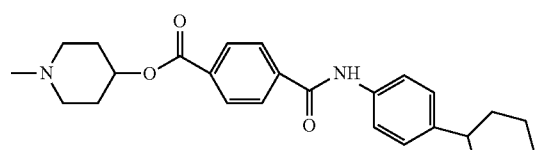

4-[4-(4-cyclohexyl-phenylcarbamoyl)-benzyloxy]-piperidin-1-yl

L(27)

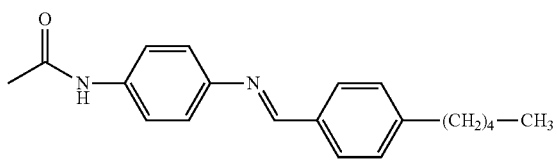

N-{4-[(4-pentyl-benzylidene)-amino]-phenyl}-acetamidyl

L(28)

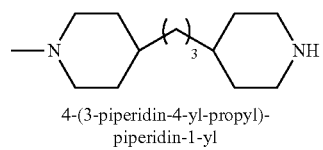

4-(3-piperidin-4-yl-propyl)-piperidin-1-yl

-continued

L(29)

4-(4-hexyloxy-bezoloxy)-piperidin-1-yl]

L(30)

4-(4'-hexyloxy-biphenyl-4-carbonyloxy)-piperidin-1-yl

L(31)

4-(4-butyl-phenylcarbamoyl)-piperidin-1-yl

L(32a)

1-methyl-4-((4'-(((1-methylpiperidin-4-yl)oxy)carbonyl)-
[1,1'-biphenyl]-
4-carbonyl)oxy)piperidin-1-yl L(32b)

bis(1-yl-piperidin-4-yl) [1,1'-biphenyl]-4,4'-dicarboxylate
(which links two
separate photochromic PC groups)

L(33)

4-(4-(9-(4-butylphenyl)-2,4,8,10-tetraoxaspiro
[5.5]undec-3-yl)phenyl)piperazin-1-yl

L(34)

4-(6-(4-butylphenyl)carbonyloxy-(4,8-dioxabicyclo[3.3.0]oct-2-
yl))oxycarbonyl)pheny

L(35)

1-{4-[5-(4-butyl-phenyl)-[1,3]dioxan-2-yl]-
phenyl}-4-methyl-piperzain-1-yl

L(36)

4-(7-(4-propylphenylcarbonyloxy)bicyclo[3.3.0]
oct-2-yl)oxycarbonyl)phenyl

L(37)

4-[17-(1,5-dimethyl-hexyl)-10,13-dimethyl-
2,3,4,7,8,9,10,11,12,13,14,15,16,17-tetradecahydro-
1H-cyclopenta[a]phenanthren-3-yloxycarbonyloxy L(a)

L(b)

-continued
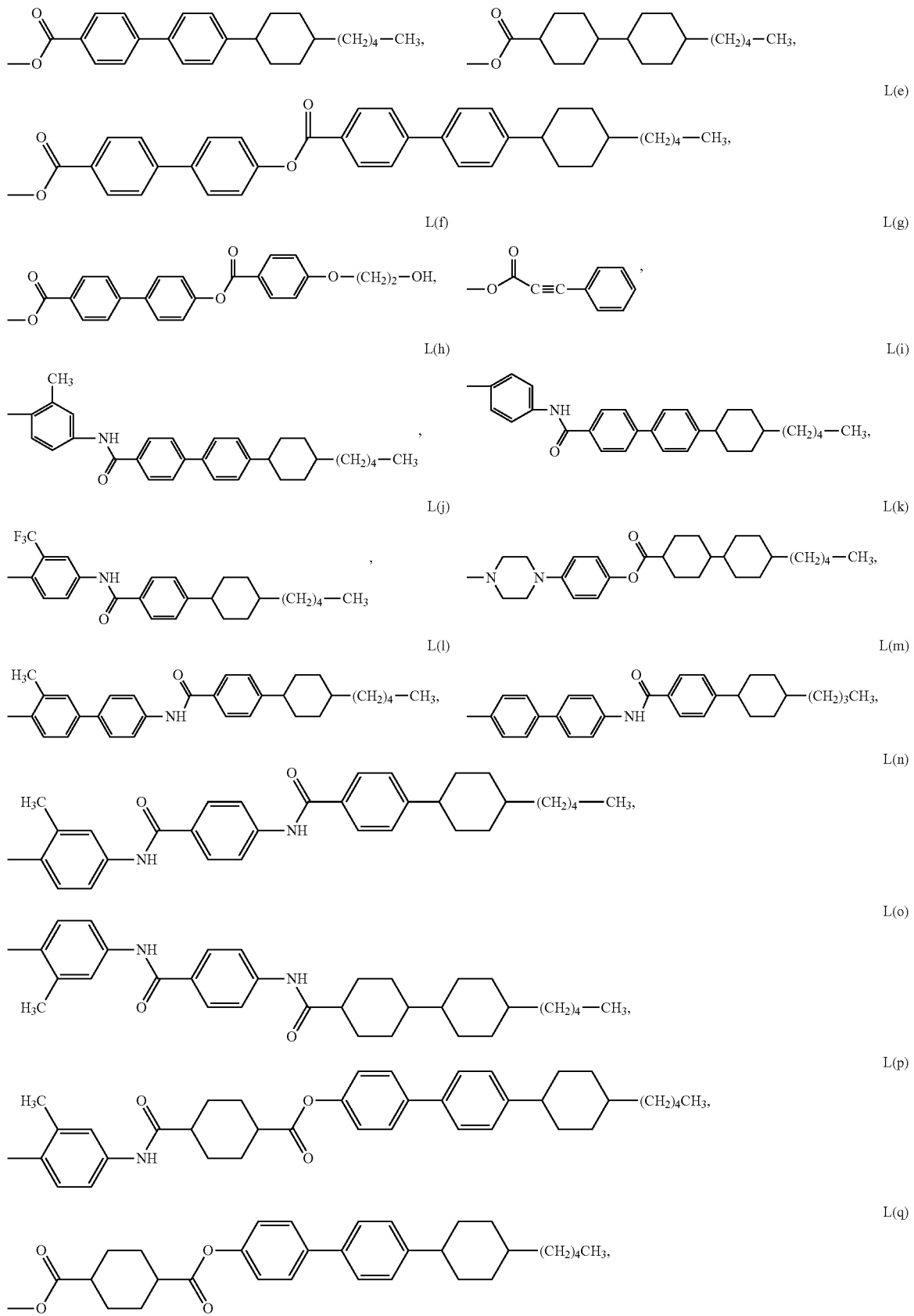

-continued
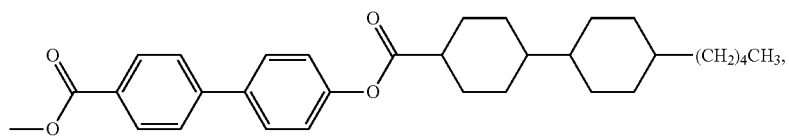
L(r)
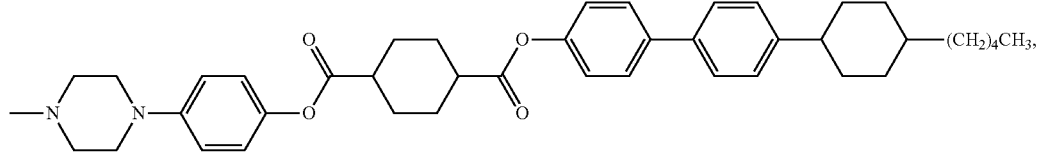
L(s)
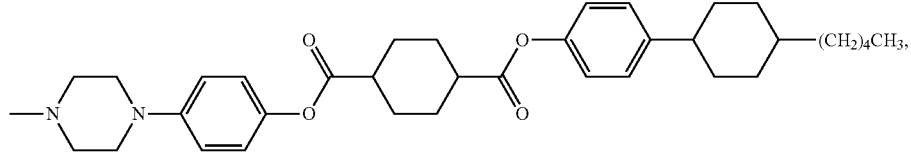
L(t)
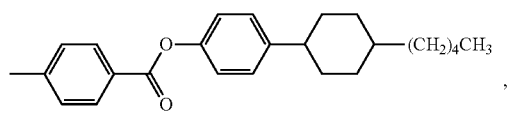
L(u)
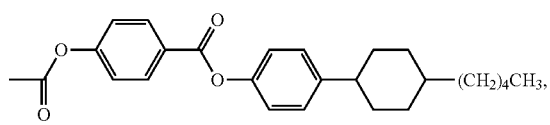
L(v)
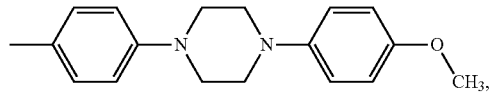
L(w)
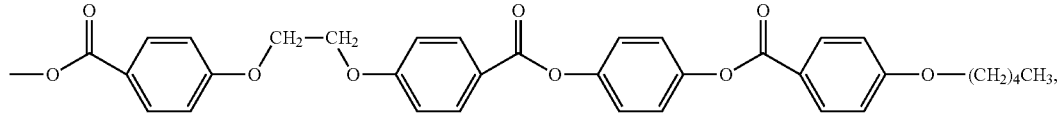
L(x)
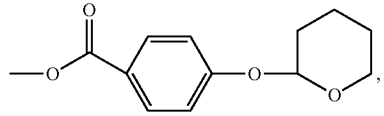
L(y)
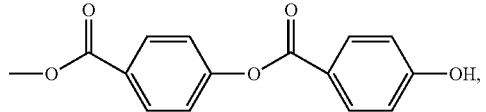
L(z)
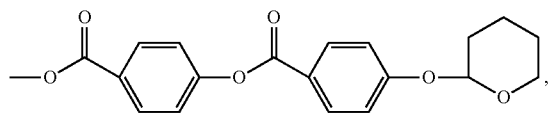
L(aa)
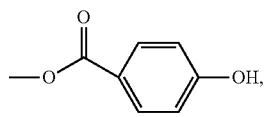
L(ab)
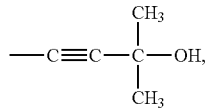
L(ac)
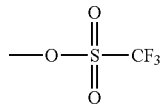
L(ad)
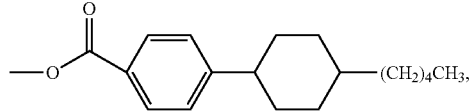
L(ae)
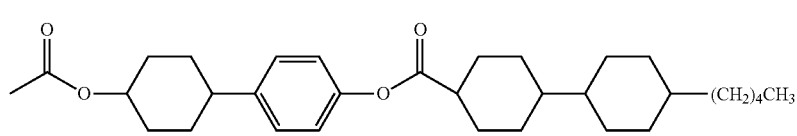
L(af)

L-DC-(a) (4-trans-(4-pentylcyclohexyl)benzamido)phenyl,
L-DC-(b) (4-(4'-trans-(4-pentylcyclohexyl)phenoxy)carbonyl)phenyl,
L-DC-(c) 4-(4-(4-trans-(4-pentylcyclohexyl)phenyl)benzamido)phenyl,
L-DC-(d) 4-((trans-(4'-pentyl-[1,1'-bi(cyclohexan)]-4-yl)oxy)carbonyl)phenyl,
L-DC-(e) 4-(4'-(4-pentylcyclohexyl)-[1,1'-biphenyl]-4-ylcarboxamido)phenyl,
L-DC-(f) 4-(4'-(4-pentylcyclohexyl)-[1,1'-biphenyl]-4-ylcarboxamido)benzamido,
L-DC-(g) 4-(4'-(4-pentylcyclohexyl)-[1,1'-biphenyl]-4-carbonyl)piperazin-1-yl,
L-DC-(h) 4-(4'-(4-trans-(4-phentylcyclohexyl)phenyl)benzamido)-2-(trifluoromethyl)phenyl,
L-DC-(i) 2-methyl-4-trans-(4-((4'-trans-(4-pentylcyclohexyl)biphenyl-4-yloxy)carbonyl)cyclohexanecarboxamido)phenyl,
L-DC-(j) 4'-(4'-pentylbi(cyclohexane-4-)carbonyloxy)biphenylcarbonyloxy,
L-DC-(k) 4-(((3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yloxy)carbonyl)piperazin-1-yl, and
L-DC-(l) 4-((S)-2-methybutoxy)phenyl)-10-(4-(((3R,3aS,6S,6aS)-6-(4'-trans-(4-pentylcyclohexyl)biphenylcarbonyloxy)hexahydrofuro[3,2b]furan-3-yloxy)carbonyl)phenyl, With regard to the above non-limiting examples of L groups, there is the proviso that that $R_{13}$ of N—$R_{13}$ is only selected from L(5), L(6), L(7), L(8), L(9), L(12), L(14), L(21), L(24), L(27), L(34), L(36), L(h), L(i), L(j), L(l), L(m), L(n), L(n), L(o), L(p), L(u), L(v), L(w), L(ac), L(ae), L(af), L-DC-(a), L-DC-(b), L-DC-(c), L-DC-(d), L-DC-(e), L-DC-(h), L-DC-(i), and L-DC-(l).

In accordance with some embodiments, the indeno fused ring compound represented by Formula (I-B), after formation thereof, can be subjected to one or more additional chemical reactions for purposes of modifying $R_{13}$ (when group $Z_2$ is N—$R_{13}$), such that $R_{13}$ is, or is converted to, an L group (or group L) as described previously herein with reference to Formula (VII). Examples of additional chemical reactions that the indeno fused ring compound represented by Formula (I-B) can be subjected to include, but are not limited to, palladium-catalyzed cross couplings, etherifications, esterifications, amidations, and condensations.

With reference to the fused ring indeno compound represented by Formula (I-A) and the lactone compound represented by Formula (III-A), Ring-A is selected from aryl.

With some embodiments, $R^1$ for the fused ring indeno compound represented by Formula (I-A) and the lactone compound represented by Formula (III-A) for each n is independently selected from, hydrogen, halogen selected from bromo, iodo, fluoro and chloro; $C_1$-$C_{20}$ linear or branched alkyl; $C_3$-$C_{10}$ cycloalkyl; and substituted or unsubstituted phenyl, in which the phenyl substituents being selected from halogen, halo($C_1$-$C_{20}$)alkyl, $C_1$-$C_{20}$ alkyl or $C_1$-$C_{20}$ alkoxy.

With some further embodiments, $R^1$ for Formula (I-A) and Formula (III-A), for each n is independently selected from, —O—$R_{10}$' or —S—$R_{10}$', wherein each $R_{10}$' independently is hydrogen, $C_1$-$C_{20}$ alkyl, phenyl($C_1$-$C_{20}$)alkyl, mono($C_1$-$C_{20}$)alkyl substituted phenyl($C_1$-$C_{20}$)alkyl, mono ($C_1$-$C_{20}$)alkoxy substituted phenyl($C_1$-$C_{20}$)alkyl, ($C_1$-$C_{20}$) alkoxy($C_2$-$C_{20}$)alkyl, $C_3$-$C_{10}$ cycloalkyl, or mono($C_1$-$C_{20}$) alkyl substituted $C_3$-$C_{10}$ cycloalkyl.

With some additional embodiments, $R^1$ for Formula (I-A) and Formula (III-A), for each n is independently selected from, —N($R_{11}$')$R_{12}$' or —C(O)—N($R_{11}$')($R_{12}$'), wherein $R_{11}$' and $R_{12}$' are each independently hydrogen, $C_1$-$C_{20}$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$-$C_{20}$ alkylaryl, $C_3$-$C_{10}$ cycloalkyl, $C_4$-$C_{20}$ bicycloalkyl, $C_5$-$C_{20}$ tricycloalkyl or $C_1$-$C_{20}$ alkoxyalkyl, wherein the aryl group (of, for example, the $C_1$-$C_{20}$ alkoxyalkyl) is phenyl or naphthyl, or $R_{11}$' and $R_{12}$' come together with the nitrogen atom to form a $C_3$-$C_{20}$ hetero-bicycloalkyl ring or a $C_4$-$C_{20}$ hetero-tricycloalkyl ring.

With some additional further embodiments, $R^1$ for Formula (I-A) and Formula (III-A), for each n is independently selected from, a nitrogen containing ring represented by the following graphic formula XIIA,

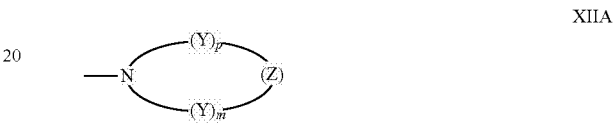

XIIA

With reference to Formula (XIIA), each —Y— is independently chosen for each occurrence from —$CH_2$, —CH($R_{13}$')—, —C($R_{13}$')$_2$—, —CH(aryl)-, —C(aryl)$_2$-, and —C($R_{13}$')(aryl)-, and Z is —Y—, —O—, —S—, —NH—, —N($R_{13}$')—, or —N(aryl)-, wherein each $R_{13}$' is independently $C_1$-$C_{20}$ alkyl, each aryl is independently phenyl or naphthyl, m is an integer 1, 2 or 3, and p is an integer 0, 1, 2, or 3 and provided that when p is 0, Z is —Y—.

With some further additional embodiments, $R^1$ for Formula (I-A) and Formula (III-A), for each n is independently selected from, a group represented by one of the following graphic formulas XIIB or XIIC,

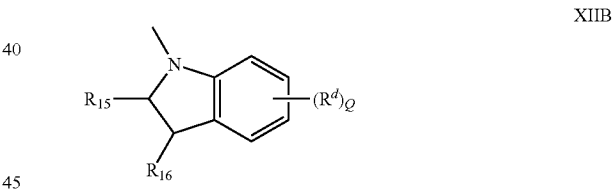

XIIB

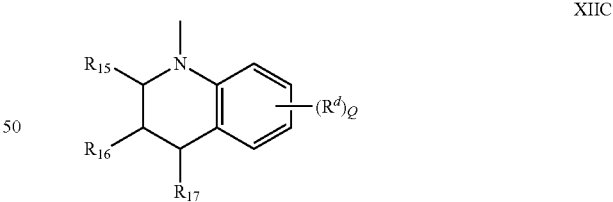

XIIC

With reference to Formulas (XIIB) and (XIIC), $R_{15}$, $R_{16}$, and $R_{17}$ are each independently hydrogen, $C_1$-$C_{20}$ alkyl, phenyl, or naphthyl, or the groups $R_{15}$ and $R_{16}$ together form a ring of 5 to 8 carbon atoms and each $R^d$ is independently for each occurrence selected from $C_1$-$C_{20}$ alkyl, $C_1$-$C_{20}$ alkoxy, fluoro or chloro, and Q is an integer 0, 1, 2, or 3.

The $R^1$ group, for Formula (I-A) and Formula (III-A), for each n is independently selected from, with some embodiments, unsubstituted, mono-, or di-substituted $C_4$-$C_{18}$ spirobicyclic amine, or unsubstituted, mono-, and di-substituted $C_4$-$C_{18}$ spirotricyclic amine, wherein said substituents are independently aryl, $C_1$-$C_{20}$ alkyl, $C_1$-$C_{20}$ alkoxy, or phenyl($C_1$-$C_{20}$)alkyl.

In accordance with some alternative embodiments, two adjacent $R^1$ groups together form a group represented by one of XIID and XIIE:

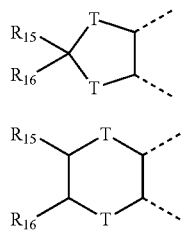

XIID

XIIE

With reference to Formula XIID and XIIE, T and T' are each independently oxygen or the group —$NR_{11}'$—, where $R_{11}'$, $R_{15}$, and $R_{16}$ are as set forth above.

In accordance with some embodiments, $R^2$ and $R^3$, for Formula (I-A) and Formula (II-A), are each independently selected from: hydrogen; cyano; nitro; halogen selected from F, Cl, Br, and I; $C_1$-$C_{20}$ linear or branched alkyl; $C_1$-$C_{20}$ linear or branched perfluoroalkyl; $C_3$-$C_{10}$ cycloalkyl; and substituted or unsubstituted phenyl, the phenyl substituents being selected from hydroxyl, halogen, carbonyl, $C_1$-$C_{20}$ alkoxycarbonyl, cyano, halo($C_1$-$C_{20}$)alkyl, $C_1$-$C_{20}$ alkyl or $C_1$-$C_{20}$ alkoxy.

In accordance with some further embodiments, $R^2$ and $R^3$, for Formula (I-A) and Formula (II-A), are each independently selected from —C(O)O—$R_9$, —C(O)—N($R_{10}$)($R_{11}$), —C(O)—N(C(O)($R_{10}$))($R_{11}$), —C(O)$R_{12}$', —OC(O)$R_2$, —SO$_2R_{13}$, —OSO$_2R_{13}$, —B(O$R_{14}$)(O$R_{15}$), where $R_9$, $R_{10}$, $R_{11}$, $R_{12}$, $R_{13}$, $R_{14}$, and $R_{15}$ are each independently selected from: hydrogen; $C_1$-$C_{20}$ linear or branched alkyl; $C_1$-$C_{20}$ linear or branched perhaloalkyl; $C_1$-$C_{20}$ linear or branched alkenyl; $C_3$-$C_{10}$ cycloalkyl; and substituted or unsubstituted phenyl, the phenyl substituents being selected from hydroxyl, halogen, carbonyl, $C_1$-$C_{10}$ alkoxycarbonyl, cyano, halo($C_1$-$C_{20}$)alkyl, $C_1$-$C_{20}$ alkyl or $C_1$-$C_{20}$ alkoxy; or $R_{10}$ and $R_{11}$ together form a ring, or $R_{14}$ and $R_{15}$ together form a ring.

In accordance with some alternative embodiments, $R^2$ and $R^3$ together form a ring optionally interrupted with a divalent linking group selected from —C(O)—, —O—, —N($R_{13}$)—, and combinations of two or more thereof.

In accordance with some embodiments, $R^4$ and $R^5$, for Formula (I-A) and Formula (II-A), are each independently selected from: hydrogen; halogen selected from F, Cl, Br, and I; $C_1$-$C_{20}$ linear or branched alkyl; $C_3$-$C_{10}$ cycloalkyl; and substituted or unsubstituted phenyl, the phenyl substituents being selected from hydroxyl, halogen, carbonyl, $C_1$-$C_{20}$ alkoxycarbonyl, cyano, halo($C_1$-$C_{20}$)alkyl, $C_1$-$C_{20}$ alkyl or $C_1$-$C_{20}$ alkoxy.

In accordance with some further embodiments, $R_4$ and $R^5$, for Formula (I-A) and Formula (II-A), are each independently selected from, —C(O)N($R_{14}$)($R_{15}$) or —N($R_{14}$)($R_{15}$), where $R_{14}$ and $R_{15}$ are each independently selected from: hydrogen; $C_1$-$C_{20}$ linear or branched alkyl; $C_3$-$C_{10}$ cycloalkyl; and substituted or unsubstituted phenyl, the phenyl substituents being selected from halogen, halo($C_1$-$C_{20}$)alkyl, $C_1$-$C_{20}$ alkyl or $C_1$-$C_{20}$ alkoxy, or $R_{14}$ and $R_{15}$ together form a ring.

In accordance with some additional embodiments, $R^4$ and $R^5$, for Formula (I-A) and Formula (II-A), are each independently selected from, —O$R_{16}$ or —S$R_{16}$, where each $R_{16}$ is independently selected from: $C_1$-$C_{20}$ linear or branched alkyl; $C_3$-$C_{10}$ cycloalkyl; and substituted or unsubstituted phenyl, the phenyl substituents being selected from halogen, halo($C_1$-$C_{20}$)alkyl, $C_1$-$C_{20}$ alkyl or $C_1$-$C_{20}$ alkoxy.

In accordance with some embodiments, $R^6$ and $R^7$, for Formula (I-A) and Formula (II-A), are each independently selected from: (i) hydrogen, $C_1$-$C_{20}$ alkyl, $C_1$-$C_{20}$ haloalkyl, $C_3$-$C_{10}$ cycloalkyl, allyl, benzyl, or mono-substituted benzyl, said benzyl substituents being chosen from halogen, $C_1$-$C_{20}$ alkyl or $C_1$-$C_{20}$ alkoxy; (ii) an unsubstituted, mono- di- or tri-substituted group chosen from phenyl, naphthyl, phenanthryl, pyrenyl, quinolyl, isoquinolyl, benzofuranyl, thienyl, benzothienyl, dibenzofuranyl, dibenzothienyl, carbazolyl, or indolyl, said group substituents in each case being independently chosen from halogen, $C_1$-$C_{20}$ alkyl or $C_1$-$C_{20}$ alkoxy; (iii) mono-substituted phenyl, said substituent located at the para position being —(CH$_2$)$_t$— or —O—(CH$_2$)$_t$—, wherein t is the integer 1, 2, 3, 4, 5 or 6, said substituent being connected to an aryl group which is a member of a photochromic material; and (iv) the group —CH($R^{10}$)G, wherein $R^{10}$ is hydrogen, $C_1$—C alkyl or the unsubstituted, mono- or di-substituted aryl groups phenyl or naphthyl, and G is —CH$_2$O$R^{11}$, wherein $R^{11}$ is hydrogen, $C_1$-$C_{20}$ alkyl, $C_1$-$C_{20}$ alkoxy($C_1$-$C_{20}$)alkyl, phenyl($C_1$-$C_{20}$) alkyl, mono($C_1$-$C_{20}$ alkoxy substituted phenyl($C_1$-$C_{20}$)alkyl, or the unsubstituted, mono- or di-substituted aryl groups phenyl or naphthyl, each of said phenyl and naphthyl group substituents being $C_1$-$C_{20}$ alkyl or $C_1$-$C_{20}$ alkoxy; or (v) $R^6$ and $R^7$ together form a spiro substituent selected from a substituted or unsubstituted spiro-carbocyclic ring containing 3 to 6 carbon atoms, a substituted or unsubstituted spiro-heterocyclic ring containing 1 or 2 oxygen atoms and 3 to 6 carbon atoms including the spirocarbon atom, said spiro-carbocyclic ring and spiro-heterocyclic ring being annellated with 0, 1 or 2 benzene rings, said substituents being hydrogen or $C_1$-$C_{20}$ alkyl.

Each $R^8$, for Formula (I-A) and Formula (IV), with some embodiments, is independently selected from: $C_1$-$C_{20}$ linear or branched alkyl; $C_3$-$C_{10}$ cycloalkyl; and substituted or unsubstituted phenyl, the phenyl substituents being selected from halogen, halo($C_1$-$C_{20}$)alkyl, $C_1$-$C_{20}$ alkyl or $C_1$-$C_{20}$ alkoxy.

Ring-A, for Formula (I-A) and Formula (III-A), in accordance with some embodiments, is $C_6$-aryl.

With some embodiments, $R^1$, for Formula (I-A) and Formula (III-A), for each n is independently selected from hydrogen, $C_1$-$C_6$ linear or branched alkyl, $C_3$-$C_7$ cycloalkyl, $C_1$-$C_8$ haloalkyl, fluoro, chloro, bromo, iodo, and —O—$R_{10}$'.

With some embodiments, $R^2$ and $R^3$, for Formula (I-A) and Formula (II-A), are each independently selected from: hydrogen; cyano; nitro; $C_1$-$C_6$ linear or branched alkyl; $C_1$-$C_6$ linear or branched perfluoroalkyl; $C_3$-$C_7$ cycloalkyl.

With some further embodiments, $R^2$ and $R^3$, for Formula (I-A) and Formula (II-A), are each independently selected from: —C(O)—N($R_{10}$)($R_{11}$), —C(O)—N(C(O)($R_{10}$))($R_{11}$), —C(O)$R_{12}$', —OC(O)$R_{12}$', —SO$_2R_{13}$, —OSO$_2R_{13}$, or —B(O$R_{14}$)(O$R_{15}$), where $R_9$, $R_{10}$, $R_{11}$, $R_{12}$, $R_{13}$, $R_{14}$, and $R_{15}$ are each independently selected from: hydrogen; $C_1$-$C_6$ linear or branched alkyl; and $C_1$-$C_6$ linear or branched perhaloalkyl; or $R_{10}$ and $R_{11}$ together form a ring, or $R_{14}$ and $R_{15}$ together form a ring.

In accordance with some alternative embodiments, $R^2$ and $R^3$ together form a ring optionally interrupted with a divalent linking group selected from —C(O)—, —O—, —N($R_{13}$)—, and combinations of two or more thereof.

With some embodiments, $R^4$ and $R^5$, for Formula (I-A) and Formula (III-A), are each independently selected from: hydrogen; $C_1$-$C_6$ linear or branched alkyl; $C_3$-$C_7$ cycloalkyl; and substituted or unsubstituted phenyl, the phenyl substituents being selected from halogen, halo($C_1$-$C_6$)alkyl, $C_1$-$C_6$ alkyl or $C_1$-$C_6$ alkoxy.

With some embodiments, $R^6$ and $R^7$, for Formula (I-A) and Formula (III-A), are each independently selected from hydrogen, $C_1$-$C_8$ alkyl, $C_1$-$C_8$ haloalkyl, and $C_3$-$C_7$ cycloalkyl, or $R^6$ and $R^7$ together form a spiro substituent selected from a substituted or unsubstituted spiro-carbocyclic ring containing 3 to 6 carbon atoms.

Each $R^8$, for Formula (I-A) and Formula (IV), with some embodiments, is independently selected from, $C_1$-$C_6$ linear or branched alkyl, and $C_3$-$C_7$ cycloalkyl.

The fused ring indeno compound represented by Formula (I-A), in accordance with some embodiments, is represented by the following Formula (I-C), in which Ring-A is an $R^1$ substituted $C_6$-aryl (or phenyl) group:

(I-C)

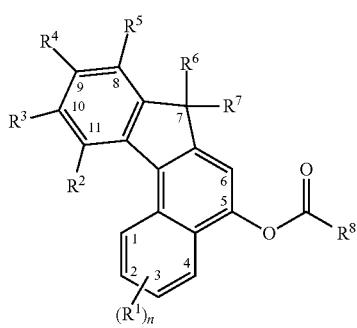

Correspondingly, and in accordance with some embodiments, the lactone compound represented by Formula (III-A) is represented by the following Formula (III-B), in which Ring-A is an $R^1$ substituted $C_6$-aryl (or phenyl) group:

(III-B)

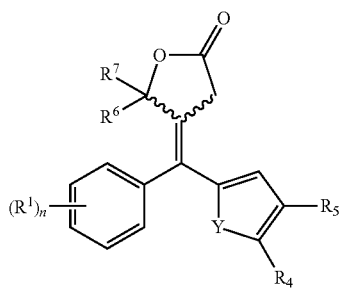

With reference to Formula (I-C) and Formula (III-B), n is 1 to 4. With further reference to Formula (I-C) and Formula (III-B), the $R^1$-$R^8$ groups are as described herein with reference to Formula (I-A).

The fused ring indeno compound represented by Formula (I-B), with some embodiments, is represented by the following Formula (I-D), in which Ring-A is an $R^1$ substituted $C_6$-aryl (or phenyl) group:

(I-D)

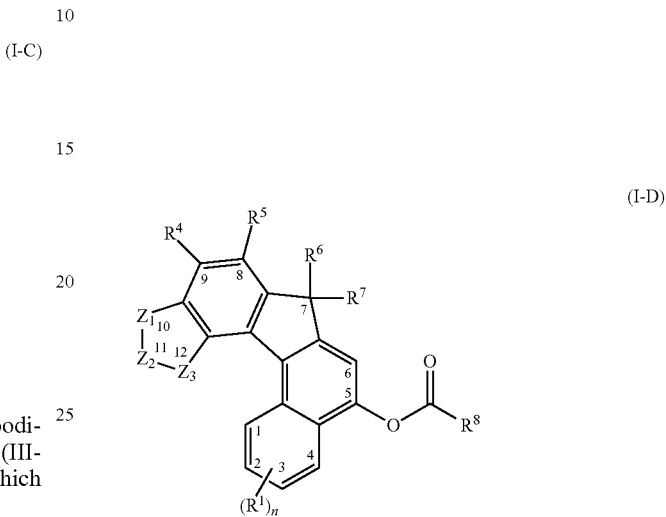

With reference to Formula (I-D), n is 1 to 4. With further reference to Formula (I-D), $R^1$, $R^4R^8$, and $Z_1$-$Z_3$ are each as described herein with reference to Formula (I-A) and Formula (I-B). The ring including $Z_1$-$Z_3$ is bonded to both ring positions of the indeno portion of the indeno-naptho fused ring structure as shown in Formula (I-D).

Examples of fused ring indeno compounds prepared by the method of the present invention, based on Formula (I-D), include, but are not limited to, the following:

(I-D)-(1)

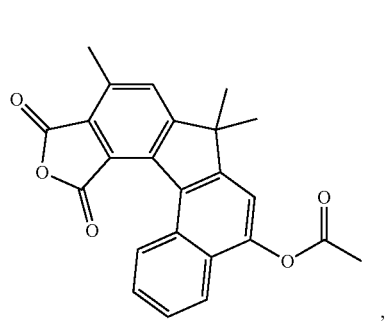

10,12-dioxo-7,7,9-trimethyl-10,12-dihydro-7H-furo[3',4':4,5]indeno[3,2-a]naphthalen-5-yl acetate (I-D)-(2)

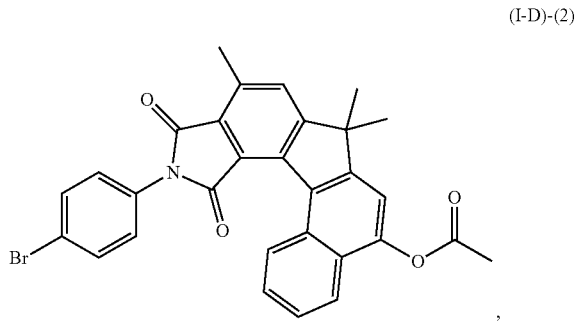

11-(4-bromophenyl)10,12-dioxo-7,7,9-trimethyl-7,10,11,12-tetrahydropyrrolo[3',4':4,5]indeno[3,2-a]naphthalen-5-yl acetate

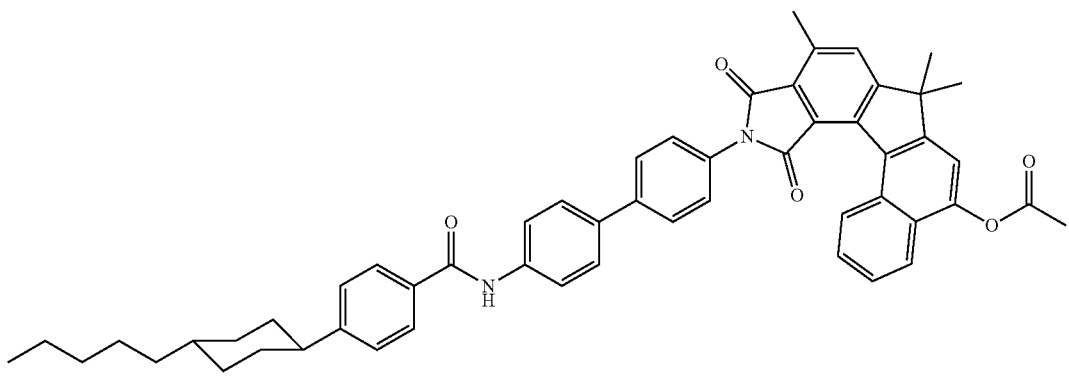

(I-D)-(3)

11-(4'-(4-(trans-4-pentylcyclohexyl)benzamido)-[1,1'-biphenyl])-10,12-dioxo-
7,7,9-trimethyl-7,10,11,12-tetrahydropyrrolo[3',4':4,5]indeno[3,2-a]naphthalen-5-yl acetate

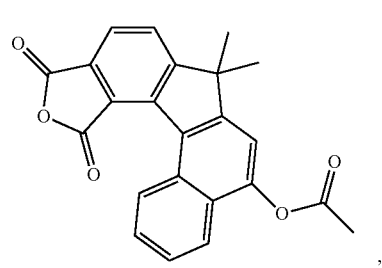

(I-D)-(4)

10,12-dioxo-7,7-dimethyl-10,12-dihydro-7H-
furo[3',4':4,5]indeno[3,2-a]naphthalen-5-yl acetate

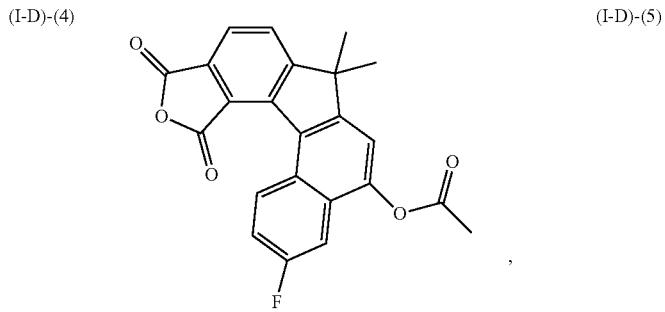

(I-D)-(5)

10,12-dioxo-7,7-dimethyl-3-fluoro-10,12-dihydro-7H-
furo[3',4':4,5]indeno[3,2-a]naphthalen-5-yl acetate

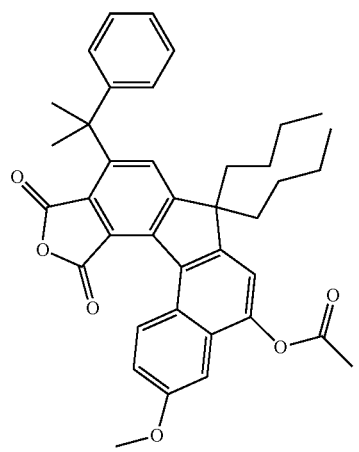

(I-D)-(6)

10,12-dioxo-7,7,-dibutyl-3-methoxy-9-(2-phenylpropan-2-yl)-
10,12-dihydro-7H-furo[3',4':4,5]indeno[3,2-a]naphthalen-5-yl acetate

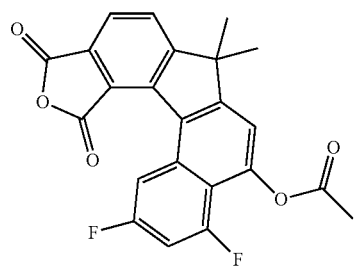

(I-D)-(7)

10,12-dioxo-7,7-dimethyl-2,4-difluoro-10,12-dihydro-7H-
furo[3',4':4,5]indeno[3,2-a]naphthalen-5-yl acetate (I-D)-(8)

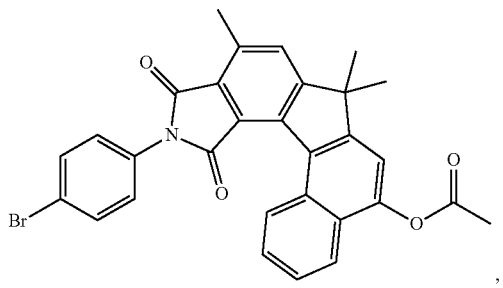

11-(4-bromophenyl)-10-oxo-7,7,9-trimethyl-
7,10,11,12-tetrahydropyrrolo
[3′,4′:4,5]indeno[3,2-a]naphthalen-5-yl acetate (I-D)-(9)

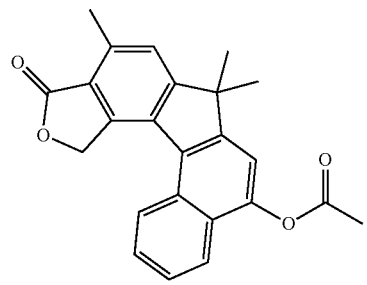

10-oxo-7,7,9-trimethyl-10,12-dihydro-7H-furo
[3′,4′:4,5]indeno[3,2-a]naphthalen-5-yl acetate (I-D)-(10)

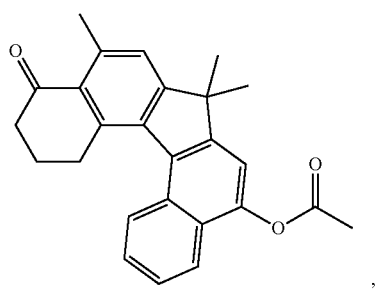

10-oxo-7,7,9-trimethyl-10,11,12,13-tetrahydro-7H-
benzo[4,5]indeno[3,2-a]naphthalen-5-yl acetate (I-D)-(11)

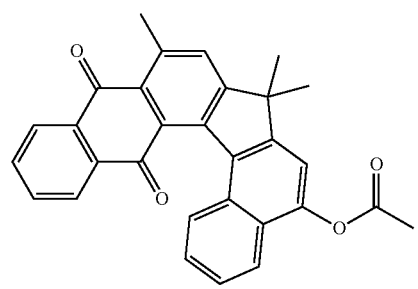

10,15-dioxo-7,7,9-trimethyl-10,15-dihydro-7H-
naphtho[2′,3′:4,5]indeno[3,2-a]naphthalen-5-yl acetate (I-D)-(12)

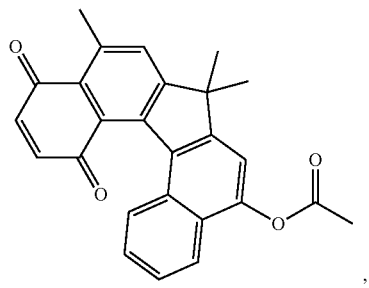

10,13-dioxo-7,7,9-trimethyl-10,13-dihydro-7H-
benzo[4,5]indeno[3,2-a]naphthalen-5-yl acetate (I-D)-(13)

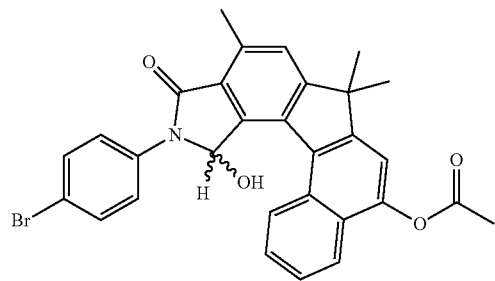

11-(4-bromophenyl)-12-hydroxy-10-oxo-7,7,9-trimethyl-
7,10,11,12-tetrahydropyrrolo [3′,4′:4,5]indeno[3,2-
a]naphthalen-5-yl acetate , and (I-D)-(14)

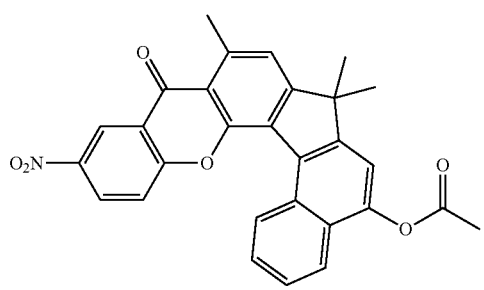

12-nitro-10-oxo-7,7,9-trimethyl-7H-chromeno[3′,2′:4,5]indeno[3,2-
a]naphthalen-5-yl acetate The present invention also provides a method of forming the fused ring indeno compound represented by Formula (I-E) as follows.

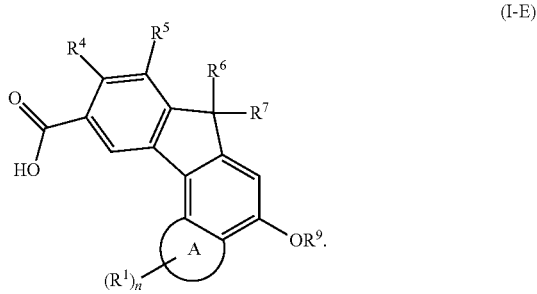

(I-E)

With reference to Formula (I-E), Ring-A, n, $R^1$, and $R^4$-$R^7$ are each as described herein with reference to Formula (I-A). The $R^9$ group of Formula (I-E) is selected from —C(O)—$R_{19}$ and —S(O)(O)$R_{19}$, wherein $R_{19}$ is selected from hydrocarbyl, and halohydrocarbyl.

The carboxylic acid functional fused ring indeno compound represented by Formula (I-E) is prepared, in accordance with some embodiments, by a two-step process, that includes a first step and a second step. The first step, second step, and one or more optional further steps, can be conducted sequentially, such as in a single reaction vessel.

In the first step, maleic anhydride and a lactone compound represented by Formula (III-A), when Y is an oxygen, as described previously herein, are reacted together in the presence of a catalyst, and a solvent. The solvent is substantially free of reaction with water. With regard to the solvent, that is used in the method of forming the fused ring indeno compound represented by Formula (I-E), by "substantially free of reaction with water" means the solvent substantially maintains its structure in the presence of water. With some embodiments, the solvent, of the first step, is selected from benzene, xylene, toluene, methylene chloride, chloroform, 1,2-dichloroethane, acetonitrile, nitromethane and combinations of two or more thereof.

The first step of forming the fused ring indeno compound represented by Formula (I-E) results in the formation of an acid intermediate represented by Formula (VIII-A),

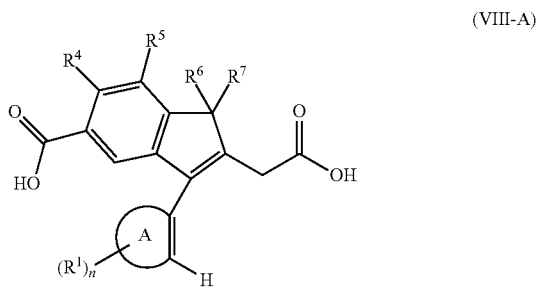

(VIII-A)

With reference to Formula (VIII-A), Ring-A, n, $R^1$, and $R^4$-$R^7$ are each as described herein with reference to Formula (I-E) and Formula (I-A).

Figure 5:
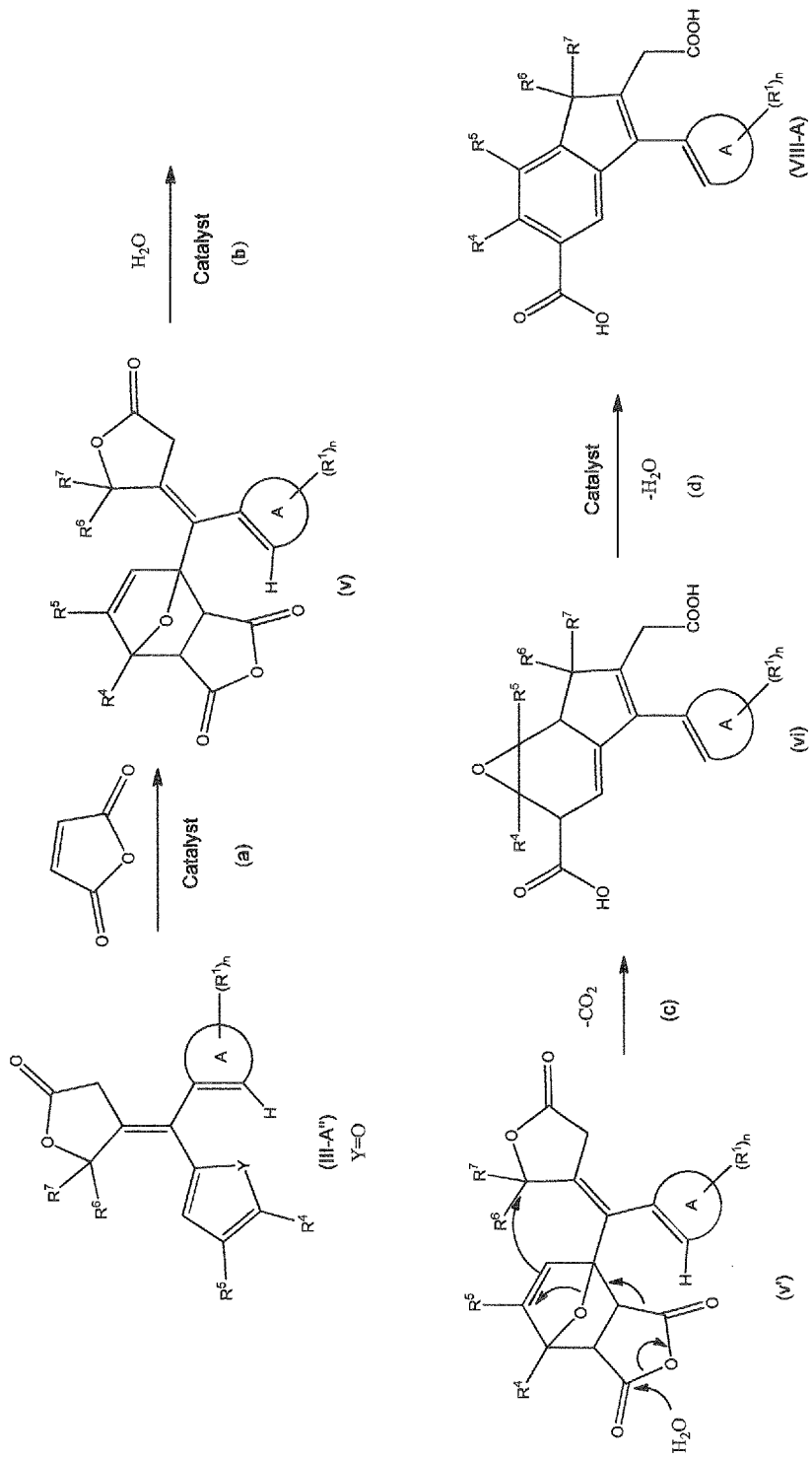
FIG. 5 is an illustrative representative scheme, Scheme-(5), of a reaction pathway by which the acid intermediate represented by Formula (VIII-A) can be formed in accordance with the present invention.

In accordance with some embodiments, for purposes of non-limiting illustration, and while not intending to be bound by any theory, formation of the acid intermediate represented by Formula (VIII-A) is believed to proceed in accordance with the reaction pathway represented by Scheme-5 of FIG. 5. With reference to Scheme-(5) of FIG. 5, in step (a) via a Diels-Alder reaction, the lactone isomer represented by Formula (III-A") reacts with maleic anhydride in the presence of catalyst (described in further detail herein) to form Intermediate-(v). In steps (b) and (c), a molecule of water attacks a carbonyl carbon of the fused ring residue of maleic anhydride. For purposes of illustration, Intermediate-(v') is provided in FIG. 5, which is the same as Intermediate-(v), but includes arcuate arrows representing the movement of electrons throughout the structure when a molecule of water nucleophilically attacks the carbonyl carbon as depicted. The source of the water can, with some embodiments, be moisture in the solvent, or separately added water, or the water co-product from this reaction, or any combination thereof. In the same steps (b) and (c), a molecule of carbon dioxide is generated as a co-product. Generation of such gaseous carbon dioxide provides extra driving force for the formation of the fused ring of Intermediate-(vi). As a result of this, the competing side reaction (not depicted in FIG. 5) between Ring A and the lactone ring is minimized. The other lactone structural isomer represented by Formula (III-A') is converted to the structural isomer represented by Formula (III-A") via the equilibrium represented by Scheme-(4) of FIG. 4. In step (d), which is an aromatization step, Intermediate-(vi) is converted to the acid intermediate represented by Formula (VIII-A). During the course of step (d) there is the concurrent formation of $H_2O$.

The acid intermediate represented by Formula (VIII-A) can, with some embodiments, be isolated from the reaction as demonstrated in Example 6A and Example 7A of the Examples further herein. In accordance with some further embodiments, the acid intermediate represented by Formula (VIII-A) is not isolated, and the second step of the reaction can be conducted in the same reaction vessel.

The method of forming the fused ring indeno compound represented by Formula (I-E) includes a second step, in which the acid intermediate represented by Formula (VIII-A) is converted to the fused ring indeno compound represented by Formula (I-E) in the presence of a material selected from carboxylic acid halide, carboxylic acid anhydride, sulfonyl halide, sulfonyl anhydride, and combinations thereof. The carboxylic acid halide, carboxylic acid anhydride, sulfonyl halide, sulfonyl anhydride, with some embodiments, are each represented by the formulas as provided in the following Table A.

TABLE A

| Carboxylic acid halide | $R_{19}$—C(O)—X |
| Carboxylic acid anhydride | $R_{19}$—C(O)—O—C(O)—$R_{19}$ |
| Sulfonyl halide | $R_{19}$(O)(O)S—X |
| Sulfonyl anhydride | $R_{19}$(O)(O)S—O—S(O)(O)$R_{19}$ |

With reference to the general formulas provided in Table A: X in each case is independently selected from halide, such as F, Cl, Br, and I; and $R_{19}$ in each case is independently selected from hydrocarbyl, and halohydrocarbyl, such as, but not limited to linear or branched $C_1$-$C_{20}$ alkyl, linear or branched $C_1$-$C_{20}$ haloalkyl, linear or branched $C_1$-$C_{20}$ perhaloalkyl, aryl, haloaryl, and perhaloaryl. In accordance with some embodiments, the second step by which the acid intermediate represented by Formula (VIII-A) is converted to the fused ring indeno compound represented by Formula (I-E) is conducted in the presence of a carboxylic acid anhydride. For purposes of non-limiting illustration and with reference to Scheme-6 of FIG. 6, the acid intermediate represented by Formula (VIII-A) is converted to the fused ring indeno compound represented by Formula (I-E) in the presence of a carboxylic acid anhydride represented by Formula (VI'), with the concurrent generation of one molecule of water.

In the first step of forming the fused ring indeno compound represented by Formula (I-E), the catalyst is selected from at least one Lewis acid represented by the following Formula (V) and Formula (VI),

and

With reference to Formula (V) and Formula (VI), M, y, and $R_{20}$ are each as described previously herein. The catalyst, with some embodiments, is present in the first step in an amount of at least 0.001 percent by moles, based on moles of the lactone compound represented by Formula (III-A), such as from 0.001 to 99 percent by moles, or from 0.01 to 30 percent by moles, in each case based on moles of the lactone compound represented by Formula (III-A).

The first step of the method of forming the fused ring indeno compound represented by Formula (I-E) is conducted, with some embodiments, in the presence of an acid selected from alkyl sulfonic acid, aryl sulfonic acid, and combinations thereof. With some further embodiments, the acid is selected from p-toluene sulfonic acid, dodecylbenzenesulfonic acid, and combinations thereof. The acid, with some embodiments, is present in the first step an amount of at least 0.1 percent by moles, based on moles of the lactone compound represented by Formula (III-A), such as from 0.1 to 500 percent by moles, or from 10 to 200 percent by moles, in each case based on moles of the lactone compound represented by Formula (III-A).

The method of forming the fused ring indeno compound represented by Formula (I-E) further includes, with some embodiments, a third step that is conducted after the second step. The optional third step includes hydrolyzing the intermediate represented by Formula (VIII-A) in the presence of a protonic acid or a base, thereby forming an indeno compound represented by the following Formula (I-F):

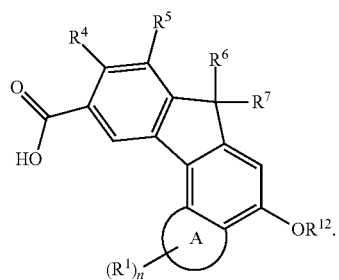

With reference to Formula (I-F), Ring-A, n, $R^1$, and $R^4$-$R^7$ are each as described herein with reference to Formula (I-A) and Formula (I-E). With further reference to Formula (I-F), $R^{12}$ is hydrogen.

In the optional third step of forming the fused ring indeno compound represented by Formula (I-F), the protonic acid is, with some embodiments, selected from carboxylic acids, sulfonic acids, phosphoric acids, hydrogen halides (HX, where X is halogen, such as, F, Cl, Br, or I, such as hydrochloric acid), and combinations thereof. Examples of sulfonic acids include, but are not limited to para-toluene sulfonic acid and dodecyl benzene sulfonic acid. Examples of phosphoric acids include, but are not limited to phosphoric acid. Examples of carboxylic acids include, but are not limited to oxalic acid and acetic acid. The base can be selected from sodium hydroxide and potassium hydroxide, with some embodiments. With some embodiments, the acid of the optional third step is selected from p-toluene sulfonic acid, dodecylbenzenesulfonic acid, and combinations thereof.

In the optional third step, the protonic acid or base is typically present in an excess amount relative to the amount of intermediate represented by, for example, Formula (VIII-A). For example the conversion of step-(b) can be conducted in the presence of concentrated hydrogen halide acid, such as concentrated HCl; concentrated sulfonic acid, such as p-toluene sulfonic acid; or concentrated base, such as sodium hydroxide. The optional third step is, with some embodiments, conducted in the presence of a solvent or mixture solvents (e.g., methanol, THF, toluene or methanol/water mixture), under reflux conditions, for example at a temperature from 20° C. to the reflux temperature of the solvent or from 25° C. to 90° C., or from 30° C. to 55° C., under conditions of ambient pressure (such as, approximately 1 atm).

Figure 6:
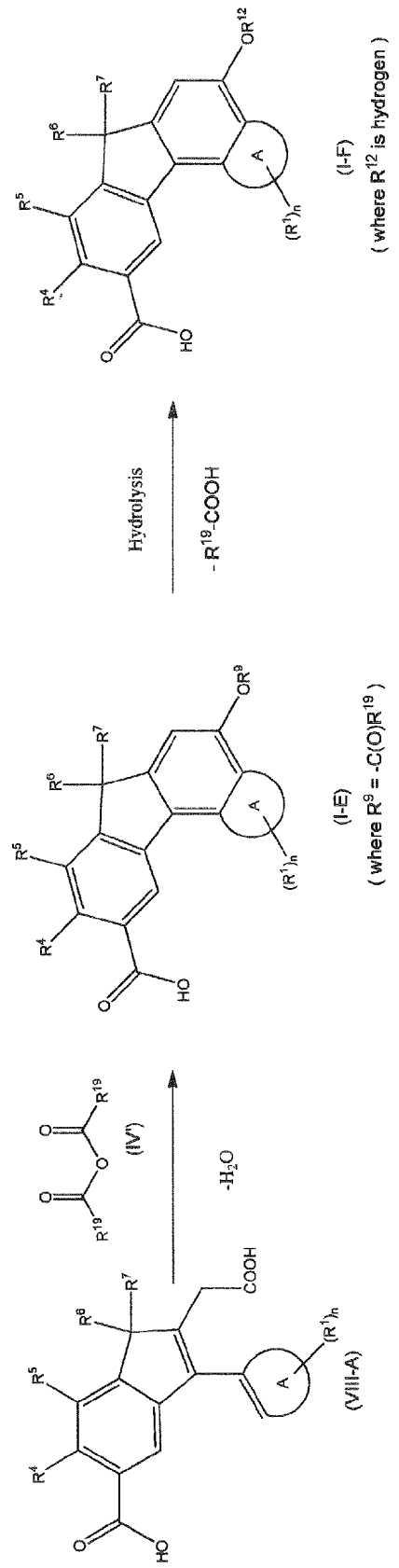
FIG. 6 is an illustrative representative scheme, Scheme-(6), of a method of forming carboxylic acid functional fused ring indeno compounds represented by Formulas (I-E) and (I-F) in accordance with the present invention.

For purposes of non-limiting illustration, the optional third step of converting the fused ring indeno compound represented by Formula (I-E) to the fused ring indeno compound represented by Formula (I-F) is depicted in Scheme-6 of FIG. 6. With reference to Scheme-6 of FIG. 6, the fused ring indeno compound represented by Formula (I-E) is subjected to a hydrolysis reaction in the presence of a protonic acid so as to form the fused ring indeno compound represented by Formula (I-F), with the concurrent formation of carboxylic acid ($R^{19}$—COOH).

In accordance with some embodiments, the first, second, and third steps, as described above, are conducted sequentially in a single reaction vessel, without isolation of any of the intermediates depicted in Schemes (5) and (6) of FIGS. 5 and 6.

In accordance with some embodiments of the present invention: the fused ring indeno compound represented by Formula (I-E) is represented by the following Formula (I-G),

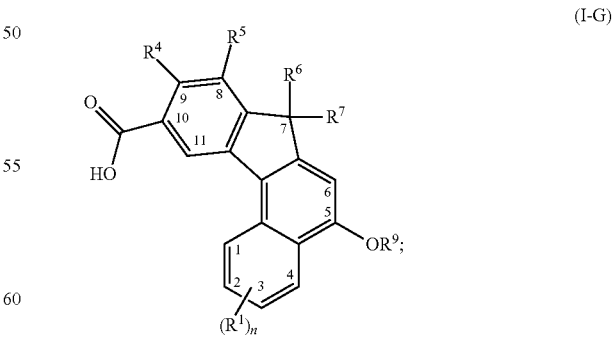

and the lactone compound represented by Formula (III-A) is represented by Formula (III-B) as described previously herein; and the acid intermediate represented by Formula (VIII-A) is represented by the following Formula (VIII-B),

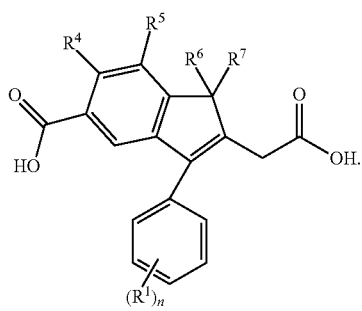

(VIII-B)

With reference to Formula (I-G), Formula (III-B), and Formula (VIII-B), n is selected from 1 to 4. With further reference to Formula (I-G) and Formula (VIII-B), $R^1$, $R^4$-$R^7$, and $R^9$ are each as described herein with reference to Formula (I-E) and Formula (I-A). Formula (III-B) is as described previously herein. With Formulas (I-G), (III-B), and (VIII-B), Ring-A is an $R^1$ substituted $C_6$-aryl (or phenyl) group The present invention also relates to a compound represented by Formula (VIII-A) as described previously herein. The compound represented by Formula (VIII-A) is, with some embodiments, isolated from the method of the present invention. With reference to Formula (VIII-A), Ring-A, n, $R^1$, and $R^4$-$R^7$ are each as described previously herein with reference to Formula (I-A).

The present invention also relates to a compound represented by Formula (VIII-B) as described previously herein. The compound represented by Formula (VIII-B) is, with some embodiments, isolated from the method of the present invention. With reference to Formula (VIII-B), n is selected from 1 to 4, and $R^1$ and $R^4$-$R^7$ are each as described previously herein with reference to Formula (I-A).

Examples of fused ring indeno compounds prepared by the method of the present invention, based on Formula (I-G), include, but are not limited to, the following:

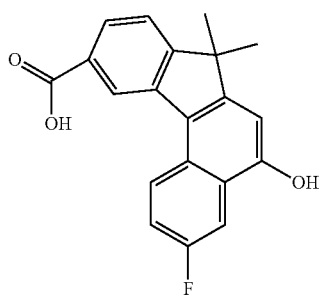

(I-G)-(1)

10-carboxy-7,7-dimethyl-3-fluoro-
7H-indeno[3,2-a]naphthalen-5-ol

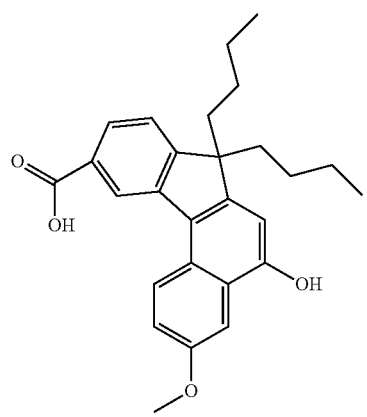

(I-G)-(2)

10-carboxy-7,7-dibutyl-3-methoxy-
7H-indeno[3,2-a]naphthalen-5-ol

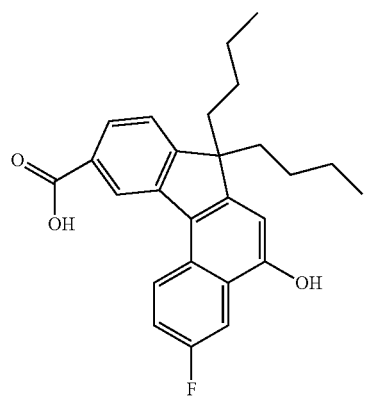

(I-G)-(3)

10-carboxy-7,7-dibutyl-3-fluoro-
7H-indeno[3,2-a]naphthalen-5-ol

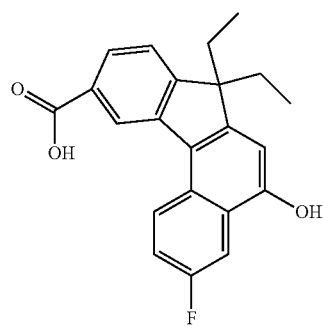

(I-G)-(4)

10-carboxy-7,7-diethyl-3-fluoro-
7H-indeno[3,2-a]naphthalen-5-ol

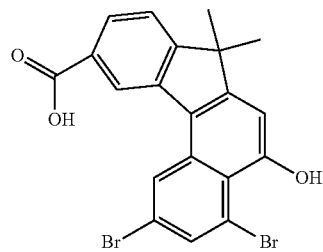

(I-G)-(5)

10-carboxy-2,4-dibromo-7,7-dimethyl-
7H-indeno[3,2-a]naphthalen-5-ol

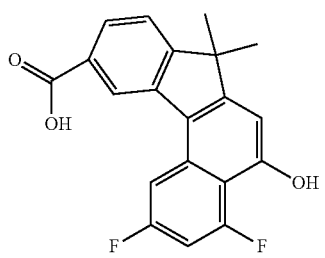

10-carboxy-2,4-difluoro-7,7-dimethyl-
7H-indeno[3,2-a]naphthalen-5-ol

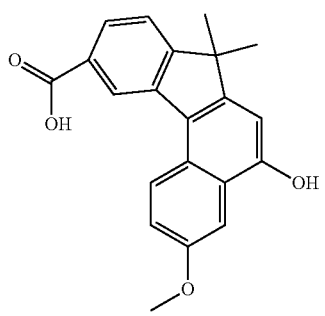

10-carboxy-7,7-dimethyl-3-methoxy-
7H-indeno[3,2-a]naphthalen-5-ol

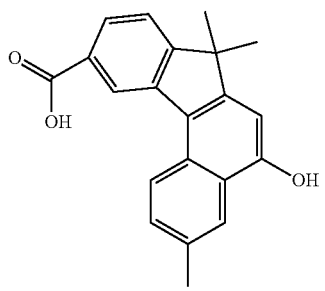

10-carboxy-7,7-dimethyl-3-methyl-
7H-indeno[3,2-a]naphthalen-5-ol

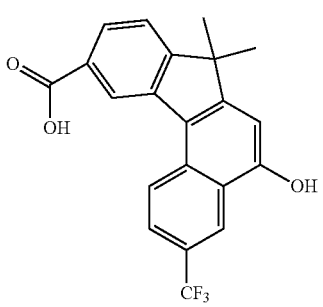

10-carboxy-7,7-dimethyl-3-trifluoromethyl-
7H-indeno[3,2-a]naphthalen-5-ol (I-G)-(6)

(I-G)-(7)

(I-G)-(8)

(I-G)-(9)

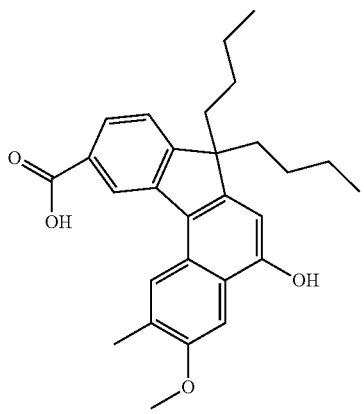

10-carboxy-7,7-dibutyl-3-methoxy-2-methyl-
7H-indeno[3,2-a]naphthalen-5-ol

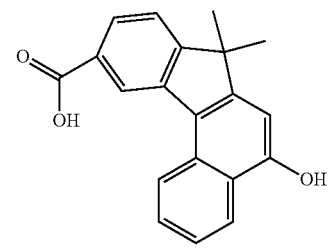

10-carboxy-7,7-dimethyl-7H-indeno[3,2-a]naphthalen-5-ol

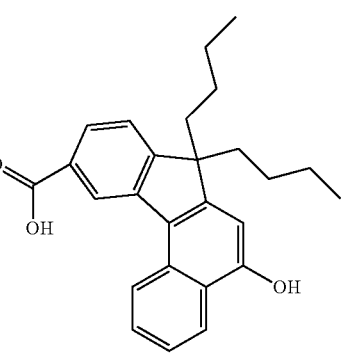

10-carboxy-7,7-dibutyl-7H-indeno[3,2-a]naphthalen-5-ol (I-G)-(10)

(I-G)-(11)

(I-G)-(12)

The lactone compounds used in the methods of the present invention are, with some embodiments, prepared by art-recognized procedures. For purposes of non-limiting illustration, and with reference to Scheme-7 of FIG. 7, the lactone compound represented by Formula (III-A) is prepared, in accordance with some embodiments, by reacting an acid ester represented by Formula (1) with a metal hydride reducing agent that is defined herein to include an organo metal hydride reducing agent, or a nucleophile represented by at least one of Formula (2) and/or Formula (3). The wavy bonds (∿) of Formula (1) indicate that the positions of the Ring-(A) and the five member ring (including Y, $R^4$ and $R^5$) can be switched relative to the double bond extending from the junction of the two wavy bonds, and as such, Formula (1) represents both structural isomers relative to the double bond.

Figure 7:
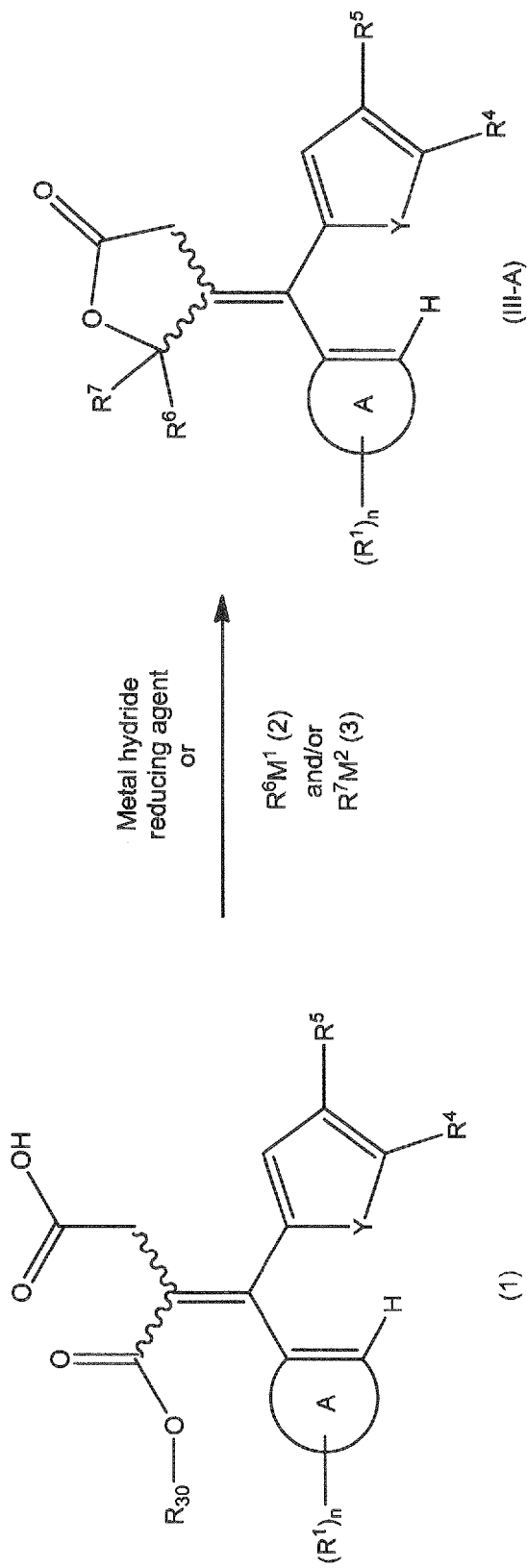
FIG. 7 is an illustrative representative scheme, Scheme-(7), of a method of preparing the lactone compound of the method of the present invention.

With further reference to Scheme-7 of FIG. 7, the metal hydride reducing agent is typically used when $R^6$ and $R^7$ are each hydrogen. The metal hydride reducing agent can, with some embodiments, be selected from sodium borohydride and lithium aluminum hydride, or an organo metal hydride reducing agent. The organo metal hydride reducing agent can be one or more di($C_1$-$C_{20}$ alkyl) aluminum hydride reducing agents, such as one or more di($C_1$-$C_6$ alkyl) aluminum hydride reducing agents, examples of which include, but are not limited to, diethyl aluminum hydride and diisobutyl aluminum hydride.

With reference to Formulas (2) and (3) of Scheme-7 of FIG. 7, $M^1$ and $M^2$ are each independently selected from $Si(R^{31})_3$, where each $R^{31}$ is independently selected from $C_1$-$C_8$ alkyl, or $M^1$ and $M^2$ each independently represent a counterion that includes a metal selected from Mg, Li, Mn, Cu, Zn, Al, Ti, Ln, and combinations thereof. With some embodiments, $R_{30}$ of the acid ester represented by Formula (1) is selected from hydrocarbyl and substituted hydrocarbyl. With some further embodiments, $R_{30}$ of the acid ester represented by Formula (1) is selected from linear or branched $C_1$-$C_{20}$ alkyl, such as linear or branched $C_1$-$C_6$ alkyl (such as ethyl, with some embodiments).

According to some embodiments, and with further reference to Scheme-7 of FIG. 7, $M^1$ and $M^2$ of Formulas (2) and (3) also include a halogen, and can be represented by $(M^1X)^+$ and $(M^2X)^+$, in which X is a halogen. Each of $M^1$ and $M^2$ of Formulas (2) and (3) can each be selected from $(MgX)^+$, in which X is selected from halogen, such as Cl, Br and I, examples of which include, but are not limited to, $(MgCl)^+$, $(MgBr)^+$ and $(MgI)^+$.

With some embodiments, the nucleophiles represented by Formulas (2) and (3) of Scheme-7 of FIG. 7, are each Grignard reagents, and the reaction represented by Scheme-7 is a Grignard reaction, which is conducted under Grignard reaction conditions. The reaction represented by Scheme-7 is typically conducted in the presence of an appropriate solvent, such as tetrahydrofuran (THF), and under conditions of ambient pressure (e.g., approximately 1 atm), under an inert atmosphere (e.g., under a nitrogen sweep), such as from −30° C. to 60° C., or from −20° C. to 45° C., or from −10° C. to 30° C., and optionally with reflux.

The reaction of the acid ester represented by Formula (1) with the nucleophile represented by Formulas (2) and/or (3), of Scheme-7, is with some embodiments, conducted in the presence of metal salts. Examples of metal salts that can be present include, but are not limited to, aluminum chloride ($AlCl_3$), tin chloride, zinc chloride, bismuth triflate, alkali metal halides, anhydrous alkaline metal halides, rare earth metal salts, e.g., lanthanide halides, such as lanthanum III chloride, and lanthanide triflate, and combinations thereof. Examples of alkali metal halides that can be present include, but are not limited to, sodium halides and/or potassium halides, such as sodium chloride (NaCl) and/or potassium chloride (KCl). Examples of alkaline metal halides that can be present include, but are not limited to, anhydrous calcium halides, anhydrous lithium halides and/or anhydrous magnesium halides, such as calcium chloride, lithium chloride and magnesium chloride. The metal salt is typically present in an amount of from 0.1 molar percent to 600 molar percent, or from 1.0 to 100 molar percent, or from 10 to 50 molar percent, based on 100 molar percent of the starting materials. The molar percent is defined herein as the percentage of the number of moles of the metal salt per liter of solute based on the total moles per liter of solute of the acid ester represented by Formula (1) and the nucleophiles represented by Formulas (2) and (3) in Scheme-7.

In accordance with some embodiments, the lactone compounds represented by Formula (III-A) (Including Formulas (III-A') and (III-A")), after formation thereof, can be subjected to one or more additional chemical reactions for purposes of modifying one or more of the groups thereof, such as the $R^1$, $R^4$, $R^5$, $R^6$, and/or $R^7$ groups. Examples of modified groups include, but are not limited to, lengthening groups, such as group L (or L groups) as described previously herein with reference to Formula (VII). With some embodiments, the groups of the lactone compounds represented by Formula (III-A) are subsequently modified because the modified groups would not survive formation of the lactone itself. Examples of additional chemical reactions that the lactone compounds represented by Formula (III-A) can be subjected to include, but are not limited to, Friedel-Crafts reactions, palladium-catalyzed cross couplings, cyanation chemistries, etherifications, C—H bond activation chemistries, borylation chemistries, esterifications, amidations, oxidation chemistries, and reduction chemistries. For purposes of non-limiting illustration, the modification of lactone compounds represented by Formula (III-A) is shown in Examples 3, 4 and 5 further herein, in which the starting lactones were converted in-situ to modified lactones having new substituents, such as but not limited to, 9-(2-phenylpropan-2-yl), before other reactions were undertaken.

The acid ester represented by Formula (1) of Scheme-7 can be prepared in accordance with art-recognized methods. With some embodiments, the acid ester represented by Formula (1) is prepared by a reaction between a ketone represented by Formula (4) and a succinic acid diester represented by Formula (5), as represented by Scheme-8 of FIG. 8.

Figure 8:
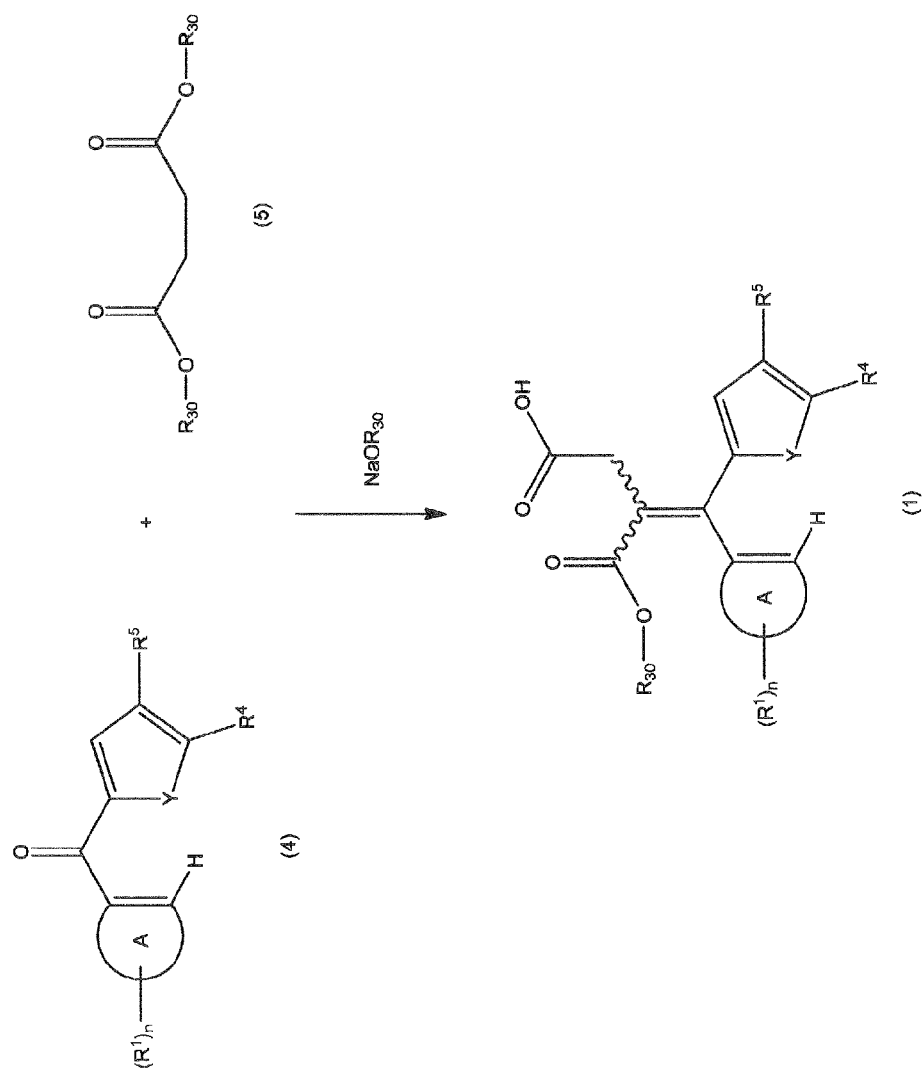
FIG. 8 is an illustrative representative scheme, Scheme-(8), of a method of preparing an acid ester precursor of the lactone compound of the method of the present invention.

With reference to Scheme-8 of FIG. 8, the ketone represented by Formula (4) is reacted with a succinic acid diester represented by Formula (5), in which each $R_{30}$ is as described previously herein (e.g., each $R_{30}$ can be ethyl), in the presence of a strong base, such as an alkali metal alkoxide, such as $NaOR_{30}$ (e.g., sodium ethoxide). The reaction of Scheme-8 is conducted under appropriate conditions, such as under reflux at a temperature of the boiling point of the solvent, under an inert atmosphere, and in the presence of an appropriate solvent, such as tetrahydrofuran or toluene. Workup of the reaction represented by Scheme-8 is conducted, with some embodiments, in accordance with art-recognized procedures.

The fused ring indeno compounds prepared by the methods of the present invention, such as represented by Formula (I-A), and certain intermediate compounds, such as represented by Formula (VII-A), are used as an intermediate for preparation of a photochromic compound, with some embodiments. In accordance with some embodiments, the fused ring indeno compounds prepared by the methods of the present invention and certain intermediate compounds are used to prepare photochromic fused ring indenopyran compounds, such as represented by the following Formula (I-A-PC) and Formula (I-B-PC):

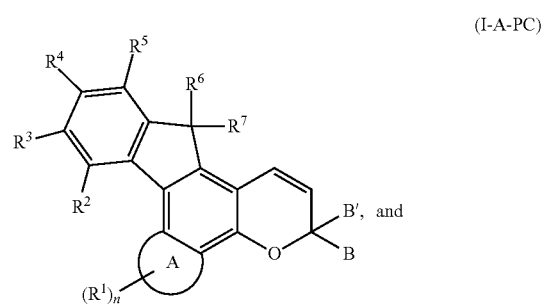

(I-A-PC)

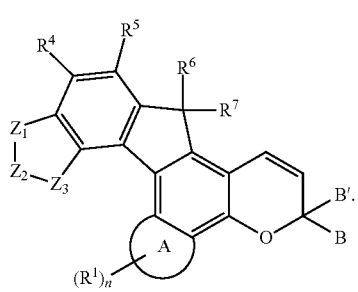

(I-B-PC)

With reference to Formulas (I-A-PC) and (I-B-PC), Ring-A, n, and $R^1$-$R^7$ are each as described herein with reference to Formula (I-A). With further reference to Formula (I-B-PC), $Z_1$-$Z_3$ are each as described herein with reference to Formula (I-B).

With further reference to Formulas (I-A-PC) and (I-B-PC), B and B' are each independently selected from, hydrogen, unsubstituted hydrocarbyl, and substituted hydrocarbyl, in which the hydrocarbyl and substituted hydrocarbyl are each optionally and independently interrupted with at least one of —O—, —S—, —C(O)—, —C(O)O—, —S(O)—, —SO$_2$—, —N=N—, —N($R_{11}'$)— where $R_{11}'$ is selected from hydrogen, hydrocarbyl or substituted hydrocarbyl, —Si(O$R_8'$)$_w$($R_8'$)$_t$—, where w and t are each independently selected from 0 to 2, provided that the sum of w and t is 2, and each $R_8'$ is independently selected from hydrogen, hydrocarbyl and substituted hydrocarbyl, and combinations of two or more thereof, or B and B' taken together form a ring structure selected from unsubstituted fluoren-9-ylidene, substituted fluoren-9-ylidene, saturated spiro-monocyclic hydrocarbon ring, saturated spiro-bicyclic hydrocarbon ring, and spiro-tricyclic hydrocarbon ring.

In accordance with some embodiments, and with further reference to Formulas (I-A-PC) and (I-B-PC), B and B' are each independently selected from, hydrogen, unsubstituted aryl, substituted aryl, unsubstituted heteroaryl, and substituted heteroaryl, or B and B' taken together form a ring structure selected from unsubstituted fluoren-9-ylidene, substituted fluoren-9-ylidene, saturated spiro-monocyclic hydrocarbon ring, saturated spiro-bicyclic hydrocarbon ring, and spiro-tricyclic hydrocarbon ring.

In accordance with some further embodiments, B and B' of Formulas (I-A-PC) and (I-B-PC) are each independently selected from: an aryl group that is mono-substituted with a reactive substituent or a compatiblizing substituent; a substituted phenyl; a substituted aryl; a substituted 9-julolidinyl; a substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl, wherein the phenyl, aryl, 9-julolidinyl, or heteroaromatic substituent is a reactive substituent R; an unsubstituted, mono-, di-, or tri-substituted phenyl or aryl group; 9-julolidinyl; or an unsubstituted, mono- or di-substituted heteroaromatic group chosen from pyridyl, furanyl, benzofuran-2-yl, benzofuran-3-yl, thienyl, benzothien-2-yl, benzothien-3-yl, dibenzofuranyl, dibenzothienyl, carbazoyl, benzopyridyl, indolinyl, and fluorenyl. With some further embodiments, each of the phenyl, aryl and heteroaryl substituents are each independently selected from: hydroxyl, a group —C(=O)$R_{21}$, wherein $R_{21}$ is —O$R_{22}$, —N($R_{23}$)$R_{24}$, piperidino, or morpholino, wherein $R_{22}$ is allyl, $C_1$-$C_{20}$ alkyl, phenyl, mono ($C_1$-$C_{20}$)alkyl substituted phenyl, mono($C_1$-$C_{20}$)alkoxy substituted phenyl, phenyl($C_1$-$C_{20}$)alkyl, mono($C_1$-$C_{20}$)alkyl substituted phenyl($C_1$-$C_{20}$)alkyl, mono($C_1$-$C_{20}$)alkoxy substituted phenyl($C_1$-$C_{20}$)alkyl, $C_1$-$C_{20}$ alkoxy($C_2$-$C_{20}$)alkyl or $C_1$-$C_{20}$ haloalkyl, $R_{23}$ and $R_{24}$ are each independently $C_1$-$C_{20}$ alkyl, $C_5$-$C_{10}$ cycloalkyl, phenyl or substituted phenyl, the phenyl substituents being $C_1$-$C_{20}$ alkyl or $C_1$-$C_{20}$ alkoxy, and said halo substituent is chloro or fluoro, aryl, mono($C_1$-$C_{20}$)alkoxyaryl, di($C_1$-$C_{20}$)alkoxyaryl, mono($C_1$-$C_{20}$)alkylaryl, di($C_1$-$C_{20}$)alkylaryl, haloaryl, $C_3$-$C_{10}$ cycloalkylaryl, $C_3$-$C_{10}$ cycloalkyl, $C_3$-$C_{10}$ cycloalkyloxy, $C_3$-$C_{10}$ cycloalkyloxy($C_1$-$C_{20}$)alkyl, $C_3$-$C_{10}$ cycloalkyloxy ($C_1$-$C_{20}$)alkoxy, aryl($C_1$-$C_{20}$)alkyl, aryl($C_1$-$C_{20}$)alkoxy, aryloxy, aryloxy($C_1$-$C_{20}$)alkyl, aryloxy($C_1$-$C_{20}$)alkoxy, mono- or di-($C_1$-$C_{20}$)alkylaryl($C_1$-$C_{20}$)alkyl, mono- or di-($C_1$-$C_{20}$) alkoxyaryl($C_1$-$C_{20}$)alkyl, mono- or di-($C_1$-$C_{20}$)alkylaryl($C_1$-$C_{20}$)alkoxy, mono- or di-($C_1$-$C_{20}$)alkoxyaryl($C_1$-$C_{20}$) alkoxy, amino, mono- or di-($C_1$-$C_{20}$)alkylamino, diarylamino, piperazino, N—($C_1$-$C_{20}$)alkylpiperazino, N-arylpiperazino, aziridino, indolino, piperidino, morpholino, thiomorpholino, tetrahydroquinolino, tetrahydroisoquinolino, pyrrolidyl, $C_1$-$C_{20}$ alkyl, $C_1$-$C_{20}$ haloalkyl, $C_1$-$C_{20}$ alkoxy, mono($C_1$-$C_{20}$)alkoxy($C_1$-$C_{20}$)alkyl, acryloxy, methacryloxy, or halogen.

With some further embodiments, B and B' of Formulas (I-A-PC) and (I-B-PC) are each independently selected from an unsubstituted or mono-substituted group chosen from pyrazolyl, imidazolyl, pyrazolinyl, imidazolinyl, pyrrolinyl, phenothiazinyl, phenoxazinyl, phenazinyl, and acridinyl, in which each of the substituents being $C_1$-$C_{20}$ alkyl, $C_1$-$C_{20}$ alkoxy, phenyl, or halogen.

With some additional embodiments, B and B' of Formulas (I-A-PC) and (I-B-PC) are each independently selected from a group represented by one of the following Formulas (XIVA) or (XIVB):

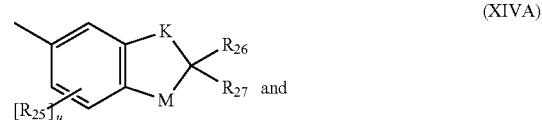

(XIVA)

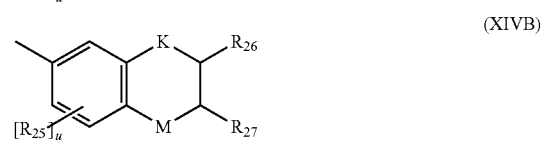

(XIVB)

Independently for Formulas (XIVA) and (XIVB), K is —CH$_2$— or —O—, and M is —O— or substituted nitrogen, provided that when M is substituted nitrogen, K is —CH$_2$—, the substituted nitrogen substituents being hydrogen, $C_1$-$C_{20}$ alkyl, or $C_1$-$C_{20}$ acyl, each $R_{25}$ being independently chosen for each occurrence from $C_1$-$C_{20}$ alkyl, $C_1$-$C_{10}$ alkoxy, hydroxy, and halogen, $R_{26}$ and $R_{27}$ each being independently hydrogen or $C_1$-$C_{20}$ alkyl, and u is an integer ranging from 0 to 2.

With some additional embodiments, B and B' of Formulas (I-A-PC) and (I-B-PC) are each independently selected from a group represented by the following Formula (XV):

(XV)

With reference to Formula (XV), $R_{28}$ is hydrogen or $C_1$-$C_{20}$ alkyl, and $R_{29}$ is an unsubstituted, mono-, or di-substituted group chosen from naphthyl, phenyl, furanyl, and thienyl, wherein the substituents are $C_1$-$C_{20}$ alkyl, $C_1$-$C_{20}$ alkoxy, or halogen.

In accordance with some alternative embodiments, B and B', independently for Formulas (I-A-PC) and (I-B-PC), taken together form one of a fluoren-9-ylidene, mono-, or di-substituted fluoren-9-ylidene, each of said fluoren-9-ylidene substituents being independently chosen from $C_1$-$C_{20}$ alkyl, $C_1$-$C_{20}$ alkoxy, and halogen.

In accordance with some additional embodiments, B and B' of Formulas (I-A-PC) and (I-B-PC) are each independently selected from phenyl, and phenyl substituted with at least one of fluoro, $C_1$-$C_6$ alkyl, $C_1$-$C_6$ alkoxy, morpholino, piperidino, and pyrrolidino.

With some embodiments, the photochromic fused ring indenopyran compound represented by Formula (I-A-PC) is prepared by reacting the fused ring indeno compound represented by Formula (I-A) with a propargyl alcohol represented by the following Formula (XI):

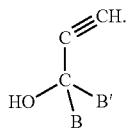

(XI)

With reference to Formula (XI), B and B' are as described herein with reference to Formulas (I-A-PC) and (I-B-PC).

With some further embodiments, the photochromic fused ring indenopyran compound represented by Formula (I-B-PC) is prepared by reacting the fused ring indeno compound represented by Formula (I-B) with the propargyl alcohol represented by Formula (XI).

With some embodiments, the photochromic fused ring indenopyran compound, such as represented by Formula (I-A-PC) or Formula (I-B-PC), is formed by reacting or coupling the propargyl alcohol represented by Formula XI and the fused ring indeno compound, such as represented by Formula (I-A) or Formula (I-B), in the presence of a catalytic amount of a protonic acid, such as dodecyl benzene sulfonic acid (DBSA) or para-toluene sulfonic acid (pTSA), in a suitable solvent, such as a haloalkyl (e.g., trichloromethane), under an inert atmosphere (e.g., a nitrogen sweep), and at a temperature range of from 0° C. to the boiling point of the solvent, such as from 0° C. to 55° C., or from 10° C. to 45° C., or from 20° C. to 25° C.

In accordance with some embodiments, the fused ring indeno compounds prepared by the methods of the present invention and certain intermediate compounds are used to prepare photochromic fused ring indeno-naphtho-pyran compounds, such as represented by the following Formula (I-C-PC) and Formula (I-D-PC):

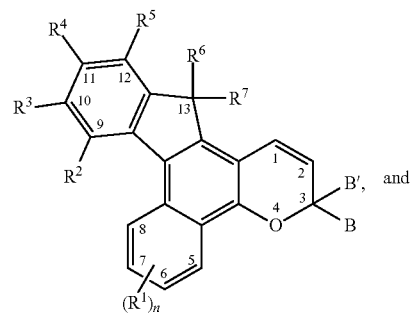

(I-C-PC)

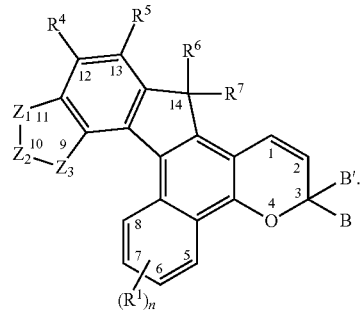

(I-D-PC)

With reference to Formulas (I-C-PC) and (I-D-PC), n, $R^1$-$R^7$, $Z_1$-$Z_3$, B and B' are each as described herein with reference to Formulas (I-A), (I-A-PC), and (I-B-PC). With reference to Formula (I-D-PC), the ring that includes $Z_1$-$Z_3$ is bonded to the ring positions of the indeno portion of the fused ring indeno-naphtho-pyran as depicted with reference to Formula (I-D-PC).

With some embodiments, the photochromic fused ring indenopyran compound represented by Formula (I-C-PC) is prepared by reacting the fused ring indeno compound represented by Formula (I-C) with the propargyl alcohol represented by Formula (XI).

With some further embodiments, the photochromic fused ring indenopyran compound represented by Formula (I-D-PC) is prepared by reacting the fused ring indeno compound represented by Formula (I-D) with the propargyl alcohol represented by Formula (XI).

In accordance with some embodiments, the fused ring indeno compounds prepared by the methods of the present invention and certain intermediate compounds are used to prepare photochromic fused ring indenopyran compounds, such as represented by the following Formula (I-E-PC) and Formula (I-G-PC):

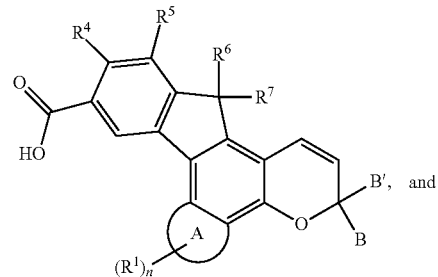

(I-E-PC)

-continued

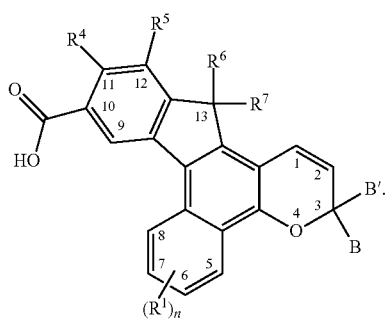

(I-G-PC)

With reference to Formulas (I-E-PC) and (I-G-PC), Ring-A, n, $R^1$, $R^4$-$R^7$, B and B' are each as described herein with reference to Formula (I-A) and (I-A-PC). With reference to Formula (I-G-PC), the carboxylic acid is bonded to Ring Position 10.

With some embodiments, the photochromic fused ring indenopyran compound represented by Formula (I-E-PC) is prepared by reacting the fused ring indeno compound represented by Formula (I-E) with the propargyl alcohol represented by the following Formula (XI).

With some embodiments, the photochromic fused ring indenopyran compound represented by Formula (I-G-PC) is prepared by reacting the fused ring indeno compound represented by Formula (I-G) with the propargyl alcohol represented by the following Formula (XI).

The photochromic compounds, with some embodiments, are used to prepare photochromic articles that include one or more such photochromic compounds. The photochromic articles are, with some embodiments, prepared by art-recognized methods, such as by imbibition methods, cast-in-place methods, coating methods, in-mold coating methods, over-mold methods, and lamination methods.

With some embodiments the photochromic articles are selected from ophthalmic articles, display articles, windows, mirrors, and active liquid crystal cell articles, and passive liquid crystal cell articles. With some further embodiments, the photochromic article is selected from ophthalmic articles, and the ophthalmic articles are selected from corrective lenses, non-corrective lenses, contact lenses, intraocular lenses, magnifying lenses, protective lenses, and visors. With some further embodiments, the photochromic article is selected from display articles, and the display articles are selected from screens, monitors, and security elements.

The present invention is more particularly described in the following examples, which are intended as illustrative only, since numerous modifications and variations therein will be apparent to those skilled in the art.

EXAMPLES

Example 1

Step 1

Into a flask containing benzoyl chloride (206 g) and dichloromethane (2 L) was added aluminum chloride (200 g) while stirring. After 30 minutes at ambient temperature the flask was placed in a water bath and a condenser was connected through which 2-methylfuran (210 mL) was added dropwise over 30 minutes. The resulting mixture was stirred for 7 hours then carefully poured into cold water (3 L). The organic layer was collected, washed with water and concentrated to afford (5-methylfuran-2-yl)(phenyl)methanone as an oily product (220 g).

Step 2

The product of Step 1 (220 g), dimethyl succinate (242 mL) and toluene (2.5 L) were added to a reaction flask equipped with a mechanical stirrer, a solid addition funnel and a Nitrogen blanket. Potassium t-butoxide (176 g) was added through the solid addition funnel and the mixture was stirred at room temperature for 3 hours. The resulting mixture was poured into water (2 L) and the aqueous layer was collected. The toluene layer was extracted with water (200 mL). The aqueous layers were combined and washed with toluene. Aqueous HCl (3N) was added to the water solution to adjust the pH to 5. The resulting solution was extracted with ethyl acetate. The ethyl acetate layer was then washed with brine (500 mL) and concentrated. The residue was then purified through a silica gel plug eluting with a mixture of 1/1 toluene/ethyl acetate, collecting the fractions containing the product. After evaporation of the solvents, a dense oily material was obtained (203 g).

Step 3

Anhydrous lanthanum (III) chloride (91 g) was ground to very fine powder then mixed with lithium chloride (47 g) and dry THF (1.5 L) in a 5 L three-neck flask equipped with a mechanical stirrer and an addition funnel. The mixture was refluxed until completely dissolved. The product from Step 2 (54 g) was dissolved in the mixture, then cooled to -5° C. A solution of 3M methyl magnesium chloride in dry THF (375 mL) was placed in the addition funnel. The first 100 mL of the Grignard was added to the mixture slowly, observing gas bubbles and an exotherm. After reducing the temperature back to -5° C., the remainder of the Grignard was added over 3 minutes. After stirring 30 minutes at -5° C., the ice bath was removed and the mixture was stirred at room temperature for one hour. The reaction mixture was then poured into a flask containing cold water (350 mL) and the pH adjusted to 4 using 12 M HCl (25 mL). The water layer was discarded and the organic layer was washed twice with brine and concentrated to dry. The resulting solid was re-dissolved in toluene and purified through a silica gel plug eluting with toluene. The clear solution was concentrated to dryness to obtain a dark oily product (41 g). $^1$H NMR showed that the product had a structure consistent with ~1/1 mixture of E/Z isomers of beta-((5-methylfuran-2-yl)(phenyl)methylene)-gamma,gamma-dimethyl-gamma-butyrolactone.

Step 4

The product from step 3 (5 g) and N-(4-bromophenyl)maleimide (5 g) were dissolved in acetic anhydride (50 mL) followed by addition of bismuth triflate (0.8 g). The reaction mixture was heated at 70° C. for 3 hours. The solvent was then removed by evaporation, and the resulting residue re-dissolved in dichloromethane and washed with water (100 mL). The organic layer was collected and purified through a silica gel plug eluting with a mixture of 5/1 hexanes/ethyl acetate, collecting the fractions containing the product. Removal of solvent yielded a solid product (9 g). $^1$H NMR showed that the product had a structure consistent with 11-(4-bromophenyl)-10,12-dioxo-7,7,9-trimethyl-7,10,11,12-tetrahydropyrrolo[3',4':4,5]indeno[3,2-a]naphthalen-5-yl acetate.

Example 2

The procedure from Example 1 was followed except maleic anhydride was used in place of N-(4-bromophenyl) maleimide to yield a yellow solid. $^1$H NMR showed that the product had a structure consistent with 10,12-dioxo-7,7,9-trimethyl-10,12-dihydro-7H-furo[3',4':4,5]indeno[3,2-a]naphthalen-5-yl acetate.

Example 3

Step 1

To a stirred mixture of aluminum chloride (187 g) and dichloromethane (1 L) at 0° C., was added a mixture of 2-furoyl chloride (160 g) and dichloromethane (100 ml) dropwise at a rate such that the temperature was maintained between 0° and 40° C., approximately 30 minutes. The mixture was stirred for an additional 30 minutes, then transferred to an addition funnel. The solution was added dropwise to a stirred solution of anisol (150 g) and dichloromethane (100 ml) in an ice bath over a period of one hour, maintaining a temperature below 20° C. After the addition, the mixture was stirred at 0° C. for 30 minutes, warmed to ambient temperature and stirred for one additional hour then poured onto ice (1 Kg). To the mixture was added 3N HCl (200 ml) and the mixture stirred at room temperature for two hours, after which the organic phase was collected. To the collected organic solution was added 2N aqueous NaOH (500 ml) and the mixture was stirred for two hours. The organic layer was collected, dried over magnesium sulfate and concentrated by evaporation to yield a clear liquid (278 g). $^1$H NMR showed that the product had a structure consistent with furan-2-yl(4-methoxyphenyl)methanone.

Step 2

The product of Step 1 (80 g), dimethyl succinic ester (115 g) and toluene (800 ml) were placed in a three-neck 3 L flask equipped with a mechanical stirrer. Potassium t-butoxide (67 g) was added in batches over a 30 minute period. An exothermic reaction was observed along with the formation of a large amount of precipitate. After a one hour hold, water (800 mL) was added and the mixture transferred to a separatory funnel. The aqueous phase was collected and washed twice with toluene (200 mL). The pH was adjusted to ~2 using 3N HCl, resulting in the separation of a large amount of oil. To the mixture was added ethyl acetate (500 mL). After stirring at ambient temperature for 10 minutes, the organic layer was collected, washed with brine and dried over MgSO$_4$. After concentration, the crude product was purified through a silica gel plug with the use of a gradient of 10/90 to 60/40 ethyl acetate/hexane as the eluent. A viscous oil (95 g) was obtained. $^1$H NMR showed that the obtained product (62 g) had a structure consistent with ~1/1 Z/E mixture of 4-(furan-2-yl)-3-(methoxycarbonyl)-4-(4-methoxyphenyl)but-3-enoic acid.

Step 3

A stock solution was prepared by mixing anhydrous lanthanum (III) chloride powder (147 g) and lithium chloride (76.2 g) in dry THF (2 L) and stirring for 3 days. The product of Step 2 (50 g) was dissolved in the stock solution (1 L) and cooled to 0° C. A solution of 2 M butyl magnesium chloride in THF (320 mL) was placed in the addition funnel. The first 30% of the Grignard was added slowly to the mixture, during which an exotherm was observed. Upon restoring the temperature to 0° C., the remainder of the Grignard was added over one minute. After stirring one hour at 0° C. and an additional hour at room temperature, the mixture was poured into ice water (0.5 L), and the pH adjusted to ~3 using 12 N HCl (~70 ml). The mixture turned clear with formation of two layers. The aqueous layer was discarded. The organic layer was washed with brine three times then concentrated to dryness. The crude product was purified through a silica gel plug with the use of toluene as eluent to yield a viscous oil (32 g). $^1$H NMR showed that the product had a structure consistent with a mixture of ~1/1 E/Z isomers of beta-((4-methoxyphenyl)(furan-2-yl)methylene)-gamma,gamma-dibutyl-gamma-butyrolactone.

Step 4

To a solution of maleic anhydride (0.8 g) in acetic anhydride (5 ml) was added the product from Step 3 (0.76 g), 2-phenylpropan-2-ol (0.7 g) and bismuth triflate (0.16 g). The mixture was stirred at room temperature for 48 hours followed by removal of solvent. The residue was purified by column separation using a CombiFlash® Rf from Teledyne ISCO to yield a viscous yellow oil (0.32 g). $^1$H NMR showed that the product had a structure consistent with 10,12-dioxo-7,7-dibutyl-3-methoxy-9-(2-phenylpropan-2-yl)-10,12-dihydro-7H-furo[3',4':4,5]indeno[3,2-a]naphthalen-5-yl acetate.

Example 4

Step 1

To a stirred mixture of benzoyl chloride (120 g), furan (100 mL) and dichloromethane (1 L) at 0° C. was added aluminum chloride (130 g) over one hour. The mixture was stirred at room temperature for two hours then poured slowly into water (1 L), then passed through Celite to remove the resulting brown precipitate. The organic layer was collected and concentrated. The crude product was purified by silica gel chromatography eluting with 2/8 ethyl acetate/hexane to yield a viscous oil (50 g). $^1$H NMR showed that the product had a structure consistent with furan-2-yl(phenyl)methanone.

Step 2

The procedure from Step 2 of Example 3 was followed except the product from Step 1 of this Example was used in place of the product from Step 1 of Example 3.

Step 3

The procedure from Step 3 of Example 3 was followed except methyl magnesium chloride was used in place of butyl magnesium chloride.

Step 4

The procedure from Step 4 of Example 3 was followed except N-(4-bromophenyl)maleimide was used in place of maleic anhydride. $^1$H NMR showed that the product had a structure consistent with 11-(4-bromophenyl)-10,12-dioxo- 7,7-dimethyl-9-(2-phenylpropan-2-yl)-7,10,11,12-tetrahydropyrrolo[3',4':4,5]indeno[3,2-a]naphthalen-5-yl acetate.

Example 5

The procedures from Example 4 were followed except maleic anhydride was used in place of N-(4-bromophenyl) maleimide in Step 4. $^1$H NMR showed that the product had a structure consistent with 10,12-dioxo-7,7-dimethyl-9-(2-phenylpropan-2-yl)-10,12-dihydro-7H-furo[3',4':4,5)indeno(3,2-a]naphthalen-5-yl acetate.

Example 6

Step 1

Into a dry flask containing 1M 4-fluorophenylmagnesium bromide in THF (450 mL) was added bis[2-(N,N-dimethylamino)-ethyl]ether (100 mL) with agitation. After stirring 40 minutes, the solution was slowly added to another flask containing a chilled solution (0° C.) of 2-furoyl chloride (53 mL) in THF (100 mL). The solution was stirred for 1 hour, followed by pouring carefully into cold water (300 mL). The aqueous layer was adjusted to pH 5 using 12M HCl (40 mL) followed by extraction with toluene (500 mL). To the organic layer was added aqueous NaOH (2M, 150 mL) followed by 2 hours of vigorous stirring. The aqueous layer was discarded and the organic layer washed with water (200 mL) and brine (200 mL). After evaporation of the solvents, the product with a structure corresponding to (4-fluorophenyl)(furan-2-yl)methanone was collected as an oily substance (76 g).

Step 2

The product from Step 1 (76 g), dimethyl succinate (78 mL) and toluene (500 mL) were added to a reaction flask equipped with a mechanical stirrer, a solid addition funnel and a Nitrogen blanket. Potassium t-butoxide (54 g) was added through the solid addition funnel and the mixture was stirred at room temperature for 2 hours. The resulting mixture was poured into 1 L of water and the aqueous layer was collected. The toluene layer was extracted with 350 mL water. The water layers were combined and washed with toluene. Aqueous HCl (3N) was added to the water solution to adjust pH 5. The resulting solution was extracted with ethyl acetate, washed with brine (300 mL) and concentrated. The residue was then purified through a silica gel plug eluting with a mixture of 1/1 toluene/ethyl acetate, collecting the fractions containing the product. After evaporation of the solvents, a dense oily material (110 g) was obtained.

Step 3

Anhydrous lanthanum (III) chloride (46 g) was ground to very fine powder then mixed with lithium chloride (24 g) and dry THF (1.5 L) in a 5 L three-neck flask equipped with a mechanical stirrer and an addition funnel. The mixture was refluxed until completely dissolved. The product from Step 2 (29 g) was dissolved in the mixture, then cooled to −5° C. A solution of 3 M methyl magnesium chloride in dry THF (600 mL) was placed in the addition funnel. The first 100 mL of the Grignard was dropped into the mixture slowly, observing gas bubbles and exotherm. After reducing the temperature back to −5° C., the remainder of the Grignard was added over 3 minutes. After stirring 30 minutes at −5° C., the ice bath was removed and the mixture was stirred at room temperature for one hour. The reaction mixture was then poured into a flask containing cold water (350 mL) and the pH adjusted to 4 using 12 M HCl (25 mL). The water layer was discarded and the organic layer was washed twice with brine then concentrated to dryness. The resultant solid was re-dissolved in toluene and purified through a silica gel plug eluting with toluene. The clear solution was concentrated to dryness to afford a dark oily product (41 g). $^1$H NMR showed that the product had a structure consistent with ~1/1 mixture of E/Z isomers of ~1/1 mixture of E/Z isomers of beta-((furan-2-yl)(4-fluorophenyl)methylene)-gamma,gamma-dimethyl-gamma-butyrolactone.

Step 4

The product from step 3 (5 g) and N-(4-bromophenyl) maleimide (5 g) were dissolved in acetic anhydride (50 mL) in a 1 L flask, followed by addition of dodecylbenzenesulfonic acid (26 mL), water (3.5 mL) and bismuth triflate (6.2 g). The mixture was heated for two hours under reflux. At this stage an aliquot of the reaction mixture was transferred to a vial and used for Example 6A. To the remaining reaction mixture was added acetic anhydride (50 mL). The mixture was stirred at 60° C. for 4 hours, cooled to ambient temperature and stirred an additional 8 hours. Water (200 mL) and 12 M HCl(aq) (45 mL) were carefully added and the reaction was refluxed for 2 hours. The mixture phase separated and the organic layer was collected, washed with water (250 mL), brine (150 mL) and concentrated. The resulting residue was purified through a silica gel plug eluting with a mixture of 15/1 toluene/ethyl acetate. The fractions containing the product were collected and concentrated to afford the solid product (30 g). $^1$H NMR showed that the product had a structure consistent with 10-carboxy-7,7-dimethyl-3-fluoro-7H-indeno[3,2-a]naphthalen-5-ol.

Example 6A

The transferred aliquot of the reaction mixture from Example 6 was dissolved in dichloromethane and washed with water. The organic layer was recovered and extracted with 2 M NaOH(aq). The aqueous layer was then collected, acidified and extracted with dichloromethane. The organic layer was collected, dried over magnesium sulfate and concentrated. An oily residue was obtained as the product. $^1$H NMR and mass spectrometry showed that the product had a structure consistent with 2-(carboxymethyl)-3-(4-fluorophenyl)-1,1-dimethyl-1H-indene-5-carboxylic acid.

Example 7

Step 1

To a solution of maleic anhydride (7.7 g) in toluene (100 mL) was added water (47 mg), dodecylbenzenesulfonic acid (8.5 g), beta-((4-methoxyphenyl)(furan-2-yl)methylene)-gamma,gamma-dibutyl-gamma-butyrolactone (10 g, the product from Step 3 of Example 3) and bismuth triflate (1.7 g). The mixture was stirred at room temperature for 24 hours, at which time HPLC indicated the reaction was complete. A small amount of the reaction mixture (~1 mL) was transferred to a 20 mL vial to be used for Example 7A. The remainder of the reaction mixture was used in the next step.

Step 2

To the remaining reaction mixture from Step 1 was added acetic anhydride (20 mL). The mixture was refluxed for one hour and then cooled to room temperature. Aqueous HCl (3N, 100 mL) was added and the mixture refluxed for 4 hours. The organic layer was collected, concentrated and purified by column separation using a CombiFlash Rf. A viscous brown oil (3.5 g), which solidified upon standing at room temperature was obtained. $^1$H NMR showed that the product had a structure consistent with 10-carboxy-7,7-dibutyl-3-methoxy-7H-indeno[3,2-a]naphthalen-5-ol.

Example 7A

The transferred portion of the reaction mixture (~1 mL) from Step 1 of Example 7 was adsorbed to silica gel (5 grams) and then purified by column separation using a CombiFlash Rf. The fractions with the major product were collected and concentrated to dryness yielding a viscous oil (50 mg). $^1$H NMR showed that the product had a structure consistent with 1,1-dibutyl-2-(carboxymethyl)-3-(4-methoxyphenyl)-1H-indene-5-carboxylic acid.

Example 8

The procedures from Steps 1 through 4 of Example 6 were followed except that ethyl magnesium chloride was used in place of methyl magnesium chloride in Step 3. $^1$H NMR showed that the product had a structure consistent with 10-carboxy-7,7-diethyl-3-fluoro-7H-indeno[3,2-a]naphthalen-5-ol.

Example 9

The procedures from Steps 1 through 4 of Example 6 were followed except that butyl magnesium chloride was used in place of methyl magnesium chloride in Step 3. $^1$H NMR showed that the product had a structure consistent with 10-carboxy-7,7-dibutyl-3-fluoro-7H-indeno[3,2-a]naphthalen-5-ol.

Example 10

Step 1

Magnesium (17 g) was placed in a dry flask equipped with a dropping funnel containing a mixture of 1-bromo-3,5-difluorobenzene (80 mL) and THF (200 mL). 60 mL of the solution was added to the flask. Within a few minutes, the solvent began to boil. The remainder of the solution in the dropping funnel was added dropwise, controlling the temperature with an ice bath. After the addition, the mixture was stirred at room temperature for two hours, then cooled to 0° C. followed by addition of bis[2-(N,N-dimethylamino)ethyl]ether (135 mL). This mixture was stirred for 30 minutes then slowly poured into a flask containing a chilled solution of 2-furoyl chloride (68 mL) in THF (200 mL). The mixture was stirred for 8 hours at ambient temperature, followed by addition of ice water (600 mL). The aqueous layer was adjusted to pH 5 with 3N HCl(aq), then removed. To the organic layer was added 150 mL of NaOH (aq, 2M) and the mixture was stirred vigorously for 2 hours, after which the aqueous layer was discarded and the organic layer was washed with water (300 mL) and brine (200 mL). After evaporation of the solvents the product with a structure corresponding to (3,5-difluorophenyl)(furan-2-yl)methanone was collected as an oily substance (109 g).

Step 2

Steps 2 through 4 from Example 6 were followed except in Step 2, the product from Step 1 above was used in place of the product from Step 1 of Example 6. $^1$H NMR showed that the product had a structure consistent with 10-carboxy-2,4-difluoro-7,7-dimethyl-7H-indeno[3,2-a]naphthalen-5-ol.

Example 11

Step 1

1,3,5-tribromobenzene (500 g) was dried in a vacuum oven until sublimation occurred. The material was then dissolved in THF (2 L) and the mixture was cooled to −20° C. using a NaCl/ice bath. A 2M solution of isopropyl magnesium chloride in THF (800 mL) was added dropwise, during which time the mixture darkened and began to exotherm. The addition was continued over one hour, maintaining the temperature between −10 to −5° C. The mixture was stirred for an additional 20 minutes in the ice bath, followed by slow addition of bis[2-(N,N-dimethylamino)-ethyl]ether (364 mL) while keeping the temperature below 0° C. After the addition, the mixture was stirred for 20 minutes then a solution of 2-furoyl chloride (156 mL) in THF (100 mL) was added. The mixture was left to stir in an ice bath for 12 hours, followed by stirring at room temperature for 24 hours. The mixture was poured into ice water (3 L). The aqueous layer was adjusted to pH 5 with 3N HCl(aq), then discarded. To the organic layer was added 400 mL of 2M NaOH(aq) and the mixture was stirred vigorously for 2 hours, after which the aqueous layer was discarded and the organic layer was washed with water (1 L) and brine (500 mL). After evaporation of the solvents, the product with a structure corresponding to (3,5-dibromophenyl)(furan-2-yl)methanone was collected as a dark oily substance (465 g).

Step 2

Steps 2 through 4 from Example 6 were followed except that in Step 2, the product from Step 1 above was used in place of the product from Step 1 of Example 6. $^1$H NMR showed that the product had a structure consistent with 10-carboxy-2,4-dibromo-7,7-dimethyl-7H-indeno[3,2-a]naphthalen-5-ol.

Example 12

Steps 1 and 2 from Example 7 were followed except that methyl magnesium chloride was used in place of butyl magnesium chloride. $^1$H NMR showed that the product had a structure consistent with 10-carboxy-7,7-dimethyl-3-methoxy-7H-indeno[3,2-a]naphthalen-5-ol.

Example 13

Steps 1 through 4 from Example 6 were followed except in Step 1, p-toluylmagnesium bromide was used in place of 4-fluorophenylmagnesium bromide. $^1$H NMR showed that the product had a structure consistent with 10-carboxy-7,7-dimethyl-3-methyl-7H-indeno[3,2-a]naphthalen-5-ol.

Example 14

Steps 1 through 4 from Example 6 were followed except 4-trifluoromethylphenylmagnesium bromide was used in place of 4-fluorophenylmagnesium bromide in Step 1. $^1$H NMR showed that the product had a structure consistent with 10-carboxy-7,7-dimethyl-3-trifluoromethyl-7H-indeno[3,2-a]naphthalen-5-ol.

Example 15

Step 1

The procedure from Step 1 of Example 10 was followed except that 4-bromo-1-methoxy-2-methylbenzene was used in place of 1-Bromo-3,5-difluorobenzene.
Steps 2 Through 4
Steps 2 through 4 from Example 6 were followed except in Step 2, the product from Step 1 above was used in place of the product from Step 1 of Example 6 and in Step 3, n-butyl magnesium chloride was used in place of methyl magnesium chloride. $^1$H NMR showed that the product had a structure consistent with 10-carboxy-7,7-dibutyl-3-methoxy-2-methyl-7H-indeno[3,2-a]naphthalen-5-ol.

Example 16

Steps 1 through 4 from Example 6 were followed except that in Step 1, phenyl magnesium bromide was used in place of 4-fluorophenylmagnesium bromide. $^1$H NMR showed the product had a structure consistent with 10-carboxy-7,7-dimethyl-7H-indeno[3,2-a]naphthalen-5-ol.

Example 17

Steps 1 through 4 from Example 6 were followed except in Step 1, phenyl magnesium bromide was used in place of 4-fluorophenylmagnesium bromide and in Step 3, n-butyl magnesium chloride was used in place of methyl magnesium chloride. $^1$H NMR showed that the product had a structure consistent with 10-carboxy-7,7-dibutyl-7H-indeno[3,2-a]naphthalen-5-ol.

Example 18

Step 1

The product from Example 1 (3 g) was dissolved in ethanol (70 mL) and 12 M HCl (aq, 0.2 mL) was added. The mixture was refluxed for 1 hour then cooled to ambient temperature. The solvent was removed by evaporation. The resulting residue was dissolved in dichloromethane (100 mL), washed once with water (100 mL) and concentrated to dryness to yield a solid product (2.6 g). $^1$H NMR showed that the product had a structure consistent with 11-(4-bromophenyl)-10,12-dioxo-7,7,9-trimethyl-7,10,11,12-tetrahydropyrrolo[3',4':4,5]indeno[3,2-a]naphthalene-5-ol.

Step 2

The product from Step 1 (3 g) was dissolved in 1,2-dichloroethane (150 mL). To the flask was added 1-(4-butoxyphenyl)-1-phenylprop-2-yn-1-ol (2 g) and a few crystals of p-toluenesutfonic acid. The mixture was stirred at room temperature for three hours. The reaction mixture was washed once with water (50 mL) and the organic residue was purified by silica gel chromatography eluting with 4/1 hexanes/ethyl acetate, collecting the fractions containing the product. After evaporation of the solvents, the product was further purified using a CombiFlash Rf, yielding yellow crystals (0.9 g). $^1$H NMR analysis indicated that the product had a structure consistent with 10-(4-bromophenyl)-3-(4-butoxyphenyl)-12,14,14-trimethyl-9,11-dioxo-3-phenyl-3,9,11,14-tetrahydropyrrolo[3',4':4,5]indeno[2',3':3,4]naphtho[1,2-b]pyran.

Example 19

The procedure from Example 18 was used except the product from Example 5 was used in place of the product from Example 1 in Step 1 and 1-(4-methoxyphenyl)-1-phenylprop-2-yn-1-ol was used in place of 1-(4-butoxyphenyl)-1-phenylprop-2-yn-1-ol in Step 2. $^1$H NMR analysis showed the product had a structure consistent with 10-(4-bromophenyl)-3-(4-methoxyphenyl)-14,14-dimethyl-9,11-dioxo-3-phenyl-12-(2-phenylpropan-2-yl)-3,9,11,14-tetrahydropyrrolo[3',4':4,5]indeno[2',3':3,4]naphtho[1,2-b]pyran.

Example 20

The procedure from Example 18 was used except the product from Example 5 was used in place of the product from Example 1 in Step 1, and 1-(4-methoxyphenyl)-1-phenylprop-2-yn-1-ol was used in place of 1-(4-butoxyphenyl)-1-phenylprop-2-yn-1-ol in Step 2. $^1$H NMR analysis showed the product had a structure consistent with 3-(4-methoxyphenyl)-14,14-dimethyl-9,11-dioxo-3-phenyl-12-(2-(2-phenylpropan-2-yl))-3,9,11,14-tetrahydrofuro[3',4':4,5]indeno[2',3':3,4]naphtho[1,2-b]pyran.

Example 21

The naphthol product from Example 17 (4.2 g) was placed in a reaction flask. To the flask was added 1-(4-butoxyphenyl)-1-(4-fluorophenyl)prop-2-yn-1-ol (4 g), p-toluenesulfonic acid (0.2 g) and dichloroethane (100 mL). The mixture was stirred and refluxed for one hour, followed by removal of solvent. The residue was purified using a CombiFlash Rf eluted with a gradient of 1/9-5/5 ethyl acetate/hexane, yielding a viscous reddish oil (3.2 g). $^1$H NMR analysis showed the product had a structure consistent with 10-carboxy-3-(4-fluorophenyl)-3-(4-butoxyphenyl)-13,13-dibutyl-3,13-dihydro-indeno[2',3':3,4]naphtho[1,2-b]pyran.

Example 22

The naphthol product from Example 9 (2.2 g) was placed in a reaction flask. To the flask was added 1-(4-(N-morpholino)phenyl)-1-phenylprop-2-yn-1-ol (4 g), dodecylbenzenesulfonic acid (0.27 g) and dichloroethane (30 mL). The mixture was stirred and refluxed for 2 hours, followed by removal of all solvent. The residue was purified using a CombiFlash Rf eluted with 1/9-5/5 ethyl acetate/hexane to yield a viscous oil (2.5 g). $^1$H NMR analysis showed the product had a structure consistent with 10-carboxy-6-fluoro-3-(4-(N-morpholino)phenyl)-3-phenyl-13,13-dibutyl-3,13-dihydro-indeno[2',3':3,4]naphtho[1,2-b]pyran.

Example 23

The naphthol product from Example 7 (1.2 g) was placed in a reaction flask. To the flask was added 1-(4-methoxyphenyl)-1-(4-fluorophenyl)prop-2-yn-1-ol (1 g), dodecylbenzenesulfonic acid (0.1 g) and dichloroethane (20 mL). The mixture was stirred and refluxed for 2 hours, followed by removal of all solvent. The residue was purified using a CombiFlash eluted with 0/9-25/75 ethyl acetate/hexane to yield a viscous oil (1.3 g). $^1$H NMR analysis showed the product had a structure consistent with 10-carboxy-6-methoxy-3-(4-fluorophenyl)-3-(4-methoxyphenyl)-13,13-dibutyl-3,13-dihydro-indeno[2',3':3,4]naphtho[1,2-b]pyran.

Example 24

The procedure from Example 22 was used except the naphthol product from Example 14 was used in place of the naphthol from Example 9. $^1$H NMR analysis showed the product had a structure consistent with 10-carboxy-3-(4-(N-morpholino)phenyl)-3-phenyl-6-trifluoromethyl-13,13-dimethyl-3,13-dihydro-indeno[2',3':3,4]naphtho[1,2-b]pyran.

Example 25

The procedure from Example 22 was used except the naphthol product from Example 13 was used in place of the naphthol from Example 9 and 1-(4-butoxyphenyl)-1-(4-(N-morpholino)phenyl)-prop-2-yn-1-ol was used in place of 1-(4-(N-morpholino)phenyl)-1-phenylprop-2-yn-1-ol. $^1$H NMR analysis showed the product had a structure consistent with 10-carboxy-3-(4-butoxyphenyl)-3-(4-(N-morpholino)phenyl)-methyl-13,13-dimethyl-3,13-dihydro-indeno[2',3':3,4]naphtho[1,2-b]pyran.

Example 26

The procedure from Example 22 was used except the naphthol product from Example 10 was used in place of the naphthol from Example 9 and 1-(4-fluorophenyl)-1-(4-(N-morpholino)phenyl)-prop-2-yn-1-ol was used in place of 1-(4-(N-morpholino)phenyl)-1-phenylprop-2-yn-1-ol. $^1$H NMR analysis showed the product had a structure consistent with 10-carboxy-5,7-difluoro-3-(4-fluorophenyl)-3-(4-(N-morpholino)phenyl)-13,13-dimethyl-3,13-dihydro-indeno[2',3':3,4]naphtho[1,2-b]pyran.

Example 27

A solution containing the product from Example 1 (1 g), 4-(trans-4-pentylcyclohexyl)-N-(4-(4,4,5,5-tetramethyl-1,3,2-dioxaborolan-2-yl)phenyl)benzamide (1 g) and K$_2$CO$_3$ (1.5 g) in 1,2-dimethoxyethane (70 mL) and water (30 mL) was stirred and sparged with Nitrogen for 10 minutes, followed by addition of bis(triphenylphosphine)palladium (II)dichloride (0.13 g). The reaction mixture was heated to reflux for 8 hours, followed by extraction with ethyl acetate (100 mL). The organic phase was collected and concentrated. The residue was purified through a silica gel plug to yield a solid product (1.2 g). $^1$H NMR showed that the product had a structure consistent with 11-(4'-(4-(trans-4-pentylcyclohexyl)benzamido)-[1,1'-biphenyl])-10,12-dioxo-7,7,9-trimethyl-7,10,11,12-tetrahydropyrrolo[3',4':4,5]indeno[3,2-a]naphthalen-5-ol.

The present invention has been described with reference to specific details of particular embodiments thereof. It is not intended that such details be regarded as limitations upon the scope of the invention except insofar as to the extent that they are included in the accompanying claims.

What is claimed is:
1. A method of forming a fused ring indeno compound, which is an intermediate for preparation of a photochromic compound, wherein said fused ring indeno compound is represented by Formula (I-E),

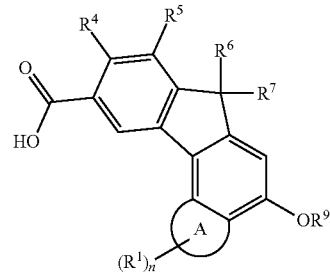

(I-E)

wherein,

Ring-A is selected from aryl and fused ring aryl, n is selected from 1 to 8, $R^1$ for each n is independently selected from hydrogen, hydrocarbyl and substituted hydrocarbyl each optionally and independently interrupted with at least one of —O—, —S—, —C(O)—, —C(O)O—, —S(O)—, —SO$_2$—, —N=N—, —N(R$_{11}$')— where R$_{11}$' is selected from hydrogen, hydrocarbyl or substituted hydrocarbyl, —Si(OR$_8$')$_w$(R$_8$')$_t$—, where w and t are each independently selected from 0 to 2, provided that the sum of w and t is 2, and each R$_8$' is independently selected from hydrogen, hydrocarbyl and substituted hydrocarbyl, and combinations of two or more thereof; halogen; cyano; —O—R$_{10}$', or —S—R$_{10}$', or —C(O)—R$_{10}$' or —C(O)—OR$_{10}$', wherein each R$_{10}$' is independently selected from hydrogen, hydrocarbyl or substituted hydrocarbyl; perhalohydrocarbyl; and —C(O)—N(R$_{11}$')(R$_{12}$') or —N(R$_{11}$')R$_{12}$', wherein R$_{11}$' and R$_{12}$' are each independently selected from hydrogen, hydrocarbyl or substituted hydrocarbyl, or R$_{11}$' and R$_{12}$' together form a ring structure optionally including at least one heteroatom, $R^4$ and $R^5$ are each independently selected from hydrogen, hydrocarbyl, substituted hydrocarbyl, halogen, —C(O)—N(R$_{14}$)(R$_{15}$), —N(R$_{14}$)(R$_{15}$), —SR$_{16}$, and —OR$_{16}$, where R$_{14}$ and R$_{15}$ are each independently selected from hydrogen, hydrocarbyl, and substituted hydrocarbyl, or R$_{14}$ and R$_{15}$ together form a ring, and each R$_{16}$ is independently selected from hydrocarbyl and substituted hydrocarbyl, $R^6$ and $R^7$ are each independently selected from hydrogen, hydrocarbyl, and substituted hydrocarbyl, each optionally and independently interrupted with —O—, —S—, —N(R$_{11}$')—, where R$_{11}$' is selected from hydrogen, hydrocarbyl or substituted hydrocarbyl, and $R^9$ is selected from —C(O)—R$_{19}$ and —S(O)(O)R$_{19}$, wherein R$_{19}$ is selected from hydrocarbyl, and halohydrocarbyl, said method comprising, (a) in a first step, reacting together maleic anhydride and a lactone compound represented by Formula (III-A), in the presence of a catalyst, and a solvent, said solvent being substantially free of reaction with water, thereby forming an acid intermediate represented by Formula (VIII-A),

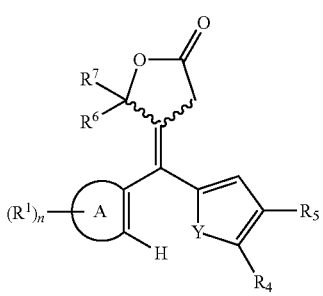

(III-A)

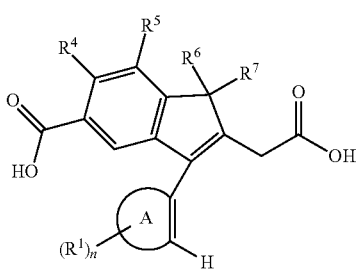

(VIII-A)

wherein for said lactone compound represented by Formula (III-A) and for said acid intermediate represented by Formula (VIII-A), Ring-A, n, $R^1$, $R^4$, $R^5$, $R^6$, and $R^7$ are each as described with regard to said fused ring indeno compound represented by Formula (I-E), and Y of Formula (III-A) is selected from O, S, and $N(R_{18})$, where $R_{18}$ is selected from hydrogen, hydrocarbyl, and substituted hydrocarbyl, and (b) in a second step, converting said acid intermediate represented by Formula (VIII-A) to said fused ring indeno compound represented by Formula (I-E) in the presence of a material selected from carboxylic acid halide, carboxylic acid anhydride, sulfonyl halide, sulfonyl anhydride, and combinations thereof.

2. The method of claim 1 wherein,
in said first step,
said catalyst is selected from at least one Lewis acid represented by Formula (V) and Formula (VI), $$M^{y+}(^-O\!-\!SO_2\!-\!R_{20})_y \qquad (V)$$

and $$M^{y+}(X^-)_y \qquad (VI)$$

wherein independently for each of Formula (V) and Formula (VI), M represents a metal, y is the valence of the metal, $R_{20}$ for each y is independently selected from hydrocarbyl and halohydrocarbyl, and X for each y is independently selected from halogen; and
said solvent is selected from aromatic hydrocarbon solvents, haloalkyl solvents, perhaloalkyl solvents, cyano alkyl solvents, and nitro alkyl solvents.

3. The method of claim 2 wherein,
in said first step,
the metal M of Formula (V) and Formula (VI) is independently selected from Bi, B, Al, Hf, Sc, Cu, Yb, Ti, Sn, Fe, Zn, Ag, Y, In, Nb and Mg, $R_{20}$ is selected from $C_1$-$C_{10}$ linear or branched alkyl, and $C_1$-$C_{10}$ linear or branched perfluoroalkyl, and X is selected from I, F, Cl, and Br; and said solvent is selected from benzene, xylene, toluene, methylene chloride, chloroform, 2-dichloroethane, acetonitrile, nitromethane and combinations of two or more thereof.

4. The method of claim 1 wherein said first step is conducted in the presence of an acid selected from alkyl sulfonic acid, aryl sulfonic acid, and combinations thereof.

5. The method of claim 4 wherein said acid is selected from p-toluene sulfonic acid, dodecylbenzenesulfonic acid, and combinations thereof.

6. The method of claim 1 further comprising, after said second step,
in a third step, hydrolyzing said intermediate represented by Formula (VIII-A) in the presence of a protonic acid or a base, thereby forming an indeno compound represented by Formula (I-F),

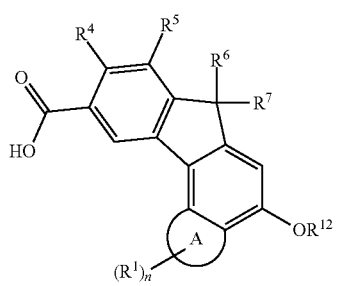

(I-F)

wherein $R^{12}$ is hydrogen.

7. The method of claim 6 wherein said protonic acid is selected from carboxylic acids, sulfonic acids, phosphoric acids, hydrogen halides, and combinations thereof.

8. The method of claim 1 wherein,
Ring-A, for Formula (I-E), Formula (III-A), and Formula (VIII-A) is selected from aryl;
$R^1$, for Formula (I-E), Formula (III-A), and Formula (VIII-A), for each n is independently selected from,
hydrogen,
halogen selected from bromo, iodo, fluoro and chloro;
$C_1$-$C_{20}$ linear or branched alkyl;
$C_3$-$C_{10}$ cycloalkyl;
substituted or unsubstituted phenyl, the phenyl substituents being selected from halogen, halo($C_1$-$C_{20}$) alkyl, $C_1$-$C_{20}$ alkyl or $C_1$-$C_{20}$ alkoxy;
—O—$R_{10}$', or —S—$R_{10}$' or —C(O)—$R_{10}$' or —C(O)—O$R_{10}$', wherein each $R_{10}$' is independently selected from hydrogen, $C_1$-$C_{20}$ alkyl, phenyl($C_1$-$C_{20}$)alkyl, mono($C_1$-$C_{20}$)alkyl substituted phenyl ($C_1$-$C_{20}$)alkyl, mono($C_1$-$C_{20}$)alkoxy substituted phenyl($C_1$-$C_{20}$)alkyl, ($C_1$-$C_{20}$)alkoxy($C_2$-$C_{20}$)alkyl, $C_3$-$C_{10}$ cycloalkyl, or mono($C_1$-$C_{20}$)alkyl substituted $C_3$-$C_{10}$ cycloalkyl;
—N($R_{11}$')$R_{12}$', or —C(O)—N($R_{11}$')($R_{12}$'), wherein $R_{11}$' and $R_{12}$' are each independently hydrogen, $C_1$-$C_{20}$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$-$C_{20}$ alkylaryl, $C_3$-$C_{10}$ cycloalkyl, $C_4$-$C_{20}$ bicycloalkyl, $C_5$-$C_{20}$ tricycloalkyl or $C_1$-$C_{20}$ alkoxyalkyl, wherein said aryl group is phenyl or naphthyl, or $R_{11}$' and $R_{12}$' come together with the nitrogen atom to form a $C_3$-$C_{20}$ hetero-bicycloalkyl ring or a $C_4$-$C_{20}$ hetero-tricycloalkyl ring;

a nitrogen containing ring represented by graphic formula XIIA,

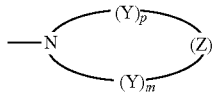

wherein each —Y— is independently chosen for each occurrence from —CH$_2$—, —CH(R$_{13}$')—, —C(R$_{13}$')$_2$—, —CH(aryl)-, —C(aryl)$_2$-, and —C(R$_{13}$')(aryl)-, and Z is —Y—, —O—, —S—, —NH—, —N(R$_{13}$')—, or —N(aryl)-, wherein each R$_{13}$' is independently C$_1$-C$_{20}$ alkyl, each aryl is independently phenyl or naphthyl, m is an integer 1, 2 or 3, and p is an integer 0, 1, 2, or 3 and provided that when p is 0, Z is —Y—;

a group represented by one of the following graphic formulas XIIB or XIIC,

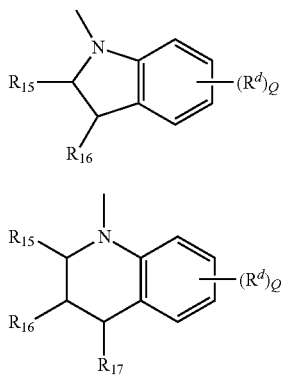

wherein R$_{15}$, R$_{16}$, and R$_{17}$ are each independently hydrogen, C$_1$-C$_{20}$ alkyl, phenyl, or naphthyl, or the groups R$_{15}$ and R$_{16}$ together form a ring of 5 to 8 carbon atoms and each R$^d$ is independently for each occurrence selected from C$_1$-C$_{20}$ alkyl, C$_1$-C$_{20}$ alkoxy, fluoro or chloro, and Q is an integer 0, 1, 2, or 3; and unsubstituted, mono-, or di-substituted C$_4$-C$_{18}$ spirobicyclic amine, or unsubstituted, mono-, and di-substituted C$_4$-C$_{18}$ spirotricyclic amine, wherein said substituents are independently aryl, C$_1$-C$_{20}$ alkyl, C$_1$-C$_{20}$ alkoxy, or phenyl(C$_1$-C$_{20}$)alkyl; or two adjacent R$^1$ groups together form a group represented by one of XIID and XIIE:

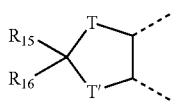

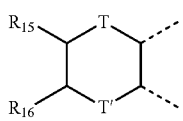

wherein T and T' are each independently oxygen or the group —NR$_{11}$'—, where R$_{11}$', R$_{15}$, and R$_{16}$ are as set forth above;

R$^4$ and R$^5$, for Formula (I-E), Formula (III-A), and Formula (VIII-A), are each independently selected from,
hydrogen,
halogen selected from F, Cl, Br, and I,
C$_1$-C$_{20}$ linear or branched alkyl;
C$_3$-C$_{10}$ cycloalkyl;
substituted or unsubstituted phenyl, the phenyl substituents being selected from hydroxyl, halogen, carbonyl, C$_1$-C$_{20}$ alkoxycarbonyl, cyano, halo(C$_1$-C$_{20}$)alkyl, C$_1$-C$_{20}$ alkyl or C$_1$-C$_{20}$ alkoxy;
—C(O)N(R$_{14}$)(R$_{15}$), or —N(R$_{14}$)(R$_{15}$), where R$_{14}$ and R$_{15}$ are each independently selected from,
hydrogen,
C$_1$-C$_{20}$ linear or branched alkyl;
C$_3$-C$_{10}$ cycloalkyl; and
substituted or unsubstituted phenyl, the phenyl substituents being selected from hydroxyl, halogen, carbonyl, C$_1$-C$_{20}$ alkoxycarbonyl, cyano, halo(C$_1$-C$_{20}$)alkyl, C$_1$-C$_{20}$ alkyl or C$_1$-C$_{20}$ alkoxy;
or R$_{14}$ and R$_{15}$ together form a ring; and
—OR$_{16}$, or —SR$_{16}$, where each R$_{16}$ is independently selected from,
C$_1$-C$_{20}$ linear or branched alkyl;
C$_3$-C$_{10}$ cycloalkyl; and
substituted or unsubstituted phenyl, the phenyl substituents being selected from halogen, halo(C$_1$-C$_{20}$)alkyl, C$_1$-C$_{20}$ alkyl or C$_1$-C$_{20}$ alkoxy;

R$^6$ and R$^7$, for Formula (I-E), Formula (III-A), and Formula (VIII-A), are each independently selected from,
(i) hydrogen, C$_1$-C$_{20}$ alkyl, C$_1$-C$_{20}$ haloalkyl, C$_3$-C$_{10}$ cycloalkyl, allyl, benzyl, or mono-substituted benzyl, said benzyl substituents being chosen from halogen, C$_1$-C$_{20}$ alkyl or C$_1$-C$_{20}$ alkoxy;
(ii) an unsubstituted, mono- di- or tri-substituted group chosen from phenyl, naphthyl, phenanthryl, pyrenyl, quinolyl, isoquinolyl, benzofuranyl, thienyl, benzothienyl, dibenzofuranyl, dibenzothienyl, carbazolyl, or indolyl, said group substituents in each case being independently chosen from halogen, C$_1$-C$_{20}$ alkyl or C$_1$-C$_{20}$ alkoxy;
(iii) mono-substituted phenyl, said substituent located at the para position being —(CH$_2$)$_t$— or —O—(CH$_2$)$_t$—, wherein t is the integer 1, 2, 3, 4, 5 or 6, said substituent being connected to an aryl group which is a member of a photochromic material;
(iv) the group —CH(R$^{10}$)G, wherein R$^{10}$ is hydrogen, C$_1$-C$_6$ alkyl or the unsubstituted, mono- or di-substituted aryl groups phenyl or naphthyl, and G is —CH$_2$OR$^{11}$, wherein R$^{11}$ is hydrogen, C$_1$-C$_{20}$ alkyl, C$_1$-C$_{20}$ alkoxy(C$_1$-C$_{20}$)alkyl, phenyl(C$_1$-C$_{20}$)alkyl, mono(C$_1$-C$_{20}$)alkoxy substituted phenyl(C$_1$-C$_{20}$)alkyl, or the unsubstituted, mono- or di-substituted aryl groups phenyl or naphthyl, each of said phenyl and naphthyl group substituents being C$_1$-C$_{20}$ alkyl or C$_1$-C$_{20}$ alkoxy; or
(v) R$^6$ and R$^7$ together form a spiro substituent selected from a substituted or unsubstituted spiro-carbocyclic ring containing 3 to 6 carbon atoms, a substituted or unsubstituted spiro-heterocyclic ring containing 1 or 2 oxygen atoms and 3 to 6 carbon atoms including the spirocarbon atom, said spiro-carbocyclic ring and spiro-heterocyclic ring being annellated with 0, 1 or 2 benzene rings, said substituents being hydrogen or $C_1$-$C_{20}$ alkyl; and $R^9$ for Formula (I-E) is selected from —C(O)—$R_{19}$ and —S(O)(O)$R_{19}$, wherein $R_{19}$ is selected from $C_1$-$C_{20}$ linear or branched alkyl and $C_1$-$C_{20}$ linear or branched perfluoroalkyl.

9. The method of claim 8 wherein,

Ring-A, for Formula (I-E), Formula (Ill-A), and Formula (VIII-A), is $C_6$-aryl, $R^1$, for Formula (I-E), Formula (III-A), and Formula (VIII-A), for each n is independently selected from hydrogen, $C_1$-$C_6$ linear or branched alkyl, $C_3$-$C_7$ cycloalkyl, $C_1$-$C_5$ haloalkyl, fluoro, chloro, and —O—$R_{10}$';

$R^4$ and $R^5$, for Formula (I-E), Formula (III-A), and Formula (VIII-A), are each independently selected from, hydrogen;

$C_1$-$C_6$ linear or branched alkyl;

$C_3$-$C_7$ cycloalkyl; and substituted or unsubstituted phenyl, the phenyl substituents being selected from halogen, halo($C_1$-$C_6$) alkyl, $C_1$-$C_6$ alkyl or $C_1$-$C_6$ alkoxy;

$R^6$ and $R^7$, for Formula (I-E), Formula (III-A), and Formula (VIII-A), are each independently selected from hydrogen, $C_1$-$C_8$ alkyl, $C_1$-$C_8$ haloalkyl, and $C_3$-$C_7$ cycloalkyl, or $R^3$ and $R^4$ together form a spiro substituent selected from a substituted or unsubstituted spiro-carbocyclic ring containing 3 to 6 carbon atoms; and $R^9$ for Formula (I-E) is selected from —C(O)—$R_{19}$.

10. The method of claim 1 wherein, the fused ring indeno compound represented by Formula (I-E) is represented by Formula (I-G), (I-G)

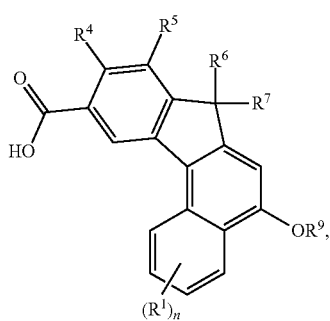

the lactone compound represented by Formula (III-A) is represented by Formula (III-B), (III-B)

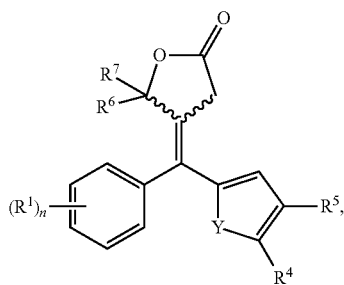

the acid intermediate represented by Formula (VIII-A) is represented by Formula (VIII-B), (VIII-B)

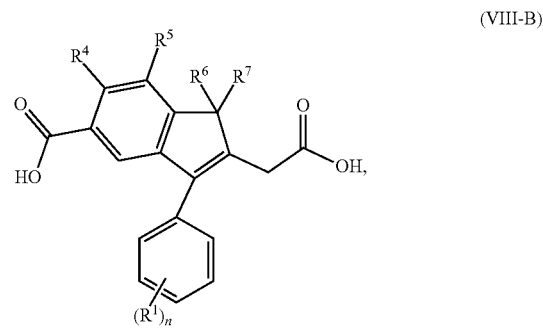

where n for Formula (I-G), Formula (III-B), and Formula (VIII-B) is selected from 1 to 4.

11. A compound, which is an intermediate for preparation of a photochromic compound, wherein said compound is represented by Formula (VIII-A), (VIII-A)

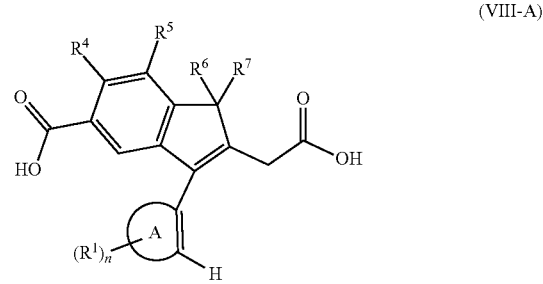

wherein,

Ring-A is selected from aryl and fused ring aryl, n is selected from 1 to 8, $R^1$ for each n is independently selected from hydrogen, hydrocarbyl and substituted hydrocarbyl each optionally and independently interrupted with at least one of —O—, —S—, —C(O)—, —C(O)O—, —S(O)—, —SO$_2$—, —N=N—, —N($R_{11}$')— where $R_{12}$' is selected from hydrogen, hydrocarbyl or substituted hydrocarbyl, —Si(O$R_8$')$_w$($R_8$')$_t$—, where w and t are each independently selected from 0 to 2, provided that the sum of w and t is 2, and each $R_8$' is independently selected from hydrogen, hydrocarbyl and substituted hydrocarbyl, and combinations of two or more thereof; halogen; cyano; —O—$R_{10}$', or —S—$R_{10}$', or —C(O)—$R_{10}$' or —C(O)—O$R_{10}$', wherein each $R_{10}$' is independently selected from hydrogen, hydrocarbyl or substituted hydrocarbyl; perhalohydrocarbyl; and —C(O)—N($R_{11}$')($R_{12}$') or —N($R_{11}$')$R_{12}$', wherein $R_{11}$' and $R_{12}$' are each independently selected from hydrogen, hydrocarbyl or substituted hydrocarbyl, or $R_{11}$' and $R_{12}$' together form a ring structure optionally including at least one heteroatom, $R^4$ and $R^5$ are each independently selected from hydrogen, hydrocarbyl, substituted hydrocarbyl, halogen, —C(O)—N($R_{14}$)$R_{15}$), —N($R_{14}$)($R_{15}$), —S$R_{16}$, and —O$R_{16}$, where $R_{14}$ and $R_{15}$ are each independently selected from hydrogen, hydrocarbyl, and substituted hydrocarbyl, or $R_{14}$ and $R_{15}$ together form a ring, and each $R_{16}$ is independently selected from hydrocarbyl and substituted hydrocarbyl, and $R^6$ and $R^7$ are each independently selected from hydrogen, hydrocarbyl, and substituted hydrocarbyl, each optionally and independently interrupted with —O—, —S—, —N($R_{11}'$)—, where $R_{11}'$ is selected from hydrogen, hydrocarbyl or substituted hydrocarbyl.

12. The compound of claim 11 wherein,

Ring-A is selected from aryl;

$R^1$ for each n is independently selected from,
hydrogen,
halogen selected from bromo, iodo, fluoro and chloro;
$C_1$-$C_{20}$ linear or branched alkyl;
$C_3$-$C_{10}$ cycloalkyl;
substituted or unsubstituted phenyl, the phenyl substituents being selected from halogen, halo($C_1$-$C_{20}$) alkyl, $C_1$-$C_{20}$ alkyl or $C_1$-$C_{20}$ alkoxy;
—O—$R_{10}'$, or —S—$R_{10}'$ or —C(O)—$R_{10}'$ or —C(O)—O$R_{10}'$, wherein each $R_{10}'$ is independently selected from hydrogen, $C_1$-$C_{20}$ alkyl, phenyl($C_1$-$C_{20}$)alkyl, mono($C_1$-$C_{20}$)alkyl substituted phenyl ($C_1$-$C_{20}$)alkyl, mono($C_1$-$C_{20}$)alkoxy substituted phenyl($C_1$-$C_{20}$)alkyl, ($C_1$-$C_{20}$)alkoxy($C_2$-$C_{20}$)alkyl, $C_3$-$C_{10}$ cycloalkyl, or mono($C_1$-$C_{20}$)alkyl substituted $C_3$-$C_{10}$ cycloalkyl;
—N($R_{11}'$)$R_{12}'$, or —C(O)—N($R_{11}'$)($R_{12}'$), wherein $R_{11}'$ and $R_{12}'$ are each independently hydrogen, $C_1$-$C_{20}$ alkyl, phenyl, naphthyl, furanyl, benzofuran-2-yl, benzofuran-3-yl, thienyl, benzothien-2-yl, benzothien-3-yl, dibenzofuranyl, dibenzothienyl, benzopyridyl, fluorenyl, $C_1$-$C_{20}$ alkylaryl, $C_3$-$C_{10}$ cycloalkyl, $C_4$-$C_{20}$ bicycloalkyl, $C_5$-$C_{20}$ tricycloalkyl or $C_1$-$C_{20}$ alkoxyalkyl, wherein said aryl group is phenyl or naphthyl, or $R_{11}'$ and $R_{12}'$ come together with the nitrogen atom to form a $C_3$-$C_{20}$ hetero-bicycloalkyl ring or a $C_4$-$C_{20}$ hetero-tricycloalkyl ring;

a nitrogen containing ring represented by graphic formula XIIA,

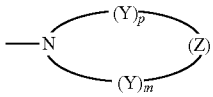

XIIA wherein each —Y— is independently chosen for each occurrence from —CH$_2$—, —CH($R_{13}'$)—, —C($R_{13}'$)$_2$—, —CH(aryl)-, —C(aryl)$_2$-, and —C($R_{13}'$)(aryl)-, and Z is —Y—, —O—, —S—, —NH—, —N($R_{13}'$)—, or —N(aryl)-, wherein each $R_{13}'$ is independently $C_1$-$C_{20}$ alkyl, each aryl is independently phenyl or naphthyl, m is an integer 1, 2 or 3, and p is an integer 0, 1, 2, or 3 and provided that when p is 0, Z is —Y—;

a group represented by one of the following graphic formulas XIIB or XIIC,

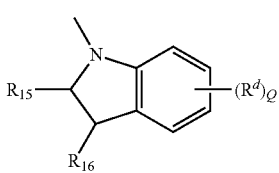

XIIB

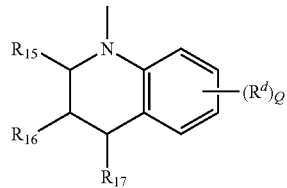

XIIC wherein $R_{15}$, $R_{16}$, and $R_{17}$ are each independently hydrogen, $C_1$-$C_{20}$ alkyl, phenyl, or naphthyl, or the groups $R_{15}$ and $R_{16}$ together form a ring of 5 to 8 carbon atoms and each $R^d$ is independently for each occurrence selected from $C_1$-$C_{20}$ alkyl, $C_1$-$C_{20}$ alkoxy, fluoro or chloro, and Q is an integer 0, 1, 2, or 3; and unsubstituted, mono-, or di-substituted $C_4$-$C_{18}$ spirobicyclic amine, or unsubstituted, mono-, and di-substituted $C_4$-$C_{18}$ spirotricyclic amine, wherein said substituents are independently aryl, $C_1$-$C_{20}$ alkyl, $C_1$-$C_{20}$ alkoxy, or phenyl($C_1$-$C_{20}$)alkyl; or two adjacent $R^1$ groups together form a group represented by one of XIID and XIIE:

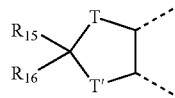

XIID

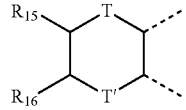

XIIE wherein T and T' are each independently oxygen or the group —N$R_{11}'$—, where $R_{11}'$, $R_{15}$, and $R_{16}$ are as set forth above;

$R^4$ and $R^5$ are each independently selected from,
hydrogen,
halogen selected from F, Cl, Br, and I,
$C_1$-$C_{20}$ linear or branched alkyl;
$C_3$-$C_{10}$ cycloalkyl;
substituted or unsubstituted phenyl, the phenyl substituents being selected from hydroxyl, halogen, carbonyl, $C_1$-$C_{20}$ alkoxycarbonyl, cyano, halo($C_1$-$C_{20}$) alkyl, $C_1$-$C_{20}$ alkyl or $C_1$-$C_{20}$ alkoxy;
—C(O)N($R_{14}$)($R_{15}$), or —N($R_{14}$)($R_{15}$), where $R_{14}$ and $R_{15}$ are each independently selected from,
hydrogen,
$C_1$-$C_{20}$ linear or branched alkyl;
$C_3$-$C_{10}$ cycloalkyl; and
substituted or unsubstituted phenyl, the phenyl substituents being selected from hydroxyl, halogen, carbonyl, $C_1$-$C_{20}$ alkoxycarbonyl, cyano, halo($C_1$-$C_{20}$) alkyl, $C_1$-$C_{20}$ alkyl or $C_1$-$C_{20}$ alkoxy;
or $R_{14}$ and $R_{15}$ together form a ring; and
—O$R_{16}$, or —S$R_{16}$, where each $R_{16}$ is independently selected from,
$C_1$-$C_{20}$ linear or branched alkyl;
$C_3$-$C_{10}$ cycloalkyl; and
substituted or unsubstituted phenyl, the phenyl substituents being selected from halogen, halo($C_1$-$C_{20}$) alkyl, $C_1$-$C_{20}$ alkyl or $C_1$-$C_{20}$ alkoxy; and $R^6$ and $R^7$ are each independently selected from, (i) hydrogen, $C_1$-$C_{20}$ alkyl, $C_1$-$C_{20}$ haloalkyl, $C_3$-$C_{10}$ cycloalkyl, allyl, benzyl, or mono-substituted benzyl, said benzyl substituents being chosen from halogen, $C_1$-$C_{20}$ alkyl or $C_1$-$C_{20}$ alkoxy;

(ii) an unsubstituted, mono- di- or tri-substituted group chosen from phenyl, naphthyl, phenanthryl, pyrenyl, quinolyl, isoquinolyl, benzofuranyl, thienyl, benzothienyl, dibenzofuranyl, dibenzothienyl, carbazolyl, or indolyl, said group substituents in each case being independently chosen from halogen, $C_1$-$C_{20}$ alkyl or $C_1$-$C_{20}$ alkoxy;

(iii) mono-substituted phenyl, said substituent located at the para position being —$(CH_2)_t$— or —O—$(CH_2)_t$—, wherein t is the integer 1, 2, 3, 4, 5 or 6, said substituent being connected to an aryl group which is a member of a photochromic material;

(iv) the group —$CH(R^{10})G$, wherein $R^{10}$ is hydrogen, $C_1$-$C_6$ alkyl or the unsubstituted, mono- or di-substituted aryl groups phenyl or naphthyl, and G is —$CH_2OR^{11}$, wherein $R^{11}$ is hydrogen, $C_1$-$C_{20}$ alkyl, $C_1$-$C_{20}$ alkoxy($C_1$-$C_{20}$)alkyl, phenyl($C_1$-$C_{20}$)alkyl, mono($C_1$-$C_{20}$)alkoxy substituted phenyl($C_1$-$C_{20}$) alkyl, or the unsubstituted, mono- or di-substituted aryl groups phenyl or naphthyl, each of said phenyl and naphthyl group substituents being $C_1$-$C_{20}$ alkyl or $C_1$-$C_{20}$ alkoxy; or (v) $R^6$ and $R^7$ together form a spiro substituent selected from a substituted or unsubstituted spiro-carbocyclic ring containing 3 to 6 carbon atoms, a substituted or unsubstituted spiro-heterocyclic ring containing 1 or 2 oxygen atoms and 3 to 6 carbon atoms including the spirocarbon atom, said spiro-carbocyclic ring and spiro-heterocyclic ring being annellated with 0, 1 or 2 benzene rings, said substituents being hydrogen or $C_1$-$C_{20}$ alkyl.

13. The compound of claim 12 wherein,

Ring-A is $C_6$-aryl, $R^1$ for each n is independently selected from hydrogen, $C_1$-$C_6$ linear or branched alkyl, $C_3$-$C_7$ cycloalkyl, $C_1$-$C_8$ haloalkyl, fluoro, chloro, bromo, iodo, and —O—$R_{10}'$, $R^4$ and $R^5$, for Formula (I-A) and Formula (III-A), are each independently selected from,
hydrogen;
$C_1$-$C_6$ linear or branched alkyl;
$C_3$-$C_7$ cycloalkyl; and
substituted or unsubstituted phenyl, the phenyl substituents being selected from halogen, halo($C_1$-$C_6$) alkyl, $C_1$-$C_6$ alkyl or $C_1$-$C_6$ alkoxy; and $R^6$ and $R^7$ are each independently selected from hydrogen, $C_1$-$C_8$ alkyl, $C_1$-$C_8$ haloalkyl, and $C_3$-$C_7$ cycloalkyl, or $R^3$ and $R^4$ together form a spiro substituent selected from a substituted or unsubstituted spiro-carbocyclic ring containing 3 to 6 carbon atoms.

14. The compound of claim 11 wherein said compound is represented by Formula (VIII-B),

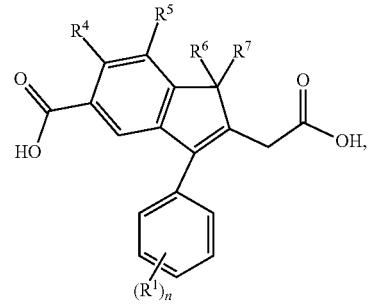

(VIII-B)

where n is selected from 1 to 4.

* * * * *